US009796992B2

(12) United States Patent
Zelder et al.

(10) Patent No.: US 9,796,992 B2
(45) Date of Patent: Oct. 24, 2017

(54) GENE CLUSTER FOR BIOSYNTHESIS OF CORNEXISTIN AND HYDROXYCORNEXISTIN

(71) Applicant: BASF SE, Ludwigshafen (DE)

(72) Inventors: Oskar Zelder, Speyer (DE); Birgit Hoff, Pfungstadt (DE); Hartwig Schröder, Nußloch (DE); Andrea Molt, Weinheim (DE); Holger Hartmann, Schwetzingen (DE); Klaus Ditrich, Gönnheim (DE); Michael Breuer, Darmstadt (DE); Rüdiger Reingruber, Ludwigshafen (DE); Jakob Weber, Neuhausen (DE)

(73) Assignee: BASF SE, Ludwigshafen (DE)

( * ) Notice: Subject to any disclaimer, the term of this patent is extended or adjusted under 35 U.S.C. 154(b) by 126 days.

(21) Appl. No.: 14/084,030

(22) Filed: Nov. 19, 2013

(65) Prior Publication Data
US 2014/0141440 A1    May 22, 2014

Related U.S. Application Data

(60) Provisional application No. 61/728,256, filed on Nov. 20, 2012.

(51) Int. Cl.
| | | |
|---|---|---|
| *C12N 1/21* | (2006.01) | |
| *C12P 17/04* | (2006.01) | |
| *C12N 15/52* | (2006.01) | |
| *C12P 7/50* | (2006.01) | |

(52) U.S. Cl.
CPC ............ *C12P 17/04* (2013.01); *C12N 15/52* (2013.01); *C12P 7/50* (2013.01)

(58) Field of Classification Search
None
See application file for complete search history.

(56) References Cited

U.S. PATENT DOCUMENTS

| 4,897,104 A | 1/1990 | Haneishi et al. |
| 4,990,178 A | 2/1991 | Haneishi et al. |
| 5,424,278 A | 6/1995 | Fields et al. |
| 2008/0148432 A1 | 6/2008 | Abad |

FOREIGN PATENT DOCUMENTS

| JP | H-02256602 A | 10/1990 |

OTHER PUBLICATIONS

"Emericella nidulans Regulatory Sequence SEQ ID No. 2910", Genseq Database Accession No. AXB28604, Nov. 12, 2009.
"Aspergillus oryzae Dityrosine Transporter Gene, SEQ 752", Genseq Database Accession No. AXV91215, Apr. 15, 2010.
"Aspergillus fumigatus ORF Nucleotide Sequence SEQ ID No. 3811", Genseq Database Accession No. AWP32365, Oct. 14, 2010.
"454GmaGlobSeed85906 Soybean Seed Containing Globular-Stage Embryos Glycine max cDNA, mRNA Sequence", EMBL Database Accession No. FK351274, Jul. 2, 2008.
Nakajima, M., et al., "Cornexistin: A New Fungal Metabolite with Herbicidal Activity", Journal of Antibiotics, 1991, vol. 44, No. 10, pp. 1065-1072.
Clark, J. S., "Synthetic Studies on the Cornexistins: Synthesis of (±)-5-epi-Hydroxycornexistin", Organic & Biomolecular Chemistry, 2008, vol. 6, pp. 4012-4025.
Samson, R. A., et al., "Polyphasic Taxonomy of the Heat Resistant Ascomycete Genus *Byssochlamys* and Its *Paecilomyces* Anamorphs", Persoonia, 2009, vol. 22, pp. 14-27.
MacPherson, S., "A Fungal Family of Transcriptional Regulators: the Zinc Cluster Proteins", Microbiology and Molecular Biology Reviews, 2006, vol. 70, No. 3, pp. 583-604.
Shao, Z., et al., "DNA Assembler, an In Vivo Genetic Method for Rapid Construction of Biochemical Pathways", Nucleic Acids Research, 2009, vol. 37, No. 2, e16, 10 pages.
Baldari, C., "A Novel Leader Peptide Which Allows Efficient Secretion of a Fragment of Human Interleukin 1β in *Saccharomyces cerevisiae*", EMBO Journal, 1987, vol. 6, No. 1, pp. 229-234.
Kurjan, J., et al., "Structure of a Yeast Pheromone Gene (MFα): A Putative α-Factor Precursor Contains Four Tandem Copies of Mature α-Factor", Cell, 1982, vol. 30, pp. 933-943.
Schultz, L. D., et al., "Expression and Secretion in Yeast of a 400-kDa Envelope Glycoprotein Derived from Epstein-Barr Virus", Gene, 1987, vol. 54, pp. 113-123.
Van Den Hondel, C. A. M. J. J., et al., "Gene Transfer Systems and Vector Development for Filamentous Fungi", Chapter 1 in "Applied Molecular Genetics of Fungi", Peberdy, J. F., et al., Eds., Cambridge University Press, New York, 1991, pp. 1-28.
Van Den Hondel, C. A. M. J. J., et al., "Heterologous Gene Expression in Filamentous Fungi", Chapter 18 in "More Gene Manipulations in Fungi", Bennett, J. W., et al., Eds., Academic Press, Inc., San Diego, California, 1991, pp. 396-428.
Furuta, T., et al., "Isolation of Cycloclavine from the Culture Broth of *Aspergillus japonicus* Saito", Agricultural and Biological Chemistry, 1982, vol. 46, No. 7, pp. 1921-1922.
"Aspergillus nidulans FGSC A4 protein SEQ ID:22268", Database Geneseq Accession No. ATZ35944, Feb. 3, 2011.
"SubName: Full=Pc22g13590 protein {ECO:0000313|EMBL:CAP98647.1}", Database UniProt Accession No. B6HTL2, Dec. 16, 2008.
"SubName: Full=Uncharacterized protein {ECO:0000313|EMBL:EPS29244.1}". Database UniProt Accession No. S7ZG53, Oct. 16, 2013.
"SubName: Full=Uncharacterized protein {ECO:0000313|EMBL:EAU29280.1}", Database Uniprot Accession No. Q0C7Q1, Oct. 17, 2013.

(Continued)

*Primary Examiner* — Celine Qian
(74) *Attorney, Agent, or Firm* — Drinker Biddle & Reath LLP

(57) ABSTRACT

The invention pertains to the field of production of natural products and, in particular, in the field of production of cornexistin and hydroxycornexistin. It provides polynucleotides encoding polypeptides involved in the biosynthesis of cornexistin and hydroxycornexistin as well as vectors and recombinant microorganisms comprising such polynucleotides. Also provided are methods for the production of natural products, in particular methods for the production of cornexistin and hydroxycornexistin, using such polynucleotides and polypeptides encoded therein, as well as vectors and recombinant microorganisms comprising such polynucleotides and polypeptides.

18 Claims, 1 Drawing Sheet

(56) References Cited

OTHER PUBLICATIONS

Broun, P., et al., "Catalytic Plasticity of Fatty Acid Modification Enzymes Underlying Chemical Diversity of Plant Lipids", Science, 1998, vol. 282, pp. 1315-1317.

Devos, D., et al., "Practical Limits of Function Prediction", Proteins: Structure, Function, and Genetics. 2000, vol. 41, pp. 98-107.

Seffernick, J., et al., "Melamine Deaminase and Atrazine Chlorohydrolase: 98 Percent Identical but Functionally Different", Journal of Bacteriology, 2001, vol. 183, No. 8, pp. 2405-2410.

Whisstock, J., et al., "Prediction of Protein Function from Protein Sequence and Structure", Quarterly Reviews of Biophysics, 2003, vol. 36, No. 3, pp. 307-340.

Witkowski, A., et al., "Conversion of a β-Ketoacyl Synthase to a Malonyl Decarboxylase by Replacement of the Active-Site Cysteine with Glutamine", Biochemistry, 1999, vol. 38, pp. 11643-11650.

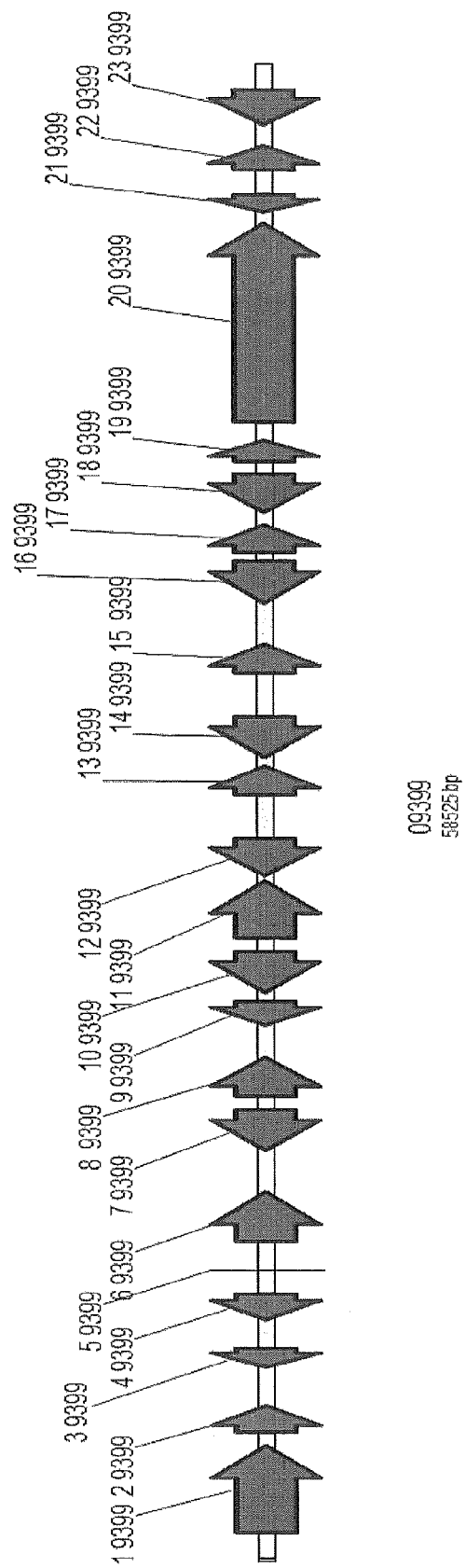

SEQUENCE LISTING

```
<160> NUMBER OF SEQ ID NOS: 58

<210> SEQ ID NO 1
<211> LENGTH: 58525
<212> TYPE: DNA
<213> ORGANISM: Paecilomyces divaricatus
<220> FEATURE:
<221> NAME/KEY: gene
<222> LOCATION: (1001)..(4395)
<220> FEATURE:
<221> NAME/KEY: gene
<222> LOCATION: (4937)..(5965)
<220> FEATURE:
<221> NAME/KEY: gene
<222> LOCATION: (7505)..(8236)
```

```
<220> FEATURE:
<221> NAME/KEY: gene
<222> LOCATION: (9322)..(10368)
<220> FEATURE:
<221> NAME/KEY: gene
<222> LOCATION: (11274)..(11354)
<220> FEATURE:
<221> NAME/KEY: gene
<222> LOCATION: (12423)..(14345)
<220> FEATURE:
<221> NAME/KEY: gene
<222> LOCATION: (15965)..(17599)
<220> FEATURE:
<221> NAME/KEY: gene
<222> LOCATION: (18123)..(19631)
<220> FEATURE:
<221> NAME/KEY: gene
<222> LOCATION: (20880)..(21831)
<220> FEATURE:
<221> NAME/KEY: gene
<222> LOCATION: (22165)..(23763)
<220> FEATURE:
<221> NAME/KEY: gene
<222> LOCATION: (24308)..(26547)
<220> FEATURE:
<221> NAME/KEY: gene
<222> LOCATION: (26750)..(28222)
<220> FEATURE:
<221> NAME/KEY: gene
<222> LOCATION: (29894)..(31024)
<220> FEATURE:
<221> NAME/KEY: gene
<222> LOCATION: (31399)..(32996)
<220> FEATURE:
<221> NAME/KEY: gene
<222> LOCATION: (34706)..(35799)
<220> FEATURE:
<221> NAME/KEY: gene
<222> LOCATION: (37437)..(39097)
<220> FEATURE:
<221> NAME/KEY: gene
<222> LOCATION: (39414)..(40500)
<220> FEATURE:
<221> NAME/KEY: gene
<222> LOCATION: (40981)..(42510)
<220> FEATURE:
<221> NAME/KEY: gene
<222> LOCATION: (42995)..(43808)
<220> FEATURE:
<221> NAME/KEY: gene
<222> LOCATION: (44518)..(52300)
<220> FEATURE:
<221> NAME/KEY: gene
<222> LOCATION: (52707)..(53415)
<220> FEATURE:
<221> NAME/KEY: gene
<222> LOCATION: (54385)..(55295)
<220> FEATURE:
<221> NAME/KEY: gene
<222> LOCATION: (56158)..(57525)

<400> SEQUENCE: 1
tgagaacgat agcagaagaa tagtaacgtg ttgagtcagc tcattacaaa ccgtctcgaa      60
gctttccgat agattattgg atgagtgggc tgggactcac ggtccgaacc tggtttccac     120
aggacgcttg cgaatggagc atggcaagcc agctgttggg aggggatgat tcgtggagaa     180
gcttgcccca gcgtaccgta accggggagg gcatcctacg tgtcctgaag agtgagaaac     240 cctcggggggc agtcgactaa atttcagata tgatcctaac tgaaagcgtg cttcaccaaa    300
gcgcattgtg agtcgatatg cctaatcgat ggattaagtc tagttatcct gtgaatgtaa     360
gaggtggtag cagctgttga gggcccaggg actaaagagt cgtggccctc caattgtgct     420
aaagaactgt gtaaggatga gagagcctga tttagcttat atgaaacaga tttccgtatg     480
```

| | |
|---|---|
| gcaaattgta ttatctgcga tccagtactg caacatggag cacaaaacct aggctctgta | 540 |
| ccattcgcgg ggcttccgtg gagaggtttc cagggtcagc tacctaccta ggtaggacgc | 600 |
| ctagcgaaag cattgctgta ctaatttctg acagaagatt actattgacg caatgtggcc | 660 |
| ctcggatcag gcgtccactc caggttcagg acgaatagac gtggttatct gagcgaattt | 720 |
| gccggcgcag ccagggtagc tgagtacgga tgcgtgagaa tattacctgt taaaggctca | 780 |
| aaatgacaag catttcctcc tgtgggatgc aataccatct tatcagaggg tccgttcact | 840 |
| cagtgcctgc gatatttatt ggctcttgag cccctcgatt atttccttat ctctcatgct | 900 |
| catgttgagg aatctggtaa taactccctg gtgatcgctt ttgcgcgaag acggcaccta | 960 |
| ctcagtacaa cttgtgttct ttcttgacag ttttgcaaag atgggctcga gtaccttcga | 1020 |
| gcacgatagc acccccgaat atgggaaacg tttcctaccc catatgatcg atgaaagagc | 1080 |
| ggcttcaggc cattcacgtc cttatgctta tattgccaga tctccgcatc cccaggacgg | 1140 |
| cttcgaggaa gtcagctacg cacgtctggc gaatgcaatc aaccgggctt cctggtgggt | 1200 |
| agtcaatgaa ttaaccccctt tgactggtga gaatggtgtc ttcgcgtaca tgggtccgaa | 1260 |
| cgacctgcga tatctgatac tgtctgttgc ggctataaaa accggcagaa aggtgggtta | 1320 |
| cctccattta ctccatagga cgaagaacac ggctgatggc gtagatgctt caaccatcaa | 1380 |
| tgaggaatac tgttgaagca cagcagttgc tattccaacg catcggatgc aagacaatcg | 1440 |
| cctacgcagc taccctggag aagagtctac atcctatttt cacatccatc tccgggctgc | 1500 |
| agaccaagca ggctcctagt ttagaggatt tcctttcgga agatgtggtt cctcacttcg | 1560 |
| aatacaaggg cagctacgaa aaattgaccg atgaaccgct catatacttc cacacgtctg | 1620 |
| gatcttcagg tctgttgcct ctagtttact gagcgcatct cctagttaac tatgagaaca | 1680 |
| ggaaatccga aaccaattgg tttcagtctg cgatggcttc ttctcttctc tgatgctccc | 1740 |
| aatttacccc ctattaatag tcgcccgtca acagtgaagg agggcctgta ccgccaaaat | 1800 |
| actttatgtt tccttccacc gttccatgta tgtatgggggc cctggatatc gagtgcatga | 1860 |
| tccttgtgag ctaaactgta ataggccggc ggattcggtc ttgctgccgc agtggtgtac | 1920 |
| tttgaagcca ttgctgtttg tcctcatccg gaggttgcac caacagcaga atacatattg | 1980 |
| tcgctgctag accaaaatat tgccacggcc ttatcggttc cgccttctct acttgacgca | 2040 |
| ctctcgaaga catctgctgg gatcgaggct ttgtctaagc tggaacacgt tggctacgtc | 2100 |
| ggaggcccgt tgcccgagca cgttgggcag gctcttgcgc caaagctgaa gcacctctac | 2160 |
| agtctaatgg gggcaacgga gtgtggctgg ttccatacca tacctggcga cagcagcaaa | 2220 |
| tgggcgtatc tacgtttcaa cccggatatt ggctatcggt tcgatgagat ctccgaaggg | 2280 |
| gtcttcgaat tggtcatacc taatagtccc gtaaccagga aagtgcatgg taccccacat | 2340 |
| atatttccgg aactgaacga atacagaaca agagatcttt actccttagt cccgggagag | 2400 |
| gaagggtgga tgcgttacca gggaaggagt gacgatctta tagtcctgtc caacggtgag | 2460 |
| aagatcaatc ctgtacctct ggagggtatt ataaacagcc attcagcgat caagggtgcc | 2520 |
| ctcattgtgg gggagtatcg attcttgcct tctcttctga tagaggtcca ggatgatttc | 2580 |
| agcgctgaaa cagaagagga gcgtctggag ctgcttgaca agatctggcc aaccgtcgaa | 2640 |
| caagcaaata agatcgcccc acgcttctcc cgggtaccga agtccttgat ctatcttggg | 2700 |
| aagaaggatg aacactttca cagagctggg aaggggacca tccagcgtca gcgcaccgtc | 2760 |
| agcaactttg cgaaggcctt agatgaacta tacttcgctg cagagcaggg gctgcttgtg | 2820 |
| gaaggtctag agttggatga ccccctcaaat aaggattcga tcagagcgtt caccaggaag | 2880 |

```
ctttacgctc aagctctaga tgccgaggaa atcaaagacg aagatgacgt ctttaatctc   2940
ggcatagact ctcttcaagt cgctatcacg gttcagaaga ttagggcgac catgagggca   3000
cgaccggtag aactggacca tgagcagatc aatggacaac tgatttactc taacccaacg   3060
gcaggtgacc ttgcaacggc cctcaataag ctcgtaaact gtgaaagagg tgtacctctg   3120
gacggctctc tcaatggtgt caacgaacgt tcgactcgtt tgcagcagct acttgacaag   3180
tacatagcag caatgcccac gatgctcgat gaggcgaaaa agcgaatac gggccgctcg     3240 actgtcattt tgacaggttc aactggttct ttaggaagct acctcttgac aaccttgttg   3300
tcctcgcctg cagtctcgaa ggtagtctgt ctcaatcgat ctagtgacag cgaaaagcgc   3360
cagagagcta ttcataacgc acgtggacaa gctatatctt gggagaaaga agaccgagag   3420
agagtcgaat tcttaacagc agattttatca aaaccagacc ttggtctggg ggatcagaaa   3480
tacagtgatc tattgtcaga agcatcagca atcatccact gcagctggaa agtcgatttc   3540
aatcacactc tcagttcttt cgaagcgacc catattgccg gggtgataaa tctgatcaca   3600
ctcagcgcca aatctgcaca ccacgcacct attatgtttg tctcgagtat atccacagtc   3660
ttcaattgga tcgaaacgca cccgaatctc cctgtcccgg aagccattct caatgatcta   3720
gacagctccg agaaactagg ctatggagag tcaaaatata taggcgaaag actaatcgag   3780
gcttataccg cgtccacggg cattcaaaat gtcgtcctga gagtcggaca aattgcaggc   3840
ccggtacttt cctcttctgg attctggaat aagcaggaat ggttccccag cctggtcgcc   3900
agctcaaaac acctgggatt attgcctgag tcactaggga ctatgaatac gattgattgg   3960
ataccggttg accttctggc atcgattatc acccagctgc ttcaatccgt ccacaacagc   4020
ccggaatccg aagtgaagtc acctgctgtc tataacctcg tcaaccctcg agtgactaca   4080
tggcccgctc ttctccacag cgttcaagaa gaccttggtg gacaatcaaa cgtacgagtc   4140
gtcccattgt cagaatgggt ggaagcgctt gagagaagtg cttcgcacaa tcacgggtat   4200
gtgatagcag agaacccagc tgttaaactg cttgatttct tcaagctgct agggaagaac   4260
ggagagggga acgtgggcga agcgaaatcg caatataagg tagctcgcct gctgagggat   4320
agtccacagg ctagacagct gggcttcgtt tctccagaat ggatgcggat gtggttgaag   4380
cagtggaagt tgtgaaatgg ctgattcatt gtcttgtgat tctatattat ttttatgttt   4440
tattagcaac gttgatggat ggggcccact gaacgagata cttctatatc tgaaatagat   4500
tgaccgacaa gaatatcagt tctattccat atcagatgca cagaacaatc atgagaaact   4560
gggctaacca gtgacgtgcg gttgaccaaa tcctatagtt cataaactga caggcagcca   4620
ctagaattcc gaggttcatc ccgccaactt tatcttcggg ttaggatatt tctgctaagt   4680
ttggtagact actcttcatc ttggttggca cgtaaggcta cagcgccagg catccaccaa   4740
ctgcagagtg aaatgagggc gggctccgca ctcttcactc tgtgcatcgt cccttgttat   4800
tgtttattgc cagcctcacc gtgtctttcc agtaccatgc ctgtgtccat cttgcaaggc   4860
actcgaggat tgttctaggt cgccgacaga gatcagcatc gttcgtatat ctgaaacaac   4920
cgatactcag tccaacatgg gctacctcga gaatctgccc gcagaactgc tgttcctgat   4980
cgtcgaccag cttgacagat atgacttgat gaacttgcgc gtggtacacc ggcgcttcag   5040
tttcgtgaac ccacgtgtct tcaaggtcat gcgtttctac aacgagccta ccgtccccgt   5100
gaaacttcgc aagctgctca acgggagga tatgagatcc gctctggacg agataatctt   5160
ttcgacagac tctctcttcc gggggttacaa ccggcacgat gcagccctga ggctcaagag   5220
```

```
ggttgcccgt ctgctcgcaa atcacgacga tgtcaacatc aaaaccgtac atctcgtcgg    5280
cgattcagga ggtctgggac ttctgcttcg ttactttgca gaagcaggta tcaggtcgct    5340
tcggtacctc tctggcgcca taattttcg ccaccatgag atcaacgagg aatggcttcc     5400
tcacctgatg gatgagtctg gcgtcttgga agtcttggga ggcttggaac gcctggacct    5460
cactctcaat aataggtccg ggtttatctc gcaccccgc ggttttccc cccacgattt      5520 tcccaacata tacagcatca tggccgccac gccgagcttg actgagctcc ttctcaaggg    5580
cattgaagga caagatttta gcgacatgtt ggggtgtttt atgttcttcc ggcggaggtc    5640
ggcttttcct ccccggctcc gaaaagtgac tgtggagcgc tgccacactc cgctcagctt    5700
cctcacacgg atcatcaacc atccaagcat cgaagatgtc accctctctt cggtctctct    5760 catttttggat cgatctgagg gcattgatgc gaggcggtat tatatccgta agtggcagga   5820
cttcttggaa gctttcagtg atatatacta cgacggcgag gagactcgta agcggttgac    5880
tgtgggcgag ttgtgggaac gtggcaatct ggctacgatt gacgttaacc atttgcttgg    5940
agtgactcta ttggatccaa actaaagcct aggtgtggag ggctagatag cctgtggtgg    6000 acacttacg cagtcagttg ttcgatactg tggcacatat cgagttggag agctctagac     6060
cgtcgatgac tatctacttg ttctcttcca ttcgatattg ttcttttgta cccaccgatt    6120
tgattgtcat acttttcgct taaactgttc gtgggccgag ataataaaga cgattactta    6180
gattcatagc ttcaaggcac aaagtttaat aatgttaatt agaaattcgt acgtgtgaca    6240
gttcttaaat gagctcctga ctgctggccc agaaacaggc tgctaggagt ctagagagaa    6300
aaaacagaag agagagggac ggggggggg ggttgtatag ataagtatta aagtgatcat     6360
ggtcggtcag tcgcaccgtt ggcaggcgca cggaccatgg gtgcgatcta ttgattgcgg    6420
aggagacgcg acgggatcca cggaccccaa ttgattgatc aaccaatgga ggggcgataa    6480
actcccaggt gggcataggg gacatggtcg tgaaatagat ccaaaatagg tagggttgaa    6540
gctgcggaga gcaggagac cggggggtccg tgtctagttt agccatacta cacggaatac    6600
agtacgatgt cgacgtatac tctaatcctg ctggattcag cgtatcgcac cgagcccgca    6660
ggtggtgtta gtggcagaac accaccggca gttctctagt taggaagatg tgaaagcctt    6720
tagggaaggg gatcctattt ggctagtagc ctagtactat ctagaggttg tggatttgaa    6780
tcttactgta agcaaaagtt gccgtatttt gtgggaaagg cgaagaagcc tagattcagg    6840
gatgctaggc atcgtgagct acctacctag gtaggtagct atatagccat gccaaggcac    6900
taggcgagga catcccggag gagcacggaa gacgtggtct ccaacataga tattttagat    6960
accttcttag ggagatctgg atgggtggct agtctattct aagttatgga ggcgggacgg    7020
gaggggaaca caggctagtg ccatgtgctg atatgcccctt attcctacct agctagtgga   7080
tatgaagaac cttatctgag ggattaattg gctgttttaa cctgctcctt ataagaaagg    7140
gactagttaa ccttatctat gcagaaattg tgaaggaata atgaagaatc catcttatgt    7200
aactagctag ctattaactt attggggggcg gcaggtcaga gaagaatcca tcctatatat    7260
aacaggaatt ggactagatc tgcatgtgat caagcagaaa ggatatactc tagagtattg    7320
aagaccacta cagaccatct attttgtggcc tattgataat cggattaagt tgacagatcc    7380
gtgaatgaac tgattgattg attgcatgta tcccaccca catggcgcca tatctagccc     7440
tgacgagtcc actgaacccc ggtgcaaccc cataacgcgt gaaaataaac gtccgccctg    7500
ctcctcatct caaaagcccg accaacgtca ctagccggtc catcgacacc atcagagagt    7560
cctcgcactc ctgcagcgag aaggattgtt gggggcgatt ccgatgccac acattctcca    7620
```

```
ggatgagttt cagctcgccg atcagggccc ccaggtccgc caatcgccgg cgcaggagca   7680
tgccggcgag cagttgcgcg tcttcttcat ggatctcgat atcgcccat  gtcatcgggc   7740 tggtgcaaca gaccgggggc ccgttcatcg tcccggggaa atcgtccgcg ctggccagac   7800
cgtctgctcc atcggaggag gagccaggtg gccgaggaag gacagcgtc  gaggagcggg   7860 atctccgccc ggtgcccaac cgctccgggc tcctcagatc cccttctccc aatgcatagg   7920
cggaaaaggc ccctcatac  agggccaacc ccagatcgag gacgcactgt agggtgatga   7980
tggcatgcca gtgggtccgg cagtgctcgc aggccaccat gtgcgcacac tgggtggtga   8040
tatcggcgcc caaactcagg atcgtatcaa aggagaccgg gtagtgatct ggcagcttcc   8100
ccatcacctg caccatgcca tggatgcaat cgcacggggt gttgatgttg gcggcgttgg   8160
cttgaatgtc cccataccgg cgcgcgagga tctcgatgtt ctgtacggca ttgggcgtct   8220
tgacggtggt cagcatggtc actcggtggg agcagctcaa ccggctggcc tcatgggagg   8280
caacggatga gtctggatta tatcatgtag tgcgaagcga atcgtggctt ggggtgagat   8340
tcgtcagcgc ttctcccaag ttccagattt tcagactgcg cgaactggcc ggaggctcta   8400
tggaaaaaga aaatagtgta tacacagtat aaagggtata ccttggccga tgtcaaaagt   8460
aagaccgatc ctgatccctg gtcactgggg gccagtggtg tttcggatgc actcgagccg   8520
cgggaggttt tcgacagcct ccaagccacc ttgacatgat gacgatgatg actgcatctg   8580
atccgccgct tatcactgca acaaggggca agaaagatat ggaaagttcg cagtacttct   8640
cagtgatcga attgcgactc tcatgtcagg atcagccag  tcaggcccgt ggtggctccc   8700
agatggtgtc aggaccgact cctctgggcg gttcgctggt gcctgggcag tctgcttagt   8760
cggccaccga tctagttata tagcagtcca gacccaagtt tcggcttcct tcagatcctc   8820
gtgtcgccac gggacgccaa tgagcttgtt ctggccctcc agatgatctg ccggagagca   8880
agaacgcgga atccttccga tccgtcccct gtagttcctt ggctgggacg tactagattc   8940 tccctgggc  ccgtgtcttc cgcactctta tcttacgtct cttgcgcact tttggccccc   9000
atccccggga attaggagga cccctcctgg ctattgccat cttccggaac acggctaacc   9060
tgtgaggtca ggatgagtgg gtagatgaga tccgacaagg tacgcagtga gaatctattg   9120
aatgtgacag tcaagaaaga aaccgctgat tgcatggctc tatgacacaa agacagagcc   9180
ttggatatgg gtactagatg cttccagcaa gatagagtct ggatatattg ttctctcttg   9240
ccatcagtct gtttattgag ttggaccatg accatcgctc ttcaatagca ggcagagcgt   9300
gaatcttaca gcttctgcaa gctaggtatg tttctgagcc atatggtatt tttcaatccg   9360 agtgagggc  tgctctttgt cccccagaca tgcctgggcc gaagctccga tctgcatcac   9420
ctcgtccggt gtgatctgga agtcgaagac cctgagatac cccttcattc ggtcctcatg   9480
gcgactggtt gtgatcgtgg caaccccctg ctcaatacac catctgagac acaccagatc   9540
agtgcccacg ccatacctgt tggccacttc tttcaaagtc tcgtcgagtg ggcccgggat   9600
attccttgtg attggcgcca gggcgccata agcggagatg gtgatgtccc gcatattgtc   9660
tcgtaggctg aagagatagt cgttgccatc tcgaaccgag agatatgggt ggaattcgag   9720
ctgattcacc gagggtggtg tttgcgcggt tgccaaaacg gtccggagat gcgtcgactg   9780
gaaattcgag acaccaatgg ttcgggcctt cccactggcc ttgacctcct ccatgccttt   9840
ccaggccttc tgcaggtcgt cgtcggattc cgcccagtac ggggtatgaa tgagatacct   9900
gtagacagat caaggctagg atcgatagga gctatttctc tgcagggggg aatgacttac   9960
```

```
gcgtcaacgt aatctaattt caattttttgg aggctgacat caatcgactt ggagatgtta    10020
aggaagtcac tggagacctt tgtcgtgatg aacagctcat ctcttccctg acaatgccc     10080 tccgcaatgc tttcgtggat ggccgcaccc acttcgagct ctgtattgta catctcagcg    10140
gtatcgaggt ggcgatagcc gacacggagg gcttctttga cggcatccac cgtcggtcga    10200
tgcagggcat ccgatccaga acgtttcaag aaagcagtgc ccacgccaaa tgcaagctaa    10260
aaaagcagta ttccataagc accatgcaat tcaaaatgac aaaaaggatc tggtagtact    10320
tactgtgggc attaagacgc catcattcag agaaagcttg tgcgacatgg ttcaaattca    10380
ccaatcagaa ggtgatattc tacttctaga gctgggacga ttcagtcaag cttctcaggc    10440
cggagataag caaactattt atcaccctgc aagccggaac cggcgcggtg ccggaataca    10500
tgatcgcctg ggccggcctt tccccaagag tccattactc gcgaagcttt aagacaccgc    10560
gcccttcaat gacagcattc cgtggtgaag gtggaagccc ataccatcat atatagcttc    10620
gattcggact agtaaacatt ccaggtgcca agtactgtct agagtcatac tcccctgaac    10680
ctgaaaattg ccctgaacct gcagtgggga agtcttttga gccggaaaat aaatatcaaa    10740
agaaaaccag aacagacgaa tgaagtcact ttcaccaaga gaccgacctt ataatttctc    10800 agagctatttt tgaacagaga tacagataat actatttaga gtaaattaga tttcagattc    10860
agaccagcag tatcgactaa ctcgacccgt agatttgcca cgtctagagt ctagaccaga    10920
tacatatact gtatccgtat cctacaaaca gctttataac cctttttttg cataccaaaa    10980
accccacaga gattctactg aaattctgaa tgcgagaata aatgttgggg accacgtctt    11040
ccgtgctcct ccggatgccc tcgcttaata tcttgacatg gctatatagc tgctcaggat    11100
cccactagca tcctagaatc caggcttctt ccccttcccc acaaataaac aagctcctga    11160
gtcctgagcg aagcgatagc aaaaatcaat acagaaagaa tagattagac ttaccgtatc    11220
cgcatagaca agcctaccct accaatctag gggataaaga gctctcctac aacatggtaa    11280
gaagaaaata atgagaatgt attaagctga ttctcttcta gatcggctct cgtgctactg    11340
atggcacaag ttaggattga cacctctggc tccaagatag ctgcaagccc ggactatcta    11400
gtttgactgc tatatcaata ctcaaaaggg gtaaaggaat tcttttcttc ttcccttctc    11460
tattgagatg cctgcctatc tgatgtggtg tatggtgttg aaattattct gattgaggag    11520
aggaagaagt ctagataggc gcggaccatg gtcctgatct aaatacatag ggtcacgtga    11580
cttcggtaga gatggctcaa gccgtgtcac tatcaggcct gtttcatgat aataccttac    11640
attcctattc aatatacatg tgatattgac ctttaaaaag acctttaaga gctgaatatt    11700
ctaaaataga aaataagaaa aagagatgta agaaataaaa ctactctgta ttccggacgt    11760
cggagccggg ggatccgaca tactacgttg tactgtggct gggcggctat tgatatagaa    11820
tacatgacag taccatacag cttctccaac cagggcccgg agttttcggg cttaaggcct    11880
gagtgcagga tctcgatcaa ctcaacattc gaagcaatat atattatata ttattggact    11940
agaccaagct acatgcagtt tggcttgcat tacaacacag acacacgttc cttaggcttg    12000
acatatgatc ctcgccaaga aagtggctga cgatccacgg atgggagtat cagacccaag    12060
agatccctcc gcctggcgtg ccttggattg taggggtaaa aaccacggtt ggaagaccag    12120
cgtggaaata tagctacaac tggaggcttt tctgaacttc tgggtgagat ggtcagtaag    12180
aaaggtggga atgtaccggg caagcaagcc gcaacaaatg tctcgcgctc gaaacaagtc    12240
catcgtccta tgacgtcaac acacgccggc tgggaaaaga ccccgcccgg tgagacgaga    12300
cataacttaa cttctccaaa gattgatcat atctttggag ttctgattct atcttgcttc    12360
```

```
atattgatcc atctgacacc aaagcttctt gtattcccat caaatcaaat acagtcacga   12420
tcatgagcag ctataaattc cccgtcgacc tcaagcagtt caagcagctc aagcttgacc   12480
caaaaagccc acagctttct gctcagcaga agaacgacct cctgcataac atcaacattt   12540
tcagagatgc aatcatcgca ttcacggcca cgggtgccgc ccgtggactc gcgggccaca   12600 ctggggtcc gttcgacact gccccagagg tctgcatctt gctcgccttc atgaacgcga    12660
accccgatgg tttcgttgat gccctgtacg acgaagctgg ccatcgggtt gccacgcaat   12720
acttgcttgc tgcgctggac ggaaagattg accccgacca cctgctgaac taccgcgctg   12780
ccgattcgaa actcccgggc caccctgagc ttggcctgac gccgggcatc aagttcagct   12840
cgggtcgtct tggtcacatg tgggccatgt gcaacggtat ctccatggcc cacaaggata   12900
agaacgtcct gctgctggga tcggatggct cccagcagga aggaaacgac gccgaggccg   12960
cgcgcattgc cgttgccaaa aacctgaagg tgaagctgtt catcgacaac aacgacgtca   13020
caatcgccgg acatccttcg atatacttga agggctacga gatcgctcgt acgtcgagg    13080 ggcacggctt gaaggtcatc cgcgcccagg gtgagaatct ggattcgctt tacggggcga   13140
tgtgtgaaat catcaactac aacggccctg ccgctgttgt ggtagaccgg aagatggccg   13200
caggcatcga agaaattgag ggagagaccc acgctcacga tgtcattccg gtcgatatcg   13260
ctcgcaaata ccttaccaag cgtggataca gcaaggagca gcttgctttc tacgaccaga   13320
tcaagcctgg atcgaacccg caccagtacc agggctcaac caaggagaag ggtgcgaacc   13380
gtgcgatttt tggtgaagcc gtgaactccg tgctcgacgg cctcagcaag gaagagcgtg   13440
tccgtcgggt catggtcatc gattctgacc ttgcgggctc taccggcctg aaggcaattc   13500
aatcgaagca ccccgaggtg ttcgttgcat ccggtgtcat ggagcggggc aacttctccg   13560
ccgctgctgg cttcggattc ggcagcaacg gcgagcgtca gggtgttttc tctactttct   13620
cggctttcct ggagatgtgc gtctcggaaa ttaccatggc acgcttgaat cgctgcaccg   13680
tcctctccca cttctcccac agcggtgttg atgagatggc cgacaacacc tgccactttg   13740
gtctgaatct cttctttgca gacaacggcc tgatggatgc cgagagcaca tcgttgtact   13800
tccccgccga cggtgagcag atgaaggcgg tcgtcaacaa ggtctttggg ataagagca    13860 tgcgtttcat cttctcaacg cgttccaagg ttccttacat cctcaaagaa ggtaccgacc   13920
agaagctcta tggcgacggc tacgagtttg tcccgggcaa ggaagaagtc atccgcaagg   13980
gttccgccgg ctatgttgtc tcgtacggtg atatgctcta ccgctcgctc gatgccgttg   14040
agcgcctgcg caaggagggc cttgatgttg gcctcatcaa taagcccaca ctgaatattg   14100
tcgatgagga caccatcaag gtttacggat cgactccgtt cgttgtggtc gtcgagtcaa   14160
ttgctcagaa gacgggtctt ggctcccgcc tgggcagtca ccttcttgag cgcaagctta   14220
cgcccaagtt caaggcgatt ggtgccgtga gggagggctc tggcggcttg tacgagcaga   14280
ttaatgccca gggtcttgga ccaaacgaca tcattgcggc agtgaaggag gtcagtggga   14340
aataaatctg ccatccttca tgaaaataat gacttctgag aatgattttc tctttattaa   14400
attgactcta tcaagattgt catgaagtta tttctgtaat ttttatttt attttagcta    14460 gtagactact atctgcaggt ggatcttctc ttctcccatg tttctaccag tagaagatca   14520
caatatcgaa agaagtagaa aattagaaat atgtaagaaa aatatcccaa gtcacgtttt   14580
ctggcgacca caccagtacc acttcccggt gaattatttt cctgccgttg ttctcccctt   14640
agatgattgg agggcattgg aactgctgat aaacttagac cagctctcat atacttgata   14700
```

```
aacatattat ataggagaa ttactttata tatcctataa ccgttaatca tgcaatcata    14760
cctacttgac catattctta gcttatccag ttcagtaacc atcaataggg atcatgtctt    14820
cccccatgaa gggcaaaaag gcagagggag agcaatcccc tcaacaacct ccccgcccg     14880 caccagaaga catccaatcg aagaatcccc cccccccccc caccccttg ttgtaaagct     14940 gagaaataca ccccccaggc cattcccacc aaccgccaat acctgtgctc tagtagtcga    15000
tctatttcaa gtcccgtacc cgcccatac ccatacttct tttccggcac attaacggat     15060
cccctccatg cctctctcag agagattctc gatccgcccg aggaacctga aactccgagc    15120
tgcaattttt ttatgtgcta caagtgtaga ggaaactgtg gggttgatat ctagccttac    15180
ttgacccccc tcccaggtca attgttgaag gagctgcata ctgtgttttc gaacagtgga    15240
agacggagtc ccgattccaa aaaaaaaaaa aaaaaaaggc ccagcctgat ccaataaccg    15300
ctatgcacct cgcccaacta tattctccac aaaccttccg ttacactaac cccgataaat    15360
tttggctact tttgtgtaaa agaaaatgcc cggacttgac tgggcgtatt actagacgac    15420
gtggtatact agtcaaaaaa gaacatccgg ggccattttc tcacgtgtac ggtgctggtc    15480
tttttttctg gggttctctg aagggggcgcc gtggcattgg aggtatggta tccccgaacc    15540
aatgcaaaag tggctggacg gtacagtaca tggagtgggt ttatttatac tgggaatggc    15600
tttttatccc ccttgtcggg caagaaactc ttgtcatttt agcatcggtt ttttttttt      15660 tttctggttg cgcatgggtc ccgatttcaa ttgatgaccc cacatccaag cgagcttgat    15720
tcctctataa aaatttatag taaccgagcg gtgagaataa tagactagta agagggaagg    15780
tctagaattt tacttggact atattgatat atgcttgggg aagattattg gacagtatcc    15840
ctgatctcta tattcaacaa atacaatcca agacagtaga tctgaacact ggagcatgta    15900
tctggctcgt gtgtggatcg gatctcaatt atactcctcc atggaggtgt ccaccacaca    15960
tccatcagtc gacatgccat ccgatctttt cgcgtcgccg cttcatcatc accttgccct    16020
ggaaagaagg catgacggcg gtgacgagga tctcattccg gggtggcggg acccctcct    16080 ggaacttgag gtcgtagttg agcagcaagt agatgaggat catcttgatc tcaaaggcgg    16140
caaagaagcg gccgggacag gcgtgggtgc caaaaccaaa cgagagttca ctcgtgctgc    16200
atgtgctctt agtagggggt cattcattgc gaagaaggaa taggatgggg gttgaaaaaa    16260
gagctcacct ggtcgacacg agctggtgca ggttccgctg ctgcggctgc aggcgcatcc    16320
gctcgtaccg gaaggcgtcg aactggtccg gattcccag gacggactcg tcgctcgtgg     16380
catcgtagtt ggaggtggcc acgaagaggc ccttgggcag gatggtgccg ttgctcatgg    16440
ggatgtcgct catgatcttg cgggacatga cgataagccc cggcgggcag aaccgctggg    16500
attccttgca gaagctgtcc agcttgttgc acttggtcag gagctgcttg tcgatctggc    16560
cgttcgtctc ccggagcagc ggcaggaact cctggcgcag cggctcgatg cactcgggat    16620
gggcggccag gtcgaagatg cagtgggtca ggttgtgagc ggtggtgtgt atcgagacga    16680
tgctcagcgt gagctgctgc tggacgagga agtcgatatc ctcgcgctcc gccgggtac     16740 agttatgcag cacccactgc atcatgtcgt tgggggctt gaagtccggg cgcttcaggt     16800
cggccagccg ctgctcgagg atgggacgca ccagggcgct ggcctccttg cgctgcttct    16860
ccaactcttt cgactggggc gcaaagcgct ggaggatcgg ccgcagcagg aagggatacg    16920
gcccacgggc ccgcgcggcg gccttactga ggatggtgta gcggatcatg atctccagcc    16980
agcgctcgtt gcgactgagc ggcaggccga caaaggtgcg gctgctcagc agggcgatga    17040
gctgcaggtc cgtgggatag acggtgatgg gcgtccagtc cacgcagggc ccgatgtgct    17100
```

```
tgtcgaccgc gtagacggtc tcatccagca gcagggaaa ggagcgcgca gtgtgacggg    17160
tcagctcgtt cttggtggtc tcgatggtga catggtcgac gagggcgatc ggattgccct    17220
tgccccagcg atacagccgt tcggcttcga acgagatgtg gctctcgggc agcgacttga    17280
gctcctccca ccatttccgg gggaggatga ccgtaggatg atggggcgtg ttgaggatga    17340
agggttgatt gcggtactgc agtctcgtca ggattcatcc atcatgatcg agccacgatg    17400
acagaaagtc actcaccttg gctttgccct cctgcagagc cgcgaggaat cctttggcgt    17460
gagacaccac gggggcatcg aacggggaa ttcggttctg gatggagacg gtgaggaagt    17520
acaggacgac caggacgacg ccggtgccca caacgagggg cgccagagag ggcgcatcca    17580
gctctttcag cagatccatg tcgggagagg ctcttcagat caattcactg cggacaatct    17640
tcgatcctgg acggcgtgga gaggcggacc aaagacaaga cccatctcca tcgatccaat    17700
ctcatcctcg atggattaat atactccatc cctttcgcac aggcggactg tttctccggt    17760
cgcagcagca gactgaatga atgtcccag aaaagtcacc gcggcgcgat gcaaatccca    17820
agccagccga catgggggcc atgtcgatcc atctactaga gtagtatctg ttggggatgc    17880
aaagatacgg cggggacttt gatggccatg aatgacgact cagcatcgag ggttcatcgg    17940
caaatcgacg agaactgagt tcactcattc atcgcaggac cgggggtcgt tctttgcgga    18000
accggaagag catcacatca cccgtgcctt tgttcacgat accttttact ctgttcatct    18060
gcgaaggtgg caagacagca agcaaccacc tccacctcca ccaccttcac cacctcgttg    18120
atatgtcggc agaagcagag aagcagtcct cctctccggc cgactccagc ctccagacca    18180
tccatgatga ccgcgaccaa cccccgggcg atgcggagga tccgaccctc atcacctggg    18240
atggacccga cgacccagcc aaccccaaga actggtcccg gcgcgtaaa tgggcggcga    18300 cgatggtcgt gtccggcttc aacttcatct cgccgctggc cagcgccatg atcgcccgt    18360 gtttgcccgc gctggctgcc gagctggaca tcacctcctc cgtcgagcag agcatggcgc    18420
tcagcgtctt cgtcctgggc tacgcggtcg gcccgctcgt ggtcggtccc ttgtccgagc    18480
tgtacgggcg cgtgcccgtg ttgcagacga gcaacctggt gtttctgctg ttcaacctcg    18540
cctgtggcct ggcccggacc aagggcgaga tgatcgcctt ccgcttcatc gccggcctgg    18600 gggctccgc gccccaggcc accgcggcg gcgtcctggg ggatctctgg gccaccgagg    18660
agcgtggccg cgcgctggcc ttctacagcc tggcgccgct gctggggccg gccgttgggc    18720
ccatcgcggg cggcttcgtc gcggagaata cgagctggcg ctggatcttc tacgccacca    18780
ccatctccaa cggggtcgtc atgctgctgg gcttcctcct cctgcaggag acccgggcct    18840
ccgtcctgct ggagcgcaag aagcgccgcc gcatccgtga ccggcagc aaggcgtggc    18900 ataccgagac tgataacccg gatcacaccc tgcgcaacat catcctgacc gcgctcaacc    18960
ggcccttccg cctgctcttc acccagccga tcgtgcaggt gctggccgtg tacctggcct    19020
acatctacgg catcgtgtac ttggtgctcg ccagtttccc ggatctctgg acctcccccg    19080
atcactacgg tgagtcggtc ggcatcggcg gactgaacta catcgccctc gcgtgtgggt    19140
tcttgctggg cgcctatctg tgtgcgccca cgcaggaccg gatctaccgt cggttgaagg    19200
atcgcaacgg cggcgtgggc cggccggaat accgcatccc gctgatgatc cccagtgcca    19260
tcctcgtgcc cgtcggtctt ttcatctacg gctggaccgc cgagtaccga acgttctgga    19320
tcggcccgga catcggcatc gccctgtatg ccgcgggcta catcaccagc ttccagtgcg    19380
tccaggtcta tatcgtcgac acgtacacca attatgcggc atcggcgctg gcctcggtga    19440
```

```
ccgtgctgcg cagtctctgt gccttcacct ttccgctgtt tgccccgaag atgtatgatg    19500
cgctggggta tggctgggga aactcgatgc tggccttcat cgccatgggg ctcggatggc    19560
cgggtccgtt tgtgttgtgg cgctatgggc aggctctgcg agagcgcagt ccatatgccg    19620
cagagatata attccagtca tgacagaatt cagactcaaa aacagtgtca atagtgatgg    19680 tgaaaaagg ataggcggat gtatatactc gtcaagtttc tgtcgtaata aaataaagca     19740
atggctctaa gaagaagctt cgttttggca gtctcatgca tctactggta ttgctgtatt    19800
aaagtccaac tactgagatg atataatcat gatacctgac tctggttctg gtcaataaga    19860
gagagtatat atatatattg tcgtagattc aggcacggaa gcatagtaag aaaacaacta    19920
attgcttaaa gcttgcttga ggactagaat acatggaatc taggccatat gtcgtaaaat    19980
aaggcacgga agcatagaaa gtagctgacg ctctattctg tgaaaaacag tcaaattgct    20040
cagaggacta gaatgcaccg agatctaaca gcttatttaa gctaatcata aaacaaagca    20100
acaggatcta atagcaagcg agctgtaatc aagcggggat aaatcaaaca ggttcaaaga    20160
ggccaaacgg ggtcaaaaca ccaaacgatg atgtttcggg atctagctgg cgccagcagc    20220
gaaccatgca atatgccgc ttgcgccgac aaagagtcat attgtattta ctggagtcta    20280
cagtagccaa tagcgacgca ggagttttgg acagattctg catatattct tcccattctc    20340
cctcgcatca ccgcttgatt atgaatttat ctgctccgtt cagcggtcaa gaaagtattg    20400
ttttagcatt ttatagatct tctaggattt ctgctcagta ctaaagtaag aacagcaaaa    20460
aataaaagat aaaaataaaa ataaagaaag aaagaaaaat aaagtaaaag cttaatggaa    20520
acaataataa ttagactatt cgagatatag atctatattg agtgaatttt atatcctcca    20580
ttcacacccc cagtagtcag ctgccaaaat acatatcaat gctaagttct gttagcagct    20640
acagtcgaga taacgtact gcatccgcat tcaaaccata aagataatct tctcaatgct    20700
tgaaaacaag aatttgacct ccgcccgttc tcaaggttat cgagcaggtt ccacttactg    20760
gggtcatagg aaaattaaac tgggaataaa gtaagagtaa gttcggtttc tagcgtttat    20820
catctactga aaaattgctg gcaatccgca ttcataattc ttcatcacga ctcaaaacgt    20880
taaagatgct gctcaaaaaa ctccgcggcg gtcttgtacc catcttcaaa cgccttgcgg    20940
accgtctcgt ccttcagatt ggcacgggcg ccatccagc cgtggatctg gtccggatac     21000
gactttacca ggcctgtctt gccgggaccc tcgaggacct tcttgcactc ggccaccgcg    21060
gtggcatctt cgtccttcga cgccaggatg atatggggga tgttgatctt ggagacatcg    21120
tcggccgaga gcattctgca acacccccca tggttagtgt cgattgagat ctcaaaggga    21180
aatggtcaag ggacttgccc tgggtgcgtc tggccggatg tcttgaaaat ggtcccttca    21240
cctgacgtca acgcgaccat cttgcctccc cagcagtagc cgaacgcgcc ccatttgccg    21300
ctcacgctgg gatactgcgt cgagagctgc tggacgagtt ccttcatcgg ttcgatatgc    21360
acggcaaagt tgcccgccgt ggcaaaccag tcgccaatgg cctggaccag aaatcagctg    21420
gagattcgca tacagcgttc aagtcggaca tacggccttc ttttcttcgg tgtccgggg    21480 gaaccaggac tcggaggcca ccttgcccctt gaagaagtcc gggaccacca ccagggcatt    21540
cagcgacgcc gccaggatat cggcgccctg caggagctgg ggcgagtatc caaaggcgtc    21600
gtatatcagc aaaagggcgc gagaggcgtc ggacggacca gtgatgtcta catcctccgt    21660
cagaaaagag tgttaggcgg gacatttcgc agatgtgtgt cgcaaatggg gatcggtaag    21720
tatatacgta catgtcttcg tgtccagcac cgtttcatat ctgcccttcg cttggtagtc    21780
gtcgaccacc gcgacgggca ggcagagaca ggctttgttg tgtccggaca tggtgttgag    21840
```

```
ggggagggggg agtgtcagtt tgtctccaag aagaaagcgg gggagaattg ggcactattt  21900
atctctatct gataagttag cgcccgcccc gccgatcgag ttcgagagac cgcaattggc  21960
gtaaagaatc cgttgccggc gtctatcaca tccacctatt atattggcag cggaggcttt  22020
tttcgagtcc gaatcggccc catctaggat tctacttgac tacggtatag ttatcgcatg  22080
aggggatctg cagatacagg gctgaaacaa cagtaaattt ggtactctca tttatatgat  22140
ttgttagagt catattctcc ccattcaagt catcatcggc cattttctc tcttctccct   22200
ccgccatgtc ggccctttcc tccacaccag catcagcatg gcaacaggc cgatatagac    22260
ggcgcatatc accgtcccca tccatccgat cccgatcgcc tcgacggccg gccccatcac  22320
ggccaccgcc agcgcccca tccagcaccg caccagatta ttcgccgccg tcgcggtcgc    22380
cggcgtgtcc agatgcagat cgacgatgag gaccgagatc gagttggtcg agctgctgac  22440
cgtccagccc accacgaaca gcgccaccag cggcacggcc agaggggtgc gcgcttgcat   22500
cgtccagccc tacaccagca ccgacagggc gccgaccccg acaatcggca tgccgacctg  22560
cagccgcgcc ttttcgatcg ggaactggga cagatcctgc tggcggccct ggcggaggtc  22620
caggtggtgg atgcgcgcca agcgccggaa gttccagtcg acgatgtggc cggtcgtgag   22680
ggtcgccagg aaagccccgg cgccgaaggg caggaagcac aagcccacct ggaaggtgtt  22740
gaaggcgtac tgcgccgaga gtgcctccga cagattcgcg acaccatttt ggtacccggc  22800
cagcacgcag ccggcgtaga tcaggatcag gctggtttcc cggtcggcga tcacgcggag   22860
ggatccggtc gggctggcct tgcgtccggg tcgaatggct gctggactcg tggagatggt  22920
catcgggggg ccgtttaggg gtatttgtcg tcggtgtcga tatgccagcc aggacatatg    22980
gatccaggtg ggaggggaa tcgagccatc tcccacgacg cgcgacagg tctcgggcag   23040
gcaggcgagc atgaggagaa agacgacgcc cgcgaagatg gccaggaacc aaaagaccga   23100
ccgccagcca aacgactgga tcagcatgcc tccgatcaac ggtcccacag ccgggcccag   23160
gatggccccg gaggtgacat agctgatata acggcctcgt tcggcggagg tcgccatgtc  23220
cgcaacgact gcctgggcca gggacaccaa cggactgctg cccgcgctct ggaccattcg   23280
caggatcagt aaagccacgt agttggtctg gagggccagt ccaatgttgg atccaatgta   23340
gatgacgaag cacgcgatgt agagcggccg tcgccccgct cgatcggacc agctcccaat  23400
gaaggagggc gccagccctt gcatgacctg ggaagtcgg tcagcgggag aacaatagag    23460
ggatcatgta gggtcctacg ttaccagata cgtggtcacg gtgaggttga tcaacgagac  23520
agacactccg agggcatcgg ccaaggtgcc cagcgccggg aagtaaatgg ccgacgaaac  23580
cggggagaag aaggcagcca gggaggcgat gatgacgatc aggatctttt gtggccgtgt  23640
gaaaatgcta tgtgctttca gctcatcttg gggtggcttg aagtctggga cgatggcccc  23700
ctgggatgat tttgggcact ggtcctcccc gagaagggga gtggtctcgc tggcggaggg  23760
catggcgaag cgcctcaggg cagatgtcaa caatagatac actgcgggcg atacttggag  23820
ctgttgatcg attctttata tagactagag tagggagcag tagtccaagg agccacgctg  23880
ataacaggac tcgtggtaca tccccagagc tgattcagtt ttccaatgga atacaatcaa  23940
tggggcttga ttatttgtgg gtttctctac ttttagtggg ttggaattta atcttctgcc  24000
ggtcaggggc cgttgattca tttcggccaa ttaagtgtct tcaatcatcc ccagcttcgg  24060
agggttttga tctcgtgcaa tatcagaccg cgggaggttc ctgttttaat cagttcttct  24120
tatctatttt ttttttttgt ctctcaattg atgacttcat cgcttgagta aaataaagta  24180
```

```
gtacttttct cgcttatttt atgttaatct ttcatgtcag atcgtatatt gatattcact   24240
acacacaatc tgcttctccg ttaccgtata gacagatata aacaaatggg ttgaccctgt   24300
atgcatcatg aacctcgtca gtctctttct caccgtcgcc ttcatcccct ctgcattggc   24360
ccagtcgtac tatccacccg taccggccgg caccaccgtg gtcaactcga cccagtatcc   24420
caatgcgagc attgagtaca aagaggtgag atttccatgc cttctggatc tcgtaggtac   24480
ttaaagttgg tgtctataga ccacgatctg cgagaccacc cccggagtca agggtacag    24540 cggatatgtc cggctcccca gcgatgttgt gaacagcgtg aatggaccgc acacgtccaa   24600
ttacttcttc tggttcttcg aggcgcgtca cgatccggac aaggctcccc tggccatcta   24660
tctcgacggc ggaccggggt tgagctcgct gcaggggggct ttcaccgaga cgggaccctg   24720
ctatgtcaac gaggactcca acagcacccg actcaatccg tggtcgtgga ataaccatgt   24780
caacatgctc tacattgacc agcccctgtc cacgggcttt tcctatgata ttctggtgaa   24840
tggcacgttc gactcgctac gcgacaaaca gccggccacc gagcactcga tcaaccctct   24900
ggctgacgag gacgagcctg tggccaacaa cacctatttt gttgggacct tctcggggca   24960
gaaccccggt gagacggcca actctaccgc caacggcgcg gtgggcattt ggacctttt    25020 gcaaacttgg ctctccgagt acgcctgtct tcgagggtaa ctttcgcaac gacagctgac   25080
gtatgggatc agatttccgg aatatcggac gaaggatgat cgaatcagtc tatgggtga    25140 agcggtgagt gactgatttg gaagtctaat tgcagaccag tgcggcgtct ctgacgtta    25200 tgcatataaa catgaagttt gccgggcaat tcgctaccat ctacgccgag tactttgaag   25260
tccaaaatga gcggattcga aatggcagcc ttcgacgcga ttccaactcg cccgagagtc   25320
cccggatcat ccccgtggac accgtcgggc tcatcaacgg ttggatagac atgtttcgcc   25380
aggccgccgg ctacctaacc ctcccccttca acaacaccta cggactgcag gtggccaatg   25440
cgagcgttca gcgtcagatc acggacgcgt actaccggcc gggcggatgc gtggaccaga   25500
cgcagaaatg ccagacggcc gccgcagagt cagatccgaa gaatcgcgcg cacaacgcga   25560
cggtcaatga gctctgcttc cagtccgcct acctctgcac gaccaccgtc cgaggtccca   25620
ttgcggcgac acaggtatgt tgcgaggagc aagaggtcac ggcacagaac tgactgggga   25680
gcagtacaat acgttcgaca tgggccattg gaaccccgat ccatttcccc cgagctatta   25740
cattggctat ctcaaccaac gctgggtcca ggaggctctg ggagtccccc tcaactttac   25800
cgcacactca tcgttggtca ccatgtgtat gtgtctcccc agcggttatc gaaagctcta   25860
cacaaggctc acaggccagt agcattcctc aaaagcggcg cgtttgccct cccctgggcg   25920
cttcaggatc tgggaaagct tctcgatcgc ggggtgcagg tgacgatgat gtacggtgat   25980
cgtgatatgg acgtgagctg taagtattcc ctttctttgt gcaatgaatt ggtaattgat   26040
gggagtcaat agggatcggt ggtgaggaag tcagcctggc catcgatcat tcctcggccg   26100
cggaattcgc cgccagtgga tatgagagta tctccgtcaa tgcaggctat atcgcggcg    26160 taacacggca atatgggcga ctgtccttt cccgcgtctt tgaagcagcg aatagaggta    26220
ttcattccca ccgtgctatc tcatactgtt cactatgctg atggcgatgg cggccaaatc   26280
gcagtgccct cgtaccaacc ggaaaccgcc tatcaaatct tcatgcgcgc catctttggg   26340
aaggacatcg ccaccgggtc gacagtcgtc gatgcccgct atgcctcgac cgggccatca   26400
tccagcgggc atatccgcaa cggactgccc gtggccccgc ccccgagtg ctatatctgg    26460 gccccggcga catgcacgcc ggcgcagctg aagtcactcg gggacgggtc ggcggtcgtc   26520
cgtgattata ttgtggtcga gtggtgagca ttcaagaggt atcaatgaaa cgtcattatc   26580
```

```
attatcaata agaagcatat atatacatga cttcaggcag ctacatgtat atatacatca   26640
gtcttcgtgt atatatatca gggtcatgat gagactggcg cgtaagtgaa aataatcaca   26700
aggttaatag aaagtcatgc ctcatattca aggtcttcca atccagtctt tacccttgcc   26760
acagctccag ccggccgatg accgactgca ggcgtcgacg attctccgac accagattga   26820
accccgtctg tgagatggac gtctgcggcg cctggagcat gcgctgctgc agctgctgca   26880
agaccgagga gagccggcgc aggcgcttgc agagaaactg cttgaagaaa tggatcttct   26940
cttcggcttg gatctcgaac gcgcccgcca acagccgccg gctgttcatg agccccgaca   27000
gactgttgtt cgacgcccga acccctgac tgctgccgcc gctgctgacg ctggcgctgt    27060
cgcacgcgcc acacgacgac cgccgggaac cagccaggag cgaggaggcg gcgcccgggc   27120
ggatgagcgt cagattgaac ttggacacgc tctccagcat gcccacggtg ttgtcgatct   27180
tcagcgccac cagcaggagg aggtccgggc gactgccgga acatccctgg cactgcagga   27240
cctgcgccgc ctgccggtgg gcgctctgct ccagggccac gagcatgtcg atcgagcacg   27300
ccagtcccag cgaggtgcgg cgatcgaaat cccccaggct ggccagcacc gactgatagc   27360
attcgcagtg ccgggccggc ggcgccgatg ggagacgctg cggcctcggc gccgaccccct  27420 cgggatggct gtccgccggc atggacatcg ggtagccgac ccctggctcc tccggggccg   27480
gcggaggcag tccggggccc gccgacgact cgaagggcgg agggttctcg aggaacagga   27540
aggcatcccc catcggagcc gccgccgatt tgaacgattc aaggaaggat gggggctcgg   27600
tgccgggcgg acaggggccc tggtcactgg gggccatgga cgcaccggcg gtcattccgc   27660
tcagcgtcgg cccgtcgaag tccaggatag actccagatc gaatgcgggg ggtcccgagg   27720
ggtcccccgc ggggtcatga ttcgagccat ccatctccag ccaggcgtcg tcatccatcc   27780
tggcggcggc ggccgggccg tgcccgagca gaaaggcatg atcgtatgag gaggaagacg   27840
agaaggaatc gaccgcacgg tggctgatgg agatggatgc cgtcgtcggg ggcaatggag   27900
gctcggcggg actgccttcg gaggcgtgtg tggacgccgt gttgttgccc tggaaggcac   27960
ggtttttgct cctcttgggg gtcttctctc tctcggccgc gtcgccgggg ggtttccgcc   28020
gcggcggacg tccaatgcgt cgcagggcac tgtacacga gggaactttg ttgtacttgc    28080
agtgttggca cggctgttcg cgcgagcacc gatgtttggc cttctggcag gcgtcacacg   28140
tggagcgcag tttcaccggc tcgccgggct tgcttgccgt ttcgccaggg ctgggcggat   28200
gtgggaagga tgaggatggc atggacggcg gagaaagagc cgactctaca taggatggat   28260
gttggtagat actcgggtgt ggattggaag gctggatcgt acgatccggc aagctacata   28320
ctagtattgc tgacgagaga aacgcagaag agatatagtt aacacggata aaagagaacc   28380
tcgataaccc tcaatcgcag taccccccgca tgttccccgc ctctcatctt cacgattggc   28440
ccagccagtt gggggctgaa aggagtcatt gacgtcaatt ctgcatgctc tacatgctgg   28500
aaggattcgg cgtcagctgc agatcgcata aactggttgt gtagcatcca tcacatactt   28560
aaaaagcagt ccagacacaa caaacgcagt aagaaggtaa gaagagtgtg tatcaattcc   28620
cctccgggca gtggccaggc cctcttcgga gtgtctccga cagtaaccca tccgggtaag   28680
agataagctt catcggacct aataggtgaa gtatatctaa aacacggctc tgtcgatctc   28740
gcgaaaagcc cgcggtgggt tttgaggctg gtttcggcca cgcaatcctc aacgaatctc   28800
ttgttggcca agagccatta gttcccacca aattcctcag atgtcaccta aaccttgatt   28860
atttcctcag atgccatcct gcacgctcct ggtatgatcc acctgtattc ggacagtaag   28920
```

```
agggctcgat gtggttttat gcaataaaca agcctttcat catttgctat actgaaatag    28980
cttaaaagga ggccattgac tctttataaa gatcagtatt ttattactcc tttttcgaat    29040
aggggttgtt tcagcttcta gtagctgtac ttaaatataa aaaaatacat gatttttagag   29100
ttgtctgcac agacgtacat acctcctgta cgataacagc gattattccc cgattcggca    29160
tatcaaaaac gcgcggcacg ggggaattta atttgggttt gggtggtatc cggggaacca    29220
ggcgcattgg ttcgtcgtgt taggagctcc gccgatcagc gggagtctcg gacgataggc    29280
aggggggcggt agtgcttaca gtcttcatgg acatgtagtg acgagtgtgc caagcaccac   29340
agctatataa acatactttt ggcccccctac tgggttcttg cagactcctc tccgcagaag   29400
cttgttcggc cccggaatca tattccccgt cctttgttgg cagatcgacc cggtccaggc    29460
atatatatcg gtgccaaaaa gaccccgaag gccccgatgt tgaccaaaaa ggattttagg    29520
tgcagccagc cacttccgcc catgtatccg ttggtaattg ctagcggaag gagtccacga    29580
cgcaagagca gtggatcagg ttgatcatgg ctgattatcg ccaattatca atggaaaaga    29640
atcctgctgg tcaattgcct ccattgtctt cggatatgag ccggtgcggc gtgttttttct  29700
gcacacaaat catgccgaat catctctggc gaactcgatg attccgtgat gcattatctt    29760
gtttctccaa caccacaaga aatcgccgct ctgcgccgag atataatctc tgaaccggcg    29820
tccgagtatc cgaatggata ggtaactcac ctccagtcct tacagagaca tcctctggcg    29880
gatacctcc acaatgcatt tcaatcttct cctcgtcttg accgtcctcc tccgccaggc     29940
tacggcactc gtcctgccgc cgtccaacag cacctccaat tcgaccggca aattctccgc    30000
ccgcaccgtc ttccagttcc cccagggata ctggctggag aatctggccg tccggggcaa    30060
tggccaggtc ctcgcaacca cctacatgcc gtcggccggc ctgtatctca tcgaccccac    30120
tcccaatgcc agctatcccg cggtcctcgt ccaccagttc gagaactcga cctcggccct    30180
gggcatcgtg gaggcggagg ggacagagcc cgacaccttc tatctggcga cgctgaactt    30240
ctccgccgcg gacggcttcg tccccgcac agccaggtc tggcgagtgg acatgtcctc     30300
gttccactac tcaccccaga ccgggcaggt ctccgggaag gcggccgtct cgcatgttac    30360
gacgctgtcg tcggtgggca tggccaacgg tatgaccctg ctggctccgg actcgtcgca    30420
catcctgatc gcggactccc ttcggggcgc catctgggac ctggacaccg gacgggcca    30480
ctatggcctc tcgtcgtcct tccccgccat gcggtccgac aatccggcgc gccgcttcct   30540
cgggatcgac ggagtcaagg tgcaccaggg cagcctgtat ttcaacaatg cgggtgaatt    30600
caccctcgcc cgcatgccca tccacagcga tggcatcgcc aagggggagc cggtcgtcct    30660
ggccacggac ctctacagcg atgggttctg tctgtacgac gccgacacgg tgctggtgac    30720
gatgaacatc gacaacggcc tcgccgcgct ggacctggag agccatcgcc ggtggatggt    30780
ggccggcaac atgcccgacg gggtctttac gactccaacg tcggtcgagc tgggccgcgg    30840
ggaggacgcg gcaaactcg cctacgtgac catgggaggc acctacgtgg cgaccggtgc    30900
cgaggatctc gtcgggggca gcttagtcgt ggtggacctg aagtcggcca cgaccgatcc    30960
gaaaggaacg ggaagaggtg ggctgctggt gcaggagaca gagacgattt ggttggagct    31020
gtagagaggg ggttcagtgc tagaacattc agatgtactc gagtagtggt ttatcatctt    31080
gaaaatagca agctgtctac tcatatatgt agtccagtat agggagagtt taaagaatgg    31140
gagatatcat tattaaaact gaacgatacc agatacaaaa aatcattttg acccaaagtg    31200
catcaaggta cgtcgacgtg ttcctatata catgttccta tacacatggg tcgcccgtag    31260
gcactggaaa tacaaatttc acctctggcc tgaaagaccc taagaaggaa aaatcatata    31320
```

```
cagagttttc cgccctataa ataataccct aaaggagctt tcaagatgtg tccaaacaca   31380
gtacccatcc cctgctggtc atagcttcgc cgacggcgcc gtcatctcga gcactggttc   31440
ggtctccccc gtgtagacgt gcgtgggccg gaagaggcgg attttgtttt tcactgcggg   31500
cattttatca gctctcttgc ccttgcttga agttggaaaa tcggctggac ctacacatgg   31560
actcccgata atgcgccagg atgcccacca accgctgtgc taccattgca accgggattt   31620
cctccggttg gaatccccta cgacccgacc ggtcaattgt catccactgc aatcaacaga   31680
aaaacaactt acaggcgatt aaagaaaaag gttccgtaaa agtccgcgtt cgcatgcagt   31740
tttcgtttga tgaaatactc atcggtcgac gagaggcgat cgatctcccg cgccaccttg   31800
accagcggat ccgagtcccc gtccagctcg ctgaagagca tatctttgat gggcttcacc   31860 cggggtcga tcgtcgtgta cgtgcgatgg ccgtacccaa acagccgccg cttgccagac   31920
ttgacctcct ccagaaaagc cggcacctgg tcgacgctgc cgaccgcttg gatggttttg   31980
tattccgcct ccggggcgcc aaagtgcagg ggcccgtacg cagccaccag ggagctgatg   32040
aggcccgaga tgggatccgt cagcgaggag gcggttacca ccatcgcaaa cgaggacagc   32100
gccatgccgt gctcggagtt gagcgccgca accgccgga agcaggacag cttcaccggg   32160
tctggacgac cggtgtacgg ttcaaccagg cccatcatga tgaacaggtt ctcaaagtag   32220
gtgttatccg tcgtggccgg cgtgaaggcg atgccgcgac ggtggctggc cgccatgccc   32280
atcaccaccg cgtaggcggc tgccgtccgg agaatggcac ggtcagtctg ttcgggattt   32340
ccatggtaga tgttgccccc ggcacaggct gggatggagt cggcatggtg ggccagatac   32400
gcggacagcc cggccacaat catgggcatc gggggcttg tcggactgca gggggttcag   32460
ttcttcattc attcaaggtg atcgtgatgg acgatgaaaa gcacagtaga agacctacgg   32520
gaatgtctca atcacctccg cgacatgttt gggcgtggtc gacatgagcg tggccaaggt   32580
cagacgcaac gcctctcgct gagacggcgt gggatatttg ccccagacca agagatgcag   32640
catgtcctcg aactcggcct gccatagttg ctccagggca tagccccgaa aaagcaacag   32700
cccgcgatgt ccgtccctaa attgagcatt agtgaaataa agaaccttcc cccggggggg   32760
aactctcttg gacccgttcc ctacgtatat gtcatgttgg tctccaccac gcaggtgttc   32820
ttgagacccg gatcaaagac ccgcaggcca tcgcccactt tgtccgctcg atccgcgccc   32880
accggggacg ccttgatctg cttgagatcg gtggcgagga cggtgttgcg ccggatgggg   32940
atctcatact cccgcgatgt gcgggagtct cggatatgta gagctccatg cgacatggtg   33000
aagctgcatt catgatggat gcatgctgca ttacaatttc tatatatatt cgacagatga   33060
tattcctcgt ttatccccag gaattggtgg aagcctccgt gttcatcatt atcggggagt   33120
tctcgtgatg tgatttccta atgccacatg ttccaatcct gtgaatgccc ggaatgttga   33180
ctctgccaat gagaaaatcg ccgccagcgt ttcaatggtg gcccgggatg tagaagagca   33240
tttgaaatct cggcatttcc tttccccaag aaaaagaccg agtccgccgg gttctttttc   33300
gaaggaatgt gagcattgct gctgccggtt cccaggtttc tctgcaaaga ccctttcttt   33360
atactatctg gaagaaatag tacgatctgt tgtttctctg atgtgatctg tagctttgga   33420
acctaaatat tcaagaagaa agaaaaaaga attaccttct ttttctctgc cttctactgc   33480
cttcctgcgt agtctttctt tccttttttgc agtgagtttg ctaaatattc ccgggatatg   33540
tttccgttac ggaacgagga cgaaatacgt ggctttacga accaacatga aaaaggaact   33600
ccgaggttga cggcaccaaa tttccctcgt gacagtgcga taattatttc agtgagcatc   33660
```

```
aatacggaga aatagaccca tgccaagtac aagtgtagtt tttaagcgaa atcaatgcta   33720
ttccggtaat ctctacttta tagacaaaac aaacagcaca aatacaccat atactcacag   33780
gagcgtcaaa gatcgaagtc aacagcatac tcagtacttg atagggaatg aatacaacat   33840
cttttcagcc gacctttgac gtagcgtcat tatggctctc tatattctat tcaccttttt   33900
attttccgct aacaatactt gaagctggca ttcatcgtct aggcttgact agcttatacc   33960
atacgaaacc agatctatcg acttttagat atcagtatga ggaaatcaaa agcaaagaaa   34020
agtaaagtct caattgtttt tactattaaa ctgttcttta ccaggtagcc ttttgcaagt   34080
gatcatcaga ttcaacaccc gtggttcttg atatctagcc atgacttgag aaaaatatca   34140
gcacgctagt ctccatctga tacgtaagtc cctttagact agggatttgt tgaaccttct   34200
gttactgaag gcaagtaaat cgcggatgat ggatctgttt tggtcaacat agaatggtat   34260
gttcgctcac tccaggctga aaaccagact ctactgctct cgagaccagg cccactattc   34320
aatcgtcaag aacctccggt cccatttatc tgaggatcaa atgcagtagc aacagacgac   34380
ggcagtgtgg gagtttcaga gagttctgat cattgtcctg ctagcctggc tgctgatgct   34440
gtagacggat gagtctggtc gaggtcatgc ccacacctcc atatcagcac gatatagtga   34500
ccgcggaggg atactttagg tccctaactc cgttcaggtc cgagagggcc tccgcatgac   34560
gccgtcgata tcaagtcacc gttccctcct cattgcccat cctagggtcc ccgatataag   34620
ggcaacgagc ggtcagtaga ctctatagag ttcagccatc cactactttc tctacatcca   34680
caacatcccc atcgagtatt ccatcatggc ctccaaggaa actttcagca aatacccctgc  34740 cttccccgac aacatcccca cggcggcggt ccccaagatc tccctccgcc agattttgtc   34800
ccgcgacccc accgtgtcga agcgtctggt cgacgcgggc aaggaattcg gctgcttcaa   34860
ggtcgacctg accgatgcca tcgacggccc tgtcctctgt cagggcgtcg agcgcggctt   34920
tgacctgggc aaggccttct tcgaccaaga catcgagacc aagaaggcat acaagctgag   34980
tcacgagaac gtcgggtagg tttctcccca gccgacgtcg gcccagatga tactcaccca   35040
cgggtgcaca ggtacaagca ggccggcgtt ctggtcatta ccaaggagcg gcgagaccag   35100
gtcgagacat gctccgtctc gcgcgatgat ctggcggcca gccgacccga cctgccctct   35160
gtgttcgacc agcagcggct gctgctccag ggcctcgttg cgcagctcgg gcagctctcg   35220
cacctggccg tctaccatct gtcggagggt ctggggctgg attatggagt cgtgtcggcg   35280
cgccatgatc cccgcgacca gtccgccacg atgatccgtt tcctgcataa tccgccgcag   35340
agaggaccgc gcgaggagct gccctcgacc gaggacccgg gttcgcgggc ctacctgatg   35400
ggccacagcg acgggggcac ggtgaccatc ctgttcaacg tcctgggtgg actgcagctc   35460
cagcgccagc agcccgatgg ctccatcgag tggcagtaca ttccgcccga gcccggctgt   35520
gccttgatca tggtgggcga cgccttcaag tccttcacgg acggggaagt cccctcgtgc   35580
gtgcaccggg tcatccagcc gccgggcgag caggatcgct tcgatcggta tgcgctgggc   35640
ttcttcctca gcccgccaa cggggcctcc attggaccag tgccgcgccg gggcgtgacg   35700
gagaatggcg tcaacaaggc gtcggactat ggagagtggg caaagaacaa gaacgcggcg   35760
ttgtacaacg agatgcgcca ggagaatgtg gcaatttaga tgagccagac ccgacttgaa   35820
gcgatagagt gatgtagtaa gaggggagaa agacaatgat gcgttaaacg taactgagat   35880 gtctacccctt ttgtctagaa gtaggcctgt ggcattcaag acggatgttg tctgtagttt   35940
tgtctcggaa agtatgaaca cgctaatcgc cctattatct tcggattagc tgcactcggg   36000
aaattcccga cctcaaactt tcagcggcat ttatcctggc ataagaatat ccagcaacac   36060
```

```
tatcatgagg tatagtctga cttgcagaat gccaatgacg gtatctagca agtacagaaa   36120
aggtacgatt gggaaaacca ccgatattgt gacgccgcgg tctcaccgtt gaacagcgga   36180
atcctccacg cctacgaaaa gccccttgcc ggagggttgg tcgagcgcga cagggtatag   36240
cgagggatag gcgccttaat tgaatccact accgagcctt ttagctagac ccaggcttct   36300
tcaaacccag cttcttgtgt agctgtacgg agacgcttct cctggtcaac atcatgtcca   36360
gtctgccttt ctagctgctt caccaaaagc atccttgatg gcattgttaa atggcaattc   36420
gtgaggtcat tttctgcagt tactgcgatg cggatctggt gtgttataag atggtctctc   36480
gaaatcgtac agaggccggt gtacctgcat aggaggtaca gtgcttgcag tagtaaatct   36540
cttgcttatg cttgtttctc gttgcatgct cactctcctt tggtggctgt gtatgctgcc   36600
atcagagatc attggagtgt ttcttttgc gaaaaggctc agcaggttca acagaagatg    36660
caggttcggt tcctgggctt tcagtaacca cagtacggtt agagaccaag ccaacaagat   36720
cgaatttagc ataggaagta gtgttggacc ttgtgttaat atgtggcaaa caatggaatt   36780
gggccttttc aatgtagaag agcggaggtg aggggtaaag tcaacaacaa gttaacaact   36840
attgtagtga aagtagactt gttcgtgggg cgggtccggt ccggtcaggc gaaccgaagt   36900
taccgaacct tcttttaacc cggccaagtc agctcaagac ctggatgggc aattctctaa   36960
cctaatctag aaagaatctc tagggtcccg aggtcgggtc ggatcaaagg ggcggatcac   37020
cgattttgac gccgcgtccc gagccgggt cgggttaaca agtgtaaatt gttaaaccta    37080
aaattgaaac agattataac agaagaagag aaatccttca tagcccttttt agcattgaga   37140 tagcggtcgg ctggatggtc cgggcttgca tctatcttga gggcctgagg cgtcaatcct   37200
aacttgtgcc gctactggca gtacgcgaag gtccttcgga tctttcggag gggacgaatc   37260
tactctatgt ttattcactt cccggaatta ttcggatgag acactctacg tacgaccgta   37320
tcctttgtca ctataattag catatggaga aagaaaatc agatacaagg ggtgtaattc    37380
gtcatgcttc atccgtcatt gattcaacta tctcataaca agtctacaaa cagggtctac   37440
ccatctctct cggcatctct tttttctcgc catcctgcgc caaacccata cacaagcccg   37500
ctcagaggca gagatatcac gtagatggca cccaccacgc agaaacacca ttgtcggccc   37560
agaagatcca ggaggggcgt gacgcccgcc gtggctcccg ccccgagtaa gcagcgcacc   37620
aggttgtttg cggcggtcgc tgtggccggc tttccgtaat ggagatctac aatcagcacg   37680
ttcatgacat tgtagctcgc cgtgacgaga tatccgatca aaggagcat ggccagcgcc    37740 tccacgatgg ggcgttcggc cgcgatcacc cagccgtaga gggcaatcga gcggccgcc    37800 agcatcgctg acggcatggc aatctgcagc cgtgcgcgct caatgggaaa ctgccggaga   37860
tcctgcttcc cgttgcggat cggcagctgt ccgacctggc gggcgatgcg ttggaagttc   37920
cagtcgacga gccatccgtt ggtgaaggcc gacaggatgg tgcccaaccc aatgggaata   37980
taggtgagtc cgagctggaa gtcgttgaga tggtaaatct cgttccactg cgtcggcacc   38040
gtcgaggtga cggcgtaata ggccgcgtat ccgattccat tgctcagaag gaccaacccc   38100
gttggcattt caaagagcag acgcagccgtg ctccaggggt tgggcacacg gatccgcgac   38160
ttttggtgtg gcttgggagg agcattatca gcttccggcg acagatttag ctgttgcttc   38220
cctcgagtcc gtccgaccat acagtcgagc agagagcgat tccaccgagg aggtggaatg   38280
gacccattgc ccacgatcgc acggcaggtc tcggggaaga acagcatcaa aagcacgaaa   38340
aagacggcag ccacgagcgc cagaaaccag aagatagacc gccatccgag ggattgactc   38400
```

```
aagagaccgc ctagggttgg ccccagcgcg ggtcccagga ttcccccgag agaggcgatg   38460
cccaaataca tcccccgctc ggcggacgtc acggtgtcgg ccgcaacggc gttggatagc   38520
gcgacagtgg cgctgatgcc ggtactttgc agggcccgca gcaccagaag agtcacaaaa   38580
tctcgttgca gagctaagcc gatgttggct acgatataga tgccaagca gaggacatat    38640 accggccgtc ggccggccgt atccgagaga tctcccataa aggcgggggt tagcccttga   38700
aaaacctgta gtgttgatca ggaactgtct cgagagccgt gagaaagtat gacaaagcat   38760
acgagcttac catataggcc gtgatggtta ggttgaccat tccgggactg atcttcaact   38820
catcggcaat ggagttgata gccgggtagt agatattgga tgagagaggc gaaaaggtcg   38880
aggccaaggc tgccgtgaag acaatgagct tcttctgcac tggggaaaac accgagtaag   38940
gcggttgcgg cggtgcaaga agagcagtgg cttcgtcgac ggtgacccgg gggatgggga   39000
tcttggtgga tgaagccatg acagagtgca ttgaacctgg gcaaagcctg agggagccct   39060
gtacaatctg atccaagaat attaaatgat cccccatgat cagtgtcaac caagcggata   39120
agaagcggtc cgccgcaatt tataaatcct ccgcggtgca tttcgtgccc gccacaaagc   39180
tcgactccgt ggggactttg accatggctc aacacgacaa catgatgaaa tcggccaatt   39240
ccaagcattt tcgacgaaag ctgcgatttc ctccagccgg gaccggcttg tggtcgacag   39300
ataacagagt ccaaccccccc gagaagacga tatagattgc gggttctcac ttcctcactc   39360
acgctcatct cccacgacaa cttgaaccac acactctcac acactcagac atcatggtgg   39420
cgacaaagct tttctccacg gctctggtgg ccgccgccct ggtgttaccg ggctctgcgc   39480
tcagcataat ccccttccag aagcccatgg agaatccgca cctgtgtgat ggcaccggca   39540
tcgtggaccc cgacggcaac tgcaacgggg acggtgtcat tgatgagcct cccgcacgtc   39600
caccacgctt cggaaaccca ccgccgcacg agggcaggga cagggatggg ttcaagttcg   39660
agaacccctc cacccagtgc aagtacatgt cgcagccgga cctctgggac aacttcaagt   39720
cgctagagaa ggacatgagc aagatcttta ccatgatcca caaggacgtc gattttacca   39780
tcgtcggtca ccatcccggt gctgggcact acaccgacct gctgcacttc tacaccaatg   39840
ccctgcgtcg ctacagcgtc tgcttctccc agtaccccga gtatttccgc atctatcccc   39900
aggccatcca cggaggctgc aatagcgagt ggtccgtcca ggagattctc ttcctcggcc   39960
gtaccaacca cggtaagcaa ccctgattga gtatccaaag ggaaatagag ctaacggtgg   40020
ataggcgtcg actttgatgt gatcaacgta tgggtcaccc gctggaagga cggccagatg   40080
gtcgaggtcc gcacctacat cgactccatg cgcatgactg gcttgctcca tgagaacgag   40140
ctctggtgga actccagcac ctacgaggag catcccaact acatcccggg cccaacgggt   40200
ttgccagacc tcgacgagct gcgcggtctg atgcgcaagc cggatggaag caggtacgac   40260
gacatgtaga gagtgtcacg gagtaaggtc gtgatggatc aacgctgcta aatgatggac   40320
gatgtgcaag aattggaaac gaaatattgt agatggattt cgctcgttgc tgttgttgct   40380
gattgccatg ttttgttcgt tgatatagtt gagtaaccag actgagatgg atgagttggg   40440
gtatatgttg gtgtacatag gtcaaccgac ctccctcatt taatatggcc cttgcactag   40500
gcctgactgt cctgagaatg ctgtctttac tttattagat attataaata acattttatt   40560
atattctaag cttcctaaac attgaaacct caaatattaa atattctaaa gatcctaact   40620
tccctaaaat agcctaatcc cctaattcta accccttaat ttctaacatt gagatatgtg   40680
gcaagaatcc gaaagatcta agacttaaaa taacagaatg gtattactgt tttatacaaa   40740
gtccggtcta gagcacaggc cacattaaat gcggggagaa ttaggccaag aaatcagcga   40800
```

```
ggtcgcctgg tataggttga aactcgcgtg agctagattt gaccacagcc gaattgcacc    40860
atagttacat ttcgagtata cctctagaac gccatatcca agcccttatt ttttgtcaaa    40920
ttgcaaaaga gtggtatata catcgaaaaa aagacatgtg cgttgatcac aactggagtc    40980
ttaaagcttc acttcagacc ggggacggac aaagagatcc acaaacccag aaatccccag    41040
agactcctcc tccaccgccg cctccatccg cgagatttct tccgtggaaa acatcagact    41100
cagattcctc cggacctttt cacgaccgt cgtgaacgtc tgcggatgct tgctgtgccc     41160
gactgggaag tggaccagaa tctcgtcgag caccgtgcca tcgatcaggc gcaccgtcat    41220
tcccgacgcc agactcttca cgtcgagatc cagataatcg cgcgtcagtt gctcatctgg    41280
ttgaatctgg atcttctcgc gcagtgcagt gatggctcgg cttgacgacc agacactgtc    41340
atcctggtag tcacggactt cgggcatcgc ccccttgagg aacgccaggc tcacgatgta    41400
ctgcagacaa tgatcccggt ccgcggcgtt ggacagcggg ccccgtttgt tgatgatcat    41460
gtcggccgcg gcattggtcc tgatctcgat acagtcaata tccttctcgg gatgcttcat    41520
gcctcgcgcc tgcatcgctg cccgatgacg gagcgccgcc tcgaccgacg acagtgcgtg    41580
gccctcgacg ggcatgacct tgaaaatgat gttctccatc acccaactgc cgtatggctg    41640
cggcaggtcg aaggtcttat ttccgaacga ggtggcatag aatccccacc ggggcatcgt    41700
caacggggtc ggggagcccg gttgtcccgc gcgagtcagc aaggccagat gcgtggcctt    41760
catacaggca tcaccggcgg cccagcccct gcgcgggatg gtattactgc cagagcgata    41820
gacgcgcagg ggatgaccgt ccatccagac ctgcgagata gccgccatcg tctgcgtctc    41880
ggacaggcca aggagccatg ccacgacggc cgtcgaggcc agcttgacca gcacgacatg    41940
gtccagaccg tgtgaatgaa aggcattctg gagcagcatg caccccctgga tttcataggc    42000 cttgatcagc gccgtcagca atgtacgcat cgtcaatggg ggcccagtgt gcacgatgcg    42060
gcagctggcg acggatcgac acagccagtc actgacggcc aggatcgccc cgagattatc    42120
tgcccggacc atgtcagcga ctgtcctcgg cttctttgtt tcgaaaagaa gaaatggaaa    42180
gagtataccc gacggatgtc cccagtctgc ccccgcgatg gcatcattat ggtccagata    42240
tcgcaccgcc gtggccatgt cgaacgagcc tttcaagggg tccaagacat aggaggtccc    42300
gggcatgtgg aagccatagg gagtcaccgt gtcgggaacg atggggccaa agaatcgcct    42360
acaatcggca ctcagagcga cagtctcgat ggcacagccc atggcatcca gaagagccac    42420
gcgggcggtg gtccatgcct gcggggagtg gatatcatag tggaagacat agtctttgat    42480
atccacaatg acctggtcgt acgcttgcat tttgctcact gattctttgg tgggcaatgg    42540
agttcaatgg ctggatactg caatgataag gaatgctgtg tcgttacgaa cttacgacta    42600
taggacatga gcagaaaacc cccgcgacgg acgaagcatc attcaggcac agggcaggct    42660
tgaagattaa gcatcagttt cacgtgcttg acaactaagg cgagtcatct acatttgata    42720
ttccgaaagt gtaaagagaa gtcttttttgc acggagagaa tctctgaatt ggtcactgga    42780
cagaaagtca ccgcagcaga aacttgccgc aacccagggc tcaggatgcg gctctaacgg    42840
cctccacctc acctcgtctg tccaggctga tgggctcatt cagatcgatt gactatataa    42900
ccgcggaaac tgtgcgcggt ccagcattcg tctggaccag catcttccta ccgggttcac    42960
tacctccacc accaccaccg acaccacatt cacaatgccg gtgagatttc tttgtctgca    43020
tggctggggc accaatatcc aggttcgtgc gatgaccgaa agtaatccaa tggctcgcgc    43080
ctcgagtgac tgaccataat ttatctggca gatcttacag tcccaactcg gtagacaccg    43140
```

| | |
|---|---|
| cagccctaca aaagaaaaaa caaaaaaaaa cccctaacc gtgaacaggc ccctaatgc | 43200 |
| gagagctgca gaaagacaac agcgcggaat tcatttcat ccagggcgat gtcgaggcag | 43260 |
| atcccggccc aggtatcgag ggcttctacg aagggcccta ctacagcttc taccaattcc | 43320 |
| cccggacttt ccccgacagt gatgacgagg aggacgatgg cggagatgcg tccatgttcg | 43380 |
| aggcctatga tgatgatctac gacatcatag ccgaggaggg tccttttgac ggcatcctcg | 43440 |
| gcttctctca cggcggcacc ttggcctcgg gcttcctcat ccatcacagt aagacctccc | 43500 |
| cttatacgcc gcccccttc cgatgcgccg tgtttttcaa ttcactgccg ccgttccgca | 43560 |
| tggatcccgg cgaggagctt gtcgtggatg atgatctggc ccggcacctc acgataccga | 43620 |
| ccctcagcat tgcggggacg cgggactttg tctacaagca gtctctgatg ctgcaccagt | 43680 |
| tgtgcgatga gaagtcgtcg cagctgatcc tgcatggaaa gggccacgag atcccggggg | 43740 |
| atgcggcgac ggtggcgcgg atggctaagg catttcgggc actgtgtttg cgggccatgt | 43800 |
| atttgtagat tgttaataaa tcgacccatt gattcgatgt acagagctgt gaactgagaa | 43860 |
| tctggatgaa gcgctagtaa tactattgaa atccgtatac aaagataaaa atgtaggatg | 43920 |
| actgcaggtg gtagttagga gccacggacc tggttaagaa gataccaaat tgtaggggtg | 43980 |
| aatagaccta accctggctg gctagtctag gtcagtacta cagtttagac aggggcaacc | 44040 |
| aggcaaaata caattaaaat aatcaccatt attaactatt atctacgcaa ttactaatga | 44100 |
| cttaactgga cttagagact gaggattcta caagatttca agaaacaaac aaaaagacat | 44160 |
| cacatacgaa cgccaaaatc actagtgctc cgtcaaggtt ttcggtccac agccccgtaa | 44220 |
| cccctcggca tttggaacaa aagtctccga gtaaaccacc ccgactgtta tgcatcactg | 44280 |
| ttgtcaaaca ctccgaatgt gcaatcctgc caccggcgac tattcccct cgcagcacgg | 44340 |
| tcatataagt ctacagaaaa tgttccatat ctcgatgatc gtgtatatat ttcttcccag | 44400 |
| ccaatcgtca ctgactccac gaaagtgccc ggacgttcct catgtccgag tgaagaagtc | 44460 |
| aaagtcacag tcacggatga acttgcttct cccatctgtg aatggatatc gtccaacatg | 44520 |
| gttgagaatg tctcctctcc ttcgtcgcca cggacttcga gtccgagtgg ctcctgtacg | 44580 |
| cccaccagcg ccaccagcgt gggatccgac gacaagagta tgcccattgc tgtcgtcggg | 44640 |
| atgagctttc ggggccccag ggatgccatc agcgtggaga gtctctggag gatgatctcc | 44700 |
| gagggccgcg agggatggag taaaatcccc aagtcacgat ggaataatga cgccttctac | 44760 |
| catccggatc atagtcggca tggaacggtg agggcttcct tttctttgaa agctgaacgc | 44820 |
| gaagcgagat caaatggaaa gttaaattcc taataaaaat tacgagtggc taatggaaac | 44880 |
| gcttagatca atgttgaagg agggcatttc ttggaagaag atctcgctcg cttcgatgct | 44940 |
| cccttttca atatgaccaa cgcagaagca gccgtagta ttaagagatt tctgacatgc | 45000 |
| aactatcgtg gctgaaaccc gtcaggcact ggatccccaa caacgactgc tactcgaaag | 45060 |
| caccttcgag gctgtcgaaa atggtgagtt gttggtcttt gtttcccaga ccaaaatgaa | 45120 |
| tccctgacga tcgtagcggg aatacccctg gacaagatgc ttgggtccaa gacctcctgc | 45180 |
| ttcgtgggct ccttctgcgg cgactacacc gacatgcttg tgcgagaccc cgaggccatc | 45240 |
| cccatgtacc aatgcaccaa cgccggtcag tcgcgggcca tcacgccaa ccgggtctcc | 45300 |
| tacttcttcg atctgcgtgg gcccagcgtc accgttgata cggcttgctc cgggagtcta | 45360 |
| gttgccctcc acctggcctg tcagagctta cgaacggggg atgcgaaaat ggccattgtc | 45420 |
| tccggggtca ataccattct gagccatgag tttatgagca ctatgagcat gatgcggtaa | 45480 |
| gagtcgtacc cctatcgttt tgcggatcca gtctctcaca atgtcaggtt cctgtccccc | 45540 |

```
gatggacgat gttacacgtt tgatgagcgg gccaatggct acgcccgagg cgaaggagtc   45600
ggctgtctac ttctgaaacc cctgtcggat gccctacggg acaatgatac gatccgcgcc   45660
gtcattcgag ggacgggctc caaccaggac ggtaaaacgt cgggcatcac cttaccaaac   45720
gccaatgccc agcaggaatt gatccgcgac gtctacgcgg ctgcggggct ggatcctctg   45780
gaaaccgagt atgtcgagtg ccacggtacc ggcactcagg ccggcgatcc tctcgagacc   45840
ggcgccgtgg ccaaggtctt ttctcctggc cggccgacg atcggccgct cgcatcggc    45900 tctatcaaga cgaatgtcgg ccacttggaa ggggcgagcg gcattgcagg cgtgatcaaa   45960
gcggtcctga cgctggagaa ccaatgtttc ctcccaaatc gaaacttcaa gagcattaac   46020
ccgcgcattc cgctcaagga gtggaaattg aaggtgcgtg agttgtcgtc gtctgctacc   46080
atcgtcgtct gctaccaaca agaaactgac atcgtcagat ccaactggag aatgaacgat   46140
gggaaacagt aggcccccat cgggtctccg tcaacagttt cgggtacggg ggaagcaatg   46200
cacacgccgt tcttgaagac accaagggtt accttgaaca gagatcccta acaggctcct   46260
tccgccgcgt acgagcgctt ccccatgccg ccactgacct cgagccagtc tcggacccgg   46320
gttctggccc agagcgtacc cgactttttg tcctgtccag ttttgatcag gcgtctggtc   46380
agcaacagat cgaccaactg cgggaatact tggagcagaa ctcctctcga atagatgatc   46440 aataccctggc agatctcgct tacactctcg gcgagcgccg ctcgcccttt ctctggaaga   46500
cggcgatgcc ggcatcgtcc gtgtccagtc tcgtcgaagg gttgaagact cgcgccaagg   46560
tctctcgggc cgagaagaag aagccgacgc tgggcttcat cttcacgggt caaggcgctc   46620
aatggtgcgg catgggtcgc gagcttctgg cagcgtatcc cgtctttgct tcgagcgtgg   46680
acgctatcgc cacctatctg aaaagccttg gggctcccctt cgacgtccgg gaggagctcg   46740
tccgggatcc caaggactcc aagatcaatc aaccgttgta cagccagccg atatgcaccg   46800
ccgtccagat tgccctggta gatctgctca ccttctgggg aatccggcct gcctctgtga   46860
ccggccactc cagcggcgag cttgcggggg catacacgc aggggccctg agcatggaac    46920
acagtatggc cgctgcgtat tatcgaggcg ttgcgtccag tgatcttccc cgagaccaca   46980
cgcaacgagg cgccatgatg gcggtgggag ccagtaaaga cgccatccag ccccgattgt   47040
cctcgctgac gacgggcacc gccgtggtcg cgtgcgtcaa cagcccctcc agcgtcacca   47100
tctcgggcga tgcatccgct gtggacgagc tgcatggttt gctcgagaag gaccaggtgt   47160
tcgcgcggaa gttggccgtc gacgtcgcct atcactcgca ccatatgaaa gccgtggccg   47220
accaatatcg caccgccatg gccgcgcgcg gcgtcaccgc ggttcagcct gagtccacgg   47280
agcccgaagt ggaattcttc tcgtccgtga cgggcgagaa agccagcctc accgacctgg   47340
gaatcgaata ctgggtcgcc aacctgctca gccaggtcaa gtttgccgat tccgtgcatc   47400
gcctgtgcat ggagacgtcg gcttccggac gggctcgcaa gaccaaaacc aaggcaccga   47460
aacgctcagg ggccaacaac aaggccaagg tcgacatgct cgtcgagatt ggcccgcatt   47520
caacgctggc agggccaatt cgccagatcc tcggggccga ccagacgctg gagcaggcgt   47580
cgatccgcta tgccagtgcc ctgctgcgca agtcgagtgc ggtcgatacc acgctgaccc   47640
tggcgtcgac cttactgatg gccgggtatc cgatcgacat ggctgccatc aatcgaccgt   47700
cggatcacca ccgagtgggc gtcctcgtcg atctccctcc ctatccgtgg aaccactcgg   47760
gatcatactg gcagagccg cggttgagca aagcctatcg caaccgcgct catccccgga    47820
acgaccttct gggagtgttg gatacgcatt ccagcccgcg ggagcccgg tggcgcaatt     47880
```

```
atctccggac gagcgagatc ccttggatca aagaccatat gatccagtcg aacgtggtgt   47940
atccggcggc cggctacctc accatggcgg tcgaagccat cgggcaacgg attggggaca   48000
acttcccggg ccaccgcatc tcgggatacc gactacgaga tgtcgcgatc gaggcggctt   48060
tggtgattag cgacgactcg gagccggagg tcatgctctc cttgcgtccg tctggcgaca   48120
gtggcctggt tccggccgaa cggtggcatg aattccacgt cctttcagtg accccgaca    48180
accggtggac ggagcattgt cgcgggctca tctgcgccga ggtcgcggcc atggacgggg   48240
acgaagatga ccgtggcgca gaggcagggt tgaccgccga gacagagcgc tggatcgagg   48300
aagcggagca gctctgccag aaagacgtcg atatccccg gttctacgca gagttgaccg   48360
gtctgggtct ggaatacggg gagacctttg ccaacatgac gcgagcacgt tcggcctccc   48420
atgtctgcct cgcggagatc gaagtcgcg acactgcggc tgtcatgcct ctgggattcc    48480
agtctccgtt cgtggtccat ccctccaccc tggacagtct cttccatcct ctcttcgtcg   48540
ctctgtcctc cgacgagtca ctgcaagatc ctgccgtgcc ggtggccatc gaggagatat   48600
ggatccgcca cggcatggcc aaggaggccg acacaagtt ccaggtctgc gcgtcgaccc    48660
aggagacggg tcgagaccgc attcaggcag ctatctcggt ggttgatgct cagagggctc   48720
gcagcggacc ggcgttgacg gtccgcggcc tgacgtgcca gttcctggac cgcgcatcgg   48780
gagatgtcga gggcgacgag cagcctacac ggcttgcata cgagcttcac tgggaggcag   48840
atgtagacct gctgtcgtcg agcgacctgg ccacgctgtg tgcggttggc cgtccccgtg   48900
atgtagggga gaaggtcgct cgatatgtga agcttctcgg acacaagaac cctcatcttg   48960
ccatcctgga ggtcggagcc ggtcaggag agctgtgtat tccggtgttt cgagccctgg    49020
caggggaggc caacagcacg ccctcgttcc agtcatatac actcgccgac accgagccgg   49080
gactgtcgga gaccattgcc acaattgccg accagtttga cgaacgcgcc gatctgattc   49140
aatataagga gctcgacatc tcgtcggacc cgctgcagca gggcttcaac gctcactctt   49200
tggacctcat ccttcttcct tcccggggag tgtcggccac gctccgatcg aagatcctca   49260
aacatgcgca ccaattgctc acgcccgaag ggagactgat tgtggtcgac acgagggacc   49320
tgcaggaatg gtggcaagct cttcgtgaga gcaactttac tgatccggaa gtgattcacg   49380
acagtccgag cgagacggag gccgacatct cggtgctggt gtcgaaacca caaccacaac   49440
ctcgggatca gacccccatca gaccctccgg atgtcctggt tatcgccgag aaccaagact   49500
ccggcgtgtc cattgagcat ctccagcgtc tgctggcgga cgctcatgtg ccggcgaccg   49560
tcacggattt cgctcatgca gacccggagg gcaagacgtg cattgttctc agcgagttga   49620
cgacctctct gctgagccat cccgaccagc attcgtttga aacgctcaaa aggatcctcg   49680
tcgccgggg tcgcggcgtt ctctgggtcg ttcggggagc aaccggccca cgcgcccacca   49740
gcagtctggc caccggtctg ctgcgcacga ttcgctccga ccgacgat gatcgaccga     49800
ttgtgagcct ggatctggat gcctcccatc ccctgtcggc ggaatccgca gcgcaatcga   49860
tcttctccgc gttccgccac cgattcgtct ccccggagg gagtcacgag gtcgaatacg    49920
ccgaacgcga tgggatcctg cgcatccctc gcgtcgtcga gagttccctc gtcaaccacg   49980
agattgtctc gtccttgcgg ccggcggtgg ccgaggacca gccattcttc cagcccgac    50040
gtccgctgga actcaccgtc ggcaccccgg gacgtctcga cagtctctac tatgtcgacc   50100
gctcctgcat ctcggagcta cccagtgact acgtcgagat cgaagtcaaa gccatcgggc   50160
tcgggaacgg cgatgtcaag accgctctgg gacatgacga tgccgcaacc cgtccggag    50220
cggaatgcag cggtgtggtg actgctctcg gggacgccgt ttcgggcttc aagatcggag   50280
```

```
accgtgtcgc tggctttggc gcaggaaccg tcgccacttt ataccgagac caggcggcgc  50340
ggttccagct catccccgac gacatgagct ttgcgcgtgc ggccgctctc cccgtggcat  50400
atatcactgc tttcttcgcg gtccacgcgc tgggccaggt gagccgaggg gaccgagtcc  50460
tcatccagga cgccggcacg gccgcgggcc aggctctcct ggagctctgt gccctcgccg  50520
gggggatat catcgccgtg gtggattcgc cctcgcaaag agccttcctc gttggcgagt  50580
acgacctccc ggcgagcaga atcctggtcg gtctccgcgg acgacgtcta gcaaccagcg  50640
tcatgacgct gactagggc tgcggagtcg atgccatctt caatttccgc ggaggcgagg  50700
agagacgcct gtgctggagc tgcgtggcac catatggccg gttcattgac ctgggcggcg  50760
gaccgtccga cctgacggat atgccgcagc tcgagatggc cagcttcttt ccaagaatg  50820
cttccttcac ggctctggac ttccactacc tggtcacgca aaagccacag gcggtgcacc  50880
ggatctggtc cgacgtgatg gccctggtgc gagcaaaggc catccggggc ccgcccaggc  50940
ttcaacttca ttccgtctcc gaggtcgaga ccgcgttgaa acagagtcag gacgcgatgtg  51000
atgtcgagaa agtggtgatc cgtgccgaac gggatacaat cgtccaggtc tgttgccact  51060
ctgccccctta tgatatcctc cctcgtgcta atatgttctc ttgcaggcca ttcctcctcc  51120
gaagggcgac ctgctgaggg ccgacgcgtc atatgtgcta gtcggcggcc tcggaggcat  51180
tggacgagcg atggcatcgt ggatgattgc caacggagcc cgacacttaa tctttgtcaa  51240
ccgcagtggc ctcgcccgca acgaagcccg ggagacggtc gagtctctcg agggtcacgg  51300
tgcccacgtg gcggtctatt cttgcgatgt cagcgatcgc gaccaagtcg ctcagatggt  51360
tgctcagagc tccaaagaga tgccgcccat tcgaggcgtg attcaggcgg ccatgattct  51420
ccgggtatgt ctgccttctc gaaattagta ggtcgaggac tgactgtagt aggatatgct  51480
gtttgagaaa atgagcgtcg acgacttcaa caccgtccta cagcccaaat ggcagggcac  51540
atggaatctt catggcctcc tacccgaga catggacttc tttatcatgc tgtcctccat  51600
cagcggggtc atcggcaacg ccactcaggc tgcctatgcc gctggatcga cgttcttggg  51660
cgcgttcgcc cagtatcgca gctccctggg actaccggcc gtgacgctgg atctcggcgt  51720
tatcactgga atcgggtacc tgtccgagca cgaggagctg ctccagggca tgcagcgaca  51780
aggctttgaa ggcaccaacg agcagacgct gatggccctc atccgatcag ccattgtcag  51840
ccctcgtcgg acggggtcac aagccgagat cgtcaccggg ctggggacct ggcgagaggg  51900
cgtctcgctg ggcaacttcg accagcccctt gttcgcgcac ttccgccgtc aagccctggg  51960
actccgagat gccacggcag aggggcccgg caccagcgtc cggagagtc tccggggatg  52020
caagaccctc gacgatgcgg tggctctggt ctgtgcggct ctgatcgacc gcctggcctc  52080
gagattgaac accccggtgg acaatatcga ctcccagcgg gcgatgtcgg agtacggggt  52140
ggactcgctg gtggcggtgg agatgcgcaa ctggatcggc aaggagatgg agagcacgat  52200
gcccattctg gagctgctgg cgaatcaatc catctcgcag ttgtcggaga agatagctca  52260
gcggtcaaag gtggtggcag tgagtggaag tgaagagtag agtatgaatt gcgatttgga  52320
tggttttta gttcacatca gatgacggca ttgtatttat ttgaataacc agaatttgat  52380
atcattattt cccaggaagt ggaagacaaa aggattcaag gatatctaca attttgcgt  52440
caaaaattga atgcatcgtt tccttggcgg ttattggcat actatcaagg tcatcccgct  52500
ccaatcccta aaacccagtt tcaatacgcc aactctggag ctttttttttt ttttttcttc  52560
tagatagtta actgtcacat cctgggatttt ataagaacta cataatgatc gttcccctag  52620
```

```
aacttctttc aatgataaaa cagaaggaaa acaaaaaaag aaagaaacaa tcggcacaat      52680
catgaatcat aacttttcat cccccctcaa caccagacaa atcgagtcgg agtcgcacaa      52740
ggcgcggtac tcagcgaggt tgtcgtcact ctcggcggag gcgccgaggg cgtctcttcg      52800
ttccgagccg tgaaataact cgccgcaata ggttcctgca accccgcgac gtgcatgaac      52860
tgggccaggt tgaagcccga gcgggtgtcg acgctgatcg gccgggtgct cgagaagcat      52920
tcggggaagc gatatgtcgt gggctgctca aataaaagga gcacgtaggt atggcgaggg      52980
ccggggaccg ggcgcgggcc gacatagggg acgtcctcat cactcaacct cgccagccgg      53040
ccggtgaagg gatcgcggac cttcaggtcg ggctgtagcc agtgcaccag gggcgttgcg      53100
gtgccttcgt ggttgacttc gacgtcgatc atcacggcga ggtaggactg gaacacactg      53160
agaccttgcc gaccgaatac cgggggggtcg atggcatcta cacgaatcag atattagtgg      53220
ggaaagctct gactggtcgg aagaatatat cacattacca tcgggaagga ctaattggcc      53280
cggttgaatg agctgctggt cacgaaatat gacatccagg cccctcgggg tctttggcca      53340
gtatcctggt ggcgtctggg cggcgatcaa ggggaggcac accaaggcca gaagaagcca      53400
caagtctgga cgcatgctgc aaatggacga tagcaatagc ggacagccag atcattcact      53460
gtctccatag tgtgtagtgt gtagataagg ttgtggatat atatttggtg gtgcagaagt      53520
cgccgtggaa agtgaccgat tcccccgctat tatgcggaca ataaagtgat tcattccgac      53580
tcttagaaat ggttgcgtac ataggtaacg taaaagaaaa gaagacaatt ataattaatg      53640
aagaaatgga ttaaatcagc atcaacgatt tactacaata caaacagggg cccggaagtt      53700
tgtagctggc cggataggaa aagttgcggg tgatatataa agcatgataa taggtcttca      53760
cgaccggcag ctttggttca tactggcaca tatcctgtct tttagaatat catgtagagc      53820
tcttctgcgc catcaagtat gcagccacac tacccgttgc tcgaggatac tgaatctctc      53880
cttcaaaccc attcgtatga tgtccattca gaaaatcccc aagtgtatat ctatgttatg      53940
agccatgaga ggggcaacag ccgaaaaacct ccctcatgat attgctcgaa accgcaaact      54000
gagattggga agcataacac atgaagcaat atcttcgctt tgtactactg tcctcctact      54060
atcaatacca atcgcagtta tgcaggtaga cctgttctct gtagacgagg ctgtgtcgga      54120
gtcagcctgg tctgcctgtg tcccgcagca gagtgtacac attaatagcc tcgtcatcgc      54180
ccaaagcatg gccagtccaa aaggctaaat agaacagcaa cgtcccagtt ccttatcttc      54240
ttgaaagtat ctagctcact ttactgtaca ttcattctca tggccgggcg gcgtaggcga      54300
agccgcgagc atcgcaggct tcctcagcct tgcggtgcgg ggcagacagc cgcaggtgcg      54360
atcaaactct acaattttgt aaaatgtac caggaagtcg actccatgat cgcccagata      54420
gtagaagacg ctggaagcct ccatcgagct gttgcccagg tggaggagtt gaccccgaag      54480
cttgttgcag cgagtccttc ctccgagaaa gtactcgtcc caatcaagaa acaaatcgca      54540
gagtgcaagg cagatctcag ttcctggaat aagagaattg attcattggg gctatcgaga      54600
gcgaaaggga tttcagcatt caggaagagg ttcaaagcaa ctgtggacag gtcgttttc      54660 gagaatgtca gaagccggct ttgcttccat cgggagcaac tgactctgct acttacaacc      54720
gccgacgcgt atgtgactct attaccttgc cgttatttat ccatctaact gttggtcaag      54780
taatgttgga gttgagagcc tcccgatgac aaacaaatcc gagatacgtt ccaacttcgc      54840
gtccgggaac cgggattcca agaacctgtc tcgcgtcagc tcaccacgat tgacaaccgg      54900
ataacagatc aatcagctag ttttttttcct ctactcaacg gcagttcgat aggttcttcg      54960
atggctattt ggagcaggga ggacaaacta tatgccgtct tgaagctatt gatacgaggt      55020
```

```
tgcaatgcct gcaagcccgg cttgagcagt cgatcaatcc ccaaagccag aaaacaactt   55080
acaacccgaa gaagtctaga agacaagcat atgtacgaca gatcccacgc aagacacggt   55140
tgctggagct cgtgggctcg ggaagaggtc tctatcatgc tcacgaaaga cagaccgaca   55200
ttgaagaatt tcctctgcgc gtgatacaga ctgggttgtt gctcaccgag caaaaaggaa   55260
agattatgtc gacccttctc gctcttgagg attgatgagg gaggatctag gggaacggat   55320
cctgaatatg aagattgttg ttattgctag gagctagcta ggtgggtgag gtggaagtta   55380
tcccttcctc cttgggctaa gcctatttag ggtgtagggg gccgattact tgcttcaagg   55440
atcaaaggta cagaagcgca agtttcgaac agaagctttc catggtcagc tttgtcagat   55500
ctcttcggct cttgctctgg ttactccaaa cccaaaatta tctggcattc acggaggtaa   55560
ggttcccaag gagatatgcc tcgaatctcc tggccaatga gcctttgaac tcgtttgga    55620 tagcctctgc aggagtaagg tacttcttca tcgtcagcag acaaaatct cggtccggcc    55680 ttctcacatc tgggggtcta gttccctag atcactagag agtcttaaat caatgggtaa   55740
gacgatccac tatatatttg aggctacatc ttgccgtgga gggctatacc ttcatcagtt   55800
gccgctccca ctgtcagaag acatctctgt ttgttgttct accctgtatt acggcggacc   55860
acttcctatg tcttagattg aataaacact tggtacgtct ttagctcaaa caaagagaat   55920
gctgtatgaa agtcacaatg accaacaggt caaccaattc atatgattac gcaataatac   55980
atcgccacaa gaccctgatc ccaaagaaga cattgacaag acatgtaaac agatccgaga   56040
caaacttcag aacaggaact gctccgccag tatgatgaaa agtggttaag cagttgtcag   56100
aaaatataga aacgagacaa aaaccgagat tcagagacgg cttcacacgg gcctacctca   56160
agaagcaagg atctcatcta gcgtccgatg ctcatccaat ttacgctctg cttcttgctc   56220
catcttcagg tggtaaagac caccaagttc agcccgctcc tcttcactca gaagcgccat   56280
tctatcctca accgaggtaa actccccgta atatctctga tcgatgaatt cccagtaaat   56340
gtcatcgaac gagaagctcg acctggccgc aaggcaaaac cagaaacttc cattgtggat   56400
cgactgctcc atgtgctcag acagtcgcgg cgagtctaca accgcgctac gggctgcggc   56460
ttcatcttcg cactctcgca ggacttcgag gaagatcttc tgtcggggca tgtactgggt   56520
gaagaagtcg ttgaacccat tctcccagct gtccggatgg gccagcagga gccaccaggg   56580
agagcaatac gtgaactcca gcggtgcagc gtagcagtat tcccagtcaa tgacgcttgt   56640
gatatgaagg tctgagtcca caagcacatt tgagggacgc aggtcatcac agaacaagct   56700
gaatggacca ttattatatg cggtcgagaa gttacgcgca atgtttctga atagacaccg   56760
ggccacatat ttcttcttgc agtccgcctc gtcgtcaaca gcgtcattgc gctgggtccg   56820
caggtgttgc agatggtctt cggcgagggc taagaagtat tcgtttgcag tggaaaatgg   56880
gcctttatgc aggtcctgcg gagggaaatt cgcgtatgtg agcagctcat taatgttgta   56940
tgtcaatggt cgcttataga cggaccaggc ccgtctgtg ttttgggtgg gtgctccgat    57000
gcgagagaat cgagatcggg acaactccag cagtactctc gccatttcgc ggtacgcagt   57060
tttcagcttg gaaatgctaa tctccggctc caagacagcc actcgggtac ggtcgggcaa   57120
gggcgccgaa aggtagtctc caagcggact cccttcggcg aagttcatca ccatgtaagg   57180
gccaacagca cagataccac ttccaaggac cttgggaaga ggaatggaag tatttcgggt   57240 aatataccc ataatgcata actcgtcgtt gactttctct ctccgcagag ccacctttcc    57300
cagaatgggg agccgcacaa tggcatcggg cccttctctg aaagtcatcc tgtagcaccg   57360
```

| | | | | |
|---|---|---|---|---|
| attgtaggcc | ccatctctgt | acgcgacagc | ctcgatcgga | atgcctcccc gatgcttcgc 57420 |
| tgccagcatg | gcagctaggc | gctctgtcaa | gcactgcttc | agattcctcg tccacactat 57480 |
| gtacatggta | tcgacgcgct | tgcgagcttc | atcgtcggga | tacatggctc aaaatgcggt 57540 |
| gttatcgata | aaaagaggct | ggacaaccag | agctttgtag | aagggaggtg aatcggcctt 57600 |
| agaaccaccc | cggattgctc | ctcttctact | ccgtataatg | cgatgtttgg acaccagcac 57660 |
| gatctgcagg | aaaaggggt | ccctgactga | aatgaggtta | gcgccagaac caggggtgtt 57720 |
| ttggatggag | tctgctagat | tgatcacaac | agcagatcct | cctaccgagt caatgaaata 57780 |
| tatagatgtc | atgcggattt | gactatgtct | gttattcttg | caagatcaga gatcatagga 57840 |
| cgtgatcaac | ccggatgttg | gctagtggca | aaagccataa | tccgacaatc catcattgtc 57900 |
| cgacataaca | ttgaatacct | tatctttcat | gaagtgctct | tgagcagctt atctgactca 57960 |
| tatcctcagt | ctttattctc | ctgatagtac | tgtctggctt | gaagtgaaat tgcttcttcc 58020 |
| tttttgaagt | tgtttctcat | ccaccactga | cctaggcagg | caggcaggca ggtaggtagg 58080 |
| taggcaggta | tatagaacct | gcagccagat | cctcttctgt | cagtatagtc ttattcaagt 58140 |
| taccttaaat | ccagtaaatc | caagtctaag | taccccgtgc | tctggtctac tccgtttcca 58200 |
| cttccctcct | agcgaagcgc | tgacagaata | gcaagcaaat | gtcaaaaaca agcggtcagg 58260 |
| ccgatcgaaa | ctcactcaaa | aagatagtta | aaacataact | tccgctcctc gggaactcgg 58320 |
| caaaatttac | gctgtacttt | gctccggtta | ataataccta | cctcagtcat ggaatggaat 58380 |
| ctttggatcc | gatgcaaggg | ggggggggctt | atatttgtgg | tttattattt tagatgtccg 58440 |
| ttaggtaaat | acgtgaggt | cgttgagtac | gtcgatgact | aaaaaagatt gggattatgg 58500 |
| acataacgga | cttaggaagc | tatat | | 58525 |

<210> SEQ ID NO 2
<211> LENGTH: 3395
<212> TYPE: DNA
<213> ORGANISM: Paecilomyces divaricatus

<400> SEQUENCE: 2

| | | | | | |
|---|---|---|---|---|---|
| atgggctcga | gtaccttcga | gcacgatagc | acccccgaat | atgggaaacg | tttcctaccc 60 |
| catatgatcg | atgaaagagc | ggcttcaggc | cattcacgtc | cttatgctta | tattgccaga 120 |
| tctccgcatc | cccaggacgg | cttcgaggaa | gtcagctacg | cacgtctggc | gaatgcaatc 180 |
| aaccgggctt | cctggtgggt | agtcaatgaa | ttaaccccctt | tgactggtga | aatggtgtc 240 |
| ttcgcgtaca | tgggtccgaa | cgacctgcga | tatctgatac | tgtctgttgc | ggctataaaa 300 |
| accggcagaa | aggtgggtta | cctccatttta | ctccatagga | cgaagaacac | ggctgatggc 360 |
| gtagatgctt | caaccatcaa | tgaggaatac | tgttgaagca | cagcagttgc | tattccaacg 420 |
| catcggatgc | aagacaatcg | cctacgcagc | taccctggag | aagagtctac | atcctatttt 480 |
| cacatccatc | tccgggctgc | agaccaagca | ggctcctagt | ttagaggatt | cctttcgga 540 |
| agatgtggtt | cctcacttcg | aatacaaggg | cagctacgaa | aaattgaccg | atgaaccgct 600 |
| catatacttc | cacacgtctg | gatcttcagg | tctgttgcct | ctagtttact | gagcgcatct 660 |
| cctagttaac | tatgagaaca | ggaaatccga | aaccaattgg | tttcagtctg | cgatggcttc 720 |
| ttctcttctc | tgatgctccc | aatttacccc | ctattaatag | tcgcccgtca | acagtgaagg 780 |
| agggcctgta | ccgccaaaat | actttatgtt | tccttccacc | gttccatgta | tgtatggggc 840 |
| cctggatatc | gagtgcatga | tccttgtgag | ctaaactgta | ataggccggc | ggattcggtc 900 |
| ttgctgccgc | agtggtgtac | tttgaagcca | ttgctgtttg | tcctcatccg | gaggttgcac 960 |

```
caacagcaga atacatattg tcgctgctag accaaaatat tgccacggcc ttatcggttc    1020
cgccttctct acttgacgca ctctcgaaga catctgctgg gatcgaggct ttgtctaagc    1080
tggaacacgt tggctacgtc ggaggcccgt tgcccgagca cgttgggcag gctcttgcgc    1140
caaagctgaa gcacctctac agtctaatgg gggcaacgga gtgtggctgg ttccatacca    1200
tacctggcga cagcagcaaa tgggcgtatc tacgtttcaa cccggatatt ggctatcggt    1260
tcgatgagat ctccgaaggg gtcttcgaat tggtcatacc taatagtccc gtaaccagga    1320
aagtgcatgg taccccacat atatttccgg aactgaacga atacagaaca agagatcttt    1380
actccttagt cccgggagag gaagggtgga tgcgttacca gggaaggagt gacgatctta    1440
tagtcctgtc caacggtgag aagatcaatc ctgtacctct ggagggtatt ataaacagcc    1500
attcagcgat caagggtgcc ctcattgtgg gggagtatcg attcttgcct tctcttctga    1560
tagaggtcca ggatgatttc agcgctgaaa cagaagagga gcgtctggag ctgcttgaca    1620
agatctggcc aaccgtcgaa caagcaaata agatcgcccc acgcttctcc cgggtaccga    1680
agtccttgat ctatcttggg aagaaggatg aacactttca cagagctggg aaggggacca    1740
tccagcgtca gcgcaccgtc agcaactttg cgaaggcctt agatgaacta tacttcgctg    1800
cagagcaggg gctgcttgtg gaaggtctag agttggatga cccctcaaat aaggattcga    1860
tcagagcgtt caccaggaag cttacgctc aagctctaga tgccgaggaa atcaaagacg    1920
aagatgacgt ctttaatctc ggcatagact ctcttcaagt cgctatcacg gttcagaaga    1980
ttagggcgac catgagggca cgaccggtag aactggacca tgagcagatc aatggacaac    2040
tgatttactc taacccaacg gcaggtgacc ttgcaacggc cctcaataag ctcgtaaact    2100
gtgaaagagg tgtacctctg gacggctctc tcaatggtgt caacgaacgt tcgactcgtt    2160
tgcagcagct acttgacaag tacatagcag caatgcccac gatgctcgat gaggcggaaa    2220
aagcgaatac gggccgctcg actgtcattt tgacaggttc aactggttct ttaggaagct    2280
acctcttgac aaccttgttg tcctcgcctg cagtctcgaa ggtagtctgt ctcaatcgat    2340
ctagtgacag cgaaaagcgc cagagagcta ttcataacgc acgtggacaa gctatatctt    2400
gggagaaaga agaccgagag agagtcgaat tcttaacagc agatttatca aaaccagacc    2460
ttggtctggg ggatcagaaa tacagtgatc tattgtcaga agcatcagca atcatccact    2520
gcagctggaa agtcgatttc aatcacactc tcagttcttt cgaagcgacc catattgccg    2580
gggtgataaa tctgatcaca ctcagcgcca aatctgcaca ccacgcacct attatgtttg    2640
tctcgagtat atccacagtc ttcaattgga tcgaaacgca cccgaatctc cctgtcccgg    2700
aagccattct caatgatcta gacagctccg agaaactagg ctatggagag tcaaaatata    2760
taggcgaaag actaatcgag gcttataccg cgtccacggg cattcaaaat gtcgtcctga    2820
gagtcggaca aattgcaggc ccggtacttt cctcttctgg attctggaat aagcaggaat    2880
ggttccccag cctggtcgcc agctcaaaac acctgggatt attgcctgag tcactaggga    2940
ctatgaatac gattgattgg ataccggttg accttctggc atcgattatc acccagctgc    3000
ttcaatccgt ccacaacagc ccggaatccg aagtgaagtc acctgctgtc tataacctcg    3060
tcaaccctcg agtgactaca tggcccgctc ttctccacag cgttcaagaa gaccttggtg    3120
gacaatcaaa cgtacgagtc gtcccattgt cagaatgggt ggaagcgctt gagagaagtg    3180
cttcgcacaa tcacgggtat gtgatagcag agaacccagc tgttaaactg cttgatttct    3240
tcaagctgct agggaagaac ggagagggga acgtgggcga agcgaaatcg caatataagg    3300
```

-continued

```
tagctcgcct gctgagggat agtccacagg ctagacagct gggcttcgtt tctccagaat    3360
ggatgcggat gtggttgaag cagtggaagt tgtga                              3395
```

```
<210> SEQ ID NO 3
<211> LENGTH: 1077
<212> TYPE: PRT
<213> ORGANISM: Paecilomyces divaricatus

<400> SEQUENCE: 3

Met Gly Ser Ser Thr Phe Glu His Asp Ser Thr Pro Glu Tyr Gly Lys
1               5                   10                  15

Arg Phe Leu Pro His Met Ile Asp Glu Arg Ala Ala Ser Gly His Ser
            20                  25                  30

Arg Pro Tyr Ala Tyr Ile Ala Arg Ser Pro His Pro Gln Asp Gly Phe
        35                  40                  45

Glu Glu Val Ser Tyr Ala Arg Leu Ala Asn Ala Ile Asn Arg Ala Ser
    50                  55                  60

Trp Trp Val Val Asn Glu Leu Thr Pro Leu Thr Gly Glu Asn Gly Val
65                  70                  75                  80

Phe Ala Tyr Met Gly Pro Asn Asp Leu Arg Tyr Leu Ile Leu Ser Val
                85                  90                  95

Ala Ala Ile Lys Thr Gly Arg Lys Met Leu Gln Pro Ser Met Arg Asn
            100                 105                 110

Thr Val Glu Ala Gln Gln Leu Leu Phe Gln Arg Ile Gly Cys Lys Thr
        115                 120                 125

Ile Ala Tyr Ala Ala Thr Leu Glu Lys Ser Leu His Pro Ile Phe Thr
    130                 135                 140

Ser Ile Ser Gly Leu Gln Thr Lys Gln Ala Pro Ser Leu Glu Asp Phe
145                 150                 155                 160

Leu Ser Glu Asp Val Val Pro His Phe Glu Tyr Lys Gly Ser Tyr Glu
                165                 170                 175

Lys Leu Thr Asp Glu Pro Leu Ile Tyr Phe His Thr Ser Gly Ser Ser
            180                 185                 190

Gly Asn Pro Lys Pro Ile Gly Phe Ser Leu Arg Trp Leu Leu Leu Phe
        195                 200                 205

Ser Asp Ala Pro Asn Leu Pro Pro Ile Asn Ser Arg Pro Ser Thr Val
    210                 215                 220

Lys Glu Gly Leu Tyr Arg Gln Asn Thr Leu Cys Phe Leu Pro Pro Phe
225                 230                 235                 240

His Ala Gly Gly Phe Gly Leu Ala Ala Ala Val Val Tyr Phe Glu Ala
                245                 250                 255

Ile Ala Val Cys Pro His Pro Glu Val Ala Pro Thr Ala Glu Tyr Ile
            260                 265                 270

Leu Ser Leu Leu Asp Gln Asn Ile Ala Thr Ala Leu Ser Val Pro Pro
        275                 280                 285

Ser Leu Leu Asp Ala Leu Ser Lys Thr Ser Ala Gly Ile Glu Ala Leu
    290                 295                 300

Ser Lys Leu Glu His Val Gly Tyr Val Gly Gly Pro Leu Pro Glu His
305                 310                 315                 320

Val Gly Gln Ala Leu Ala Pro Lys Leu Lys His Leu Tyr Ser Leu Met
                325                 330                 335

Gly Ala Thr Glu Cys Gly Trp Phe His Thr Ile Pro Gly Asp Ser Ser
            340                 345                 350

Lys Trp Ala Tyr Leu Arg Phe Asn Pro Asp Ile Gly Tyr Arg Phe Asp
```

```
            355                 360                 365
Glu Ile Ser Glu Gly Val Phe Glu Leu Val Ile Pro Asn Ser Pro Val
370                 375                 380
Thr Arg Lys Val His Gly Thr Pro His Ile Phe Pro Glu Leu Asn Glu
385                 390                 395                 400
Tyr Arg Thr Arg Asp Leu Tyr Ser Leu Val Pro Gly Glu Glu Gly Trp
                405                 410                 415
Met Arg Tyr Gln Gly Arg Ser Asp Asp Leu Ile Val Leu Ser Asn Gly
                420                 425                 430
Glu Lys Ile Asn Pro Val Pro Leu Glu Gly Ile Ile Asn Ser His Ser
            435                 440                 445
Ala Ile Lys Gly Ala Leu Ile Val Gly Glu Tyr Arg Phe Leu Pro Ser
            450                 455                 460
Leu Leu Ile Glu Val Gln Asp Asp Phe Ser Ala Glu Thr Glu Glu Glu
465                 470                 475                 480
Arg Leu Glu Leu Leu Asp Lys Ile Trp Pro Thr Val Glu Gln Ala Asn
                485                 490                 495
Lys Ile Ala Pro Arg Phe Ser Arg Val Pro Lys Ser Leu Ile Tyr Leu
                500                 505                 510
Gly Lys Lys Asp Glu His Phe His Arg Ala Gly Lys Gly Thr Ile Gln
            515                 520                 525
Arg Gln Arg Thr Val Ser Asn Phe Ala Lys Ala Leu Asp Glu Leu Tyr
            530                 535                 540
Phe Ala Ala Glu Gln Gly Leu Leu Val Glu Gly Leu Glu Leu Asp Asp
545                 550                 555                 560
Pro Ser Asn Lys Asp Ser Ile Arg Ala Phe Thr Arg Lys Leu Tyr Ala
                565                 570                 575
Gln Ala Leu Asp Ala Glu Glu Ile Lys Asp Glu Asp Val Phe Asn
                580                 585                 590
Leu Gly Ile Asp Ser Leu Gln Val Ala Ile Thr Val Gln Lys Ile Arg
            595                 600                 605
Ala Thr Met Arg Ala Arg Pro Val Glu Leu Asp His Glu Gln Ile Asn
            610                 615                 620
Gly Gln Leu Ile Tyr Ser Asn Pro Thr Ala Gly Asp Leu Ala Thr Ala
625                 630                 635                 640
Leu Asn Lys Leu Val Asn Cys Glu Arg Gly Val Pro Leu Asp Gly Ser
                645                 650                 655
Leu Asn Gly Val Asn Glu Arg Ser Thr Arg Leu Gln Gln Leu Leu Asp
                660                 665                 670
Lys Tyr Ile Ala Ala Met Pro Thr Met Leu Asp Glu Ala Glu Lys Ala
            675                 680                 685
Asn Thr Gly Arg Ser Thr Val Ile Leu Thr Gly Ser Thr Gly Ser Leu
            690                 695                 700
Gly Ser Tyr Leu Leu Thr Thr Leu Leu Ser Ser Pro Ala Val Ser Lys
705                 710                 715                 720
Val Val Cys Leu Asn Arg Ser Ser Asp Ser Glu Lys Arg Gln Arg Ala
                725                 730                 735
Ile His Asn Ala Arg Gly Gln Ala Ile Ser Trp Glu Lys Glu Asp Arg
                740                 745                 750
Glu Arg Val Glu Phe Leu Thr Ala Asp Leu Ser Lys Pro Asp Leu Gly
            755                 760                 765
Leu Gly Asp Gln Lys Tyr Ser Asp Leu Leu Ser Glu Ala Ser Ala Ile
            770                 775                 780
```

```
Ile His Cys Ser Trp Lys Val Asp Phe Asn His Thr Leu Ser Ser Phe
785                 790                 795                 800

Glu Ala Thr His Ile Ala Gly Val Ile Asn Leu Ile Thr Leu Ser Ala
                805                 810                 815

Lys Ser Ala His His Ala Pro Ile Met Phe Val Ser Ser Ile Ser Thr
            820                 825                 830

Val Phe Asn Trp Ile Glu Thr His Pro Asn Leu Pro Val Pro Glu Ala
        835                 840                 845

Ile Leu Asn Asp Leu Asp Ser Ser Glu Lys Leu Gly Tyr Gly Glu Ser
    850                 855                 860

Lys Tyr Ile Gly Glu Arg Leu Ile Glu Ala Tyr Thr Ala Ser Thr Gly
865                 870                 875                 880

Ile Gln Asn Val Val Leu Arg Val Gly Gln Ile Ala Gly Pro Val Leu
                885                 890                 895

Ser Ser Ser Gly Phe Trp Asn Lys Gln Glu Trp Phe Pro Ser Leu Val
            900                 905                 910

Ala Ser Ser Lys His Leu Gly Leu Leu Pro Glu Ser Leu Gly Thr Met
        915                 920                 925

Asn Thr Ile Asp Trp Ile Pro Val Asp Leu Leu Ala Ser Ile Ile Thr
    930                 935                 940

Gln Leu Leu Gln Ser Val His Asn Ser Pro Glu Ser Glu Val Lys Ser
945                 950                 955                 960

Pro Ala Val Tyr Asn Leu Val Asn Pro Arg Val Thr Thr Trp Pro Ala
                965                 970                 975

Leu Leu His Ser Val Gln Glu Asp Leu Gly Gly Gln Ser Asn Val Arg
            980                 985                 990

Val Val Pro Leu Ser Glu Trp Val  Glu Ala Leu Glu Arg  Ser Ala Ser
        995                 1000                1005

His Asn  His Gly Tyr Val Ile  Ala Glu Asn Pro Ala  Val Lys Leu
    1010                1015                1020

Leu Asp  Phe Phe Lys Leu Leu  Gly Lys Asn Gly Glu  Gly Asn Val
    1025                1030                1035

Gly Glu  Ala Lys Ser Gln Tyr  Lys Val Ala Arg Leu  Leu Arg Asp
    1040                1045                1050

Ser Pro  Gln Ala Arg Gln Leu  Gly Phe Val Ser Pro  Glu Trp Met
    1055                1060                1065

Arg Met  Trp Leu Lys Gln Trp  Lys Leu
    1070                1075

<210> SEQ ID NO 4
<211> LENGTH: 1029
<212> TYPE: DNA
<213> ORGANISM: Paecilomyces divaricatus

<400> SEQUENCE: 4
atgggctacc tcgagaatct gcccgcagaa ctgctgttcc tgatcgtcga ccagcttgac      60
agatatgact tgatgaactt gcgcgtggta caccggcgct tcagtttcgt gaacccacgt     120
gtcttcaagg tcatgcgttt ctacaacgag cctaccgtcc ccgtgaaact tcgcaagctg     180
ctcaaacggg aggatatgag atccgctctg acgagataa tcttttcgac agactctctc     240
ttccggggtt acaaccggca cgatgcagcc ctgaggctca gagggttgc ccgtctgctc      300 gcaaatcacg acgatgtcaa catcaaaacc gtacatctcg tcggcgattc aggaggtctg     360
ggacttctgc ttcgttactt tgcagaagca ggtatcaggt cgcttcggta cctctctggc     420
```

```
gccataattt tcgccacca tgagatcaac gaggaatggc ttcctcacct gatggatgag      480
tctggcgtct tggaagtctt gggaggcttg aacgcctgg  acctcactct caataatagg     540
tccgggttta tctcgcaccc ccgcggtttt tcccccacg  attttcccaa catatacagc     600 atcatgccg  ccacgccgag cttgactgag ctccttctca agggcattga aggacaagat     660
tttagcgaca tgttggggtg ttttatgttc ttccggcgga ggtcggcttt tcctccccgg     720
ctccgaaaag tgactgtgga gcgctgccac actccgctca gcttcctcac acggatcatc     780
aaccatccaa gcatcgaaga tgtcaccctc tcttcggtct ctctcatttt ggatcgatct     840
gagggcattg atgcgaggcg gtattatatc cgtaagtggc aggacttctt ggaagctttc     900
agtgatatat actacgacgg cgaggagact cgtaagcggt tgactgtggg cgagttgtgg     960
gaacgtggca atctggctac gattgacgtt aaccatttgc ttggagtgac tctattggat    1020
ccaaactaa                                                            1029
```

<210> SEQ ID NO 5
<211> LENGTH: 342
<212> TYPE: PRT
<213> ORGANISM: Paecilomyces divaricatus

<400> SEQUENCE: 5

```
Met Gly Tyr Leu Glu Asn Leu Pro Ala Glu Leu Leu Phe Leu Ile Val
1               5                   10                  15

Asp Gln Leu Asp Arg Tyr Asp Leu Met Asn Leu Arg Val Val His Arg
            20                  25                  30

Arg Phe Ser Phe Val Asn Pro Arg Val Phe Lys Val Met Arg Phe Tyr
        35                  40                  45

Asn Glu Pro Thr Val Pro Val Lys Leu Arg Lys Leu Leu Lys Arg Glu
    50                  55                  60

Asp Met Arg Ser Ala Leu Asp Glu Ile Ile Phe Ser Thr Asp Ser Leu
65                  70                  75                  80

Phe Arg Gly Tyr Asn Arg His Asp Ala Ala Leu Arg Leu Lys Arg Val
                85                  90                  95

Ala Arg Leu Leu Ala Asn His Asp Asp Val Asn Ile Lys Thr Val His
            100                 105                 110

Leu Val Gly Asp Ser Gly Gly Leu Gly Leu Leu Leu Arg Tyr Phe Ala
        115                 120                 125

Glu Ala Gly Ile Arg Ser Leu Arg Tyr Leu Ser Gly Ala Ile Ile Phe
    130                 135                 140

Arg His His Glu Ile Asn Glu Glu Trp Leu Pro His Leu Met Asp Glu
145                 150                 155                 160

Ser Gly Val Leu Glu Val Leu Gly Gly Leu Glu Arg Leu Asp Leu Thr
                165                 170                 175

Leu Asn Asn Arg Ser Gly Phe Ile Ser His Pro Arg Gly Phe Ser Pro
            180                 185                 190

His Asp Phe Pro Asn Ile Tyr Ser Ile Met Ala Ala Thr Pro Ser Leu
        195                 200                 205

Thr Glu Leu Leu Leu Lys Gly Ile Glu Gly Gln Asp Phe Ser Asp Met
    210                 215                 220

Leu Gly Cys Phe Met Phe Arg Arg Arg Ser Ala Phe Pro Pro Arg
225                 230                 235                 240

Leu Arg Lys Val Thr Val Glu Arg Cys His Thr Pro Leu Ser Phe Leu
                245                 250                 255
```

-continued

```
Thr Arg Ile Ile Asn His Pro Ser Ile Glu Asp Val Thr Leu Ser Ser
            260                 265                 270

Val Ser Leu Ile Leu Asp Arg Ser Glu Gly Ile Asp Ala Arg Arg Tyr
        275                 280                 285

Tyr Ile Arg Lys Trp Gln Asp Phe Leu Glu Ala Phe Ser Asp Ile Tyr
    290                 295                 300

Tyr Asp Gly Glu Glu Thr Arg Lys Arg Leu Thr Val Gly Glu Leu Trp
305                 310                 315                 320

Glu Arg Gly Asn Leu Ala Thr Ile Asp Val Asn His Leu Leu Gly Val
                325                 330                 335

Thr Leu Leu Asp Pro Asn
            340
```

<210> SEQ ID NO 6
<211> LENGTH: 732
<212> TYPE: DNA
<213> ORGANISM: Paecilomyces divaricatus

<400> SEQUENCE: 6

```
atgctgacca ccgtcaagac gcccaatgcc gtacagaaca tcgagatcct cgcgcgccgg      60
tatggggaca ttcaagccaa cgccgccaac atcaacaccc cgtgcgattg catccatggc     120
atggtgcagg tgatggggaa gctgccagat cactacccgg tctcctttga tacgatcctg     180
agtttgggcg ccgatatcac cacccagtgt gcgcacatgg tggcctgcga gcactgccgg     240
acccactggc atgccatcat caccctacag tgcgtcctcg atctggggtt ggccctgtat     300
gagggggcct tttccgccta tgcattggga gaaggggatc tgaggagccc ggagcggttg     360
ggcaccgggc ggagatcccg ctcctcgacg ctgtcccttc ctcggccacc tggctcctcc     420
tccgatggag cagacggtct ggccagcgcg gacgatttcc ccgggacgat gaacgggccc     480
ccggtctgtt gcaccagccc gatgacatgg ggcgatatcg agatccatga agaagacgcg     540
caactgctcg ccggcatgct cctgcgccgg cgattggcgg acctgggggc cctgatcggc     600
gagctgaaac tcatcctgga gaatgtgtgg catcggaatc gcccccaaca atccttctcg     660
ctgcaggagt gcgaggactc tctgatggtg tcgatggacc ggctagtgac gttggtcggg     720
cttttgagat ga                                                         732
```

<210> SEQ ID NO 7
<211> LENGTH: 243
<212> TYPE: PRT
<213> ORGANISM: Paecilomyces divaricatus

<400> SEQUENCE: 7

```
Met Leu Thr Thr Val Lys Thr Pro Asn Ala Val Gln Asn Ile Glu Ile
1               5                   10                  15

Leu Ala Arg Arg Tyr Gly Asp Ile Gln Ala Asn Ala Ala Asn Ile Asn
            20                  25                  30

Thr Pro Cys Asp Cys Ile His Gly Met Val Gln Val Met Gly Lys Leu
        35                  40                  45

Pro Asp His Tyr Pro Val Ser Phe Asp Thr Ile Leu Ser Leu Gly Ala
    50                  55                  60

Asp Ile Thr Thr Gln Cys Ala His Met Val Ala Cys Glu His Cys Arg
65                  70                  75                  80

Thr His Trp His Ala Ile Ile Thr Leu Gln Cys Val Leu Asp Leu Gly
                85                  90                  95

Leu Ala Leu Tyr Glu Gly Ala Phe Ser Ala Tyr Ala Leu Gly Glu Gly
```

```
            100                 105                 110
Asp Leu Arg Ser Pro Glu Arg Leu Gly Thr Gly Arg Arg Ser Arg Ser
            115                 120                 125

Ser Thr Leu Ser Leu Pro Arg Pro Gly Ser Ser Asp Gly Ala
        130                 135                 140

Asp Gly Leu Ala Ser Ala Asp Asp Phe Pro Gly Thr Met Asn Gly Pro
145                 150                 155                 160

Pro Val Cys Cys Thr Ser Pro Met Thr Trp Gly Asp Ile Glu Ile His
                165                 170                 175

Glu Glu Asp Ala Gln Leu Leu Ala Gly Met Leu Leu Arg Arg Arg Leu
                180                 185                 190

Ala Asp Leu Gly Ala Leu Ile Gly Glu Leu Lys Leu Ile Leu Glu Asn
                195                 200                 205

Val Trp His Arg Asn Arg Pro Gln Gln Ser Phe Ser Leu Gln Glu Cys
            210                 215                 220

Glu Asp Ser Leu Met Val Ser Met Asp Arg Leu Val Thr Leu Val Gly
225                 230                 235                 240

Leu Leu Arg

<210> SEQ ID NO 8
<211> LENGTH: 1047
<212> TYPE: DNA
<213> ORGANISM: Paecilomyces divaricatus

<400> SEQUENCE: 8
atgtcgcaca agctttctct gaatgatggc gtcttaatgc ccacagtaag tactaccaga      60
tcctttttgt cattttgaat tgcatggtgc ttatggaata ctgcttttt agcttgcatt      120 tggcgtgggc actgctttct tgaaacgttc tggatcggat gccctgcatc gaccgacggt     180
ggatgccgtc aaagaagccc tccgtgtcgg ctatcgccac ctcgataccg ctgagatgta    240
caatacagag ctcgaagtgg gtgcggccat ccacgaaagc attgcggagg cattgtcca    300 gggaagagat gagctgttca tcacgacaaa ggtctccagt gacttcctta acatctccaa    360
gtcgattgat gtcagcctcc aaaaattgaa attagattac gttgacgcgt aagtcattcc    420 ccctgcaga gaaatagctc ctatcgatcc tagccttgat ctgtctacag gtatctcatt    480 catacccgt actgggcgga atccgacgac gacctgcaga aggcctggaa aggcatggag    540
gaggtcaagg ccagtgggaa ggcccgaacc attggtgtct cgaatttcca gtcgacgcat    600
ctccggaccg ttttggcaac cgcgcaaaca ccaccctcgg tgaatcagct cgaattccac    660
ccatatctct cggttcgaga tgcaacgac tatctcttca gcctacgaga caatatgcgg    720
gacatcacca tctccgctta tggcgccctg gcgccaatca aaggaatat cccgggccca    780 ctcgacgaga ctttgaaaga agtggccaac aggtatggcg tgggcactga tctggtgtgt    840
ctcagatggt gtattgagca gggggttgcc acgatcacaa ccagtcgcca tgaggaccga    900 atgaagggt atctcagggt cttcgacttc cagatcacac cggacgaggt gatgcagatc    960
ggagcttcgg cccaggcatg tctggggac aaagagcagc ccctcactcg gattgaaaaa    1020
taccatatgg ctcagaaaca tacctag                                        1047

<210> SEQ ID NO 9
<211> LENGTH: 305
<212> TYPE: PRT
<213> ORGANISM: Paecilomyces divaricatus

<400> SEQUENCE: 9
```

```
Met Ser His Lys Leu Ser Leu Asn Asp Gly Val Leu Met Pro Thr Leu
1               5                   10                  15

Ala Phe Gly Val Gly Thr Ala Phe Leu Lys Arg Ser Gly Ser Asp Ala
            20                  25                  30

Leu His Arg Pro Thr Val Asp Ala Val Lys Glu Ala Leu Arg Val Gly
            35                  40                  45

Tyr Arg His Leu Asp Thr Ala Glu Met Tyr Asn Thr Glu Leu Glu Val
50                  55                  60

Gly Ala Ala Ile His Glu Ser Ile Ala Glu Gly Ile Val Gln Gly Arg
65                  70                  75                  80

Asp Glu Leu Phe Ile Thr Thr Lys Val Ser Ser Asp Phe Leu Asn Ile
            85                  90                  95

Ser Lys Ser Ile Asp Val Ser Leu Gln Lys Leu Lys Leu Asp Tyr Val
            100                 105                 110

Asp Ala Tyr Leu Ile His Thr Pro Tyr Trp Ala Glu Ser Asp Asp Asp
            115                 120                 125

Leu Gln Lys Ala Trp Lys Gly Met Glu Glu Val Lys Ala Ser Gly Lys
    130                 135                 140

Ala Arg Thr Ile Gly Val Ser Asn Phe Gln Ser Thr His Leu Arg Thr
145                 150                 155                 160

Val Leu Ala Thr Ala Gln Thr Pro Pro Ser Val Asn Gln Leu Glu Phe
                165                 170                 175

His Pro Tyr Leu Ser Val Arg Asp Gly Asn Asp Tyr Leu Phe Ser Leu
            180                 185                 190

Arg Asp Asn Met Arg Asp Ile Thr Ile Ser Ala Tyr Gly Ala Leu Ala
            195                 200                 205

Pro Ile Thr Arg Asn Ile Pro Gly Pro Leu Asp Glu Thr Leu Lys Glu
    210                 215                 220

Val Ala Asn Arg Tyr Gly Val Gly Thr Asp Leu Val Cys Leu Arg Trp
225                 230                 235                 240

Cys Ile Glu Gln Gly Val Ala Thr Ile Thr Thr Ser Arg His Glu Asp
                245                 250                 255

Arg Met Lys Gly Tyr Leu Arg Val Phe Asp Phe Gln Ile Thr Pro Asp
            260                 265                 270

Glu Val Met Gln Ile Gly Ala Ser Ala Gln Ala Cys Leu Gly Asp Lys
    275                 280                 285

Glu Gln Pro Leu Thr Arg Ile Glu Lys Tyr His Met Ala Gln Lys His
    290                 295                 300

Thr
305

<210> SEQ ID NO 10
<211> LENGTH: 81
<212> TYPE: DNA
<213> ORGANISM: Paecilomyces divaricatus

<400> SEQUENCE: 10
atggtaagaa gaaaataatg agaatgtatt aagctgattc tcttctagat cggctctcgt    60
gctactgatg gcacaagtta g                                             81

<210> SEQ ID NO 11
<211> LENGTH: 11
<212> TYPE: PRT
<213> ORGANISM: Paecilomyces divaricatus
```

<400> SEQUENCE: 11

Met Ile Gly Ser Arg Ala Thr Asp Gly Thr Ser
1               5                   10

<210> SEQ ID NO 12
<211> LENGTH: 1923
<212> TYPE: DNA
<213> ORGANISM: Paecilomyces divaricatus

<400> SEQUENCE: 12

```
atgagcagct ataaattccc cgtcgacctc aagcagttca agcagctcaa gcttgaccca      60
aaaagcccac agctttctgc tcagcagaag aacgacctcc tgcataacat caacattttc     120
agagatgcaa tcatcgcatt cacggccacg ggtgccgccc gtggactcgc gggccacact     180
ggggggtccgt tcgacactgc cccagaggtc tgcatcttgc tcgccttcat gaacgcgaac     240
cccgatggtt tcgttgatgc cctgtacgac gaagctggcc atcgggttgc cacgcaatac     300
ttgcttgctg cgctggacgg aaagattgac cccgaccacc tgctgaacta ccgcgctgcc     360
gattcgaaac tcccgggcca ccctgagctt ggcctgacgc cgggcatcaa gttcagctcg     420
ggtcgtcttg gtcacatgtg ggccatgtgc aacggtatct ccatggccca aaggataaag     480
aacgtcctgc tgctgggatc ggatggctcc cagcaggaag gaaacgacgc cgaggccgcg     540
cgcattgccg ttgccaaaaa cctgaaggtg aagctgttca tcgacaacaa cgacgtcaca     600
atcgccggac atccttcgat atacttgaag ggctacgaga tcgctcgtac gctcgagggg     660
cacggcttga aggtcatccg cgcccagggt gagaatctgg attcgcttta cggggcgatg     720
tgtgaaatca tcaactacaa cggccctgcc gctgttgtgg tagaccggaa gatggccgca     780
ggcatcgaag aaattgaggg agagacccac gctcacgatg tcattccggt cgatatcgct     840
cgcaaatacc ttaccaagcg tggatacagc aaggagcagc ttgctttcta cgaccagatc     900
aagcctggat cgaacccgca ccagtaccag ggctcaacca aggagaaggg tgcgaaccgt     960
gcgatttttg gtgaagccgt gaactccgtg ctcgacggcc tcagcaagga gagcgtgtc     1020
cgtcgggtca tggtcatcga ttctgacctt gcgggctcta ccggcctgaa ggcaattcaa    1080
tcgaagcacc ccgaggtgtt cgttgcatcc ggtgtcatgg agcggggcaa cttctccgcc    1140
gctgctggct tcggattcgg cagcaacggc gagcgtcagg gtgttttctc tactttctcg    1200
gctttcctgg agatgtgcgt ctcggaaatt accatggcac gcttgaatcg ctgcaccgtc    1260
ctctcccact tctcccacag cggtgttgat gagatggccg acaacacctg ccactttggt    1320
ctgaatctct tctttgcaga caacggcctg atggatgccg agagcacatc gttgtacttc    1380
cccgccgacg gtgagcagat gaaggcggtc gtcaacaagg tcttttggga taagagcatg    1440
cgtttcatct tctcaacgcg ttccaaggtt ccttacatcc tcaaagaagg taccgaccag    1500
aagctctatg gcgacggcta cgagtttgtc ccgggcaagg aagaagtcat ccgcaagggt    1560
tccgccggct atgttgtctc gtacggtgat atgctctacc gctcgctcga tgccgttgag    1620
cgcctgcgca aggagggcct tgatgttggc ctcatcaata agcccacact gaatattgtc    1680
gatgaggaca ccatcaaggt ttacggatcg actccgttcg ttgtggtcgt cgagtcaatt    1740
gctcagaaga cgggtcttgg ctcccgcctg gcagtcacc ttcttgagcg caagcttacg    1800
cccaagttca aggcgattgg tgccgtgagg gagggctctg gcggcttgta cgagcagatt    1860
aatgcccagg gtcttggacc aaacgacatc attgcggcag tgaaggaggt cagtgggaaa    1920
taa                                                                 1923
```

<210> SEQ ID NO 13
<211> LENGTH: 640
<212> TYPE: PRT
<213> ORGANISM: Paecilomyces divaricatus

<400> SEQUENCE: 13

```
Met Ser Ser Tyr Lys Phe Pro Val Asp Leu Lys Gln Phe Lys Gln Leu
1               5                   10                  15

Lys Leu Asp Pro Lys Ser Pro Gln Leu Ser Ala Gln Lys Asn Asp
            20                  25                  30

Leu Leu His Asn Ile Asn Ile Phe Arg Asp Ala Ile Ile Ala Phe Thr
            35                  40                  45

Ala Thr Gly Ala Ala Arg Gly Leu Ala Gly His Thr Gly Gly Pro Phe
        50                  55                  60

Asp Thr Ala Pro Glu Val Cys Ile Leu Ala Phe Met Asn Ala Asn
65                  70                  75                  80

Pro Asp Gly Phe Val Asp Ala Leu Tyr Asp Glu Ala Gly His Arg Val
                85                  90                  95

Ala Thr Gln Tyr Leu Leu Ala Ala Leu Asp Gly Lys Ile Asp Pro Asp
            100                 105                 110

His Leu Leu Asn Tyr Arg Ala Ala Asp Ser Lys Leu Pro Gly His Pro
        115                 120                 125

Glu Leu Gly Leu Thr Pro Gly Ile Lys Phe Ser Ser Gly Arg Leu Gly
    130                 135                 140

His Met Trp Ala Met Cys Asn Gly Ile Ser Met Ala His Lys Asp Lys
145                 150                 155                 160

Asn Val Leu Leu Leu Gly Ser Asp Gly Ser Gln Gln Glu Gly Asn Asp
                165                 170                 175

Ala Glu Ala Ala Arg Ile Ala Val Ala Lys Asn Leu Lys Val Lys Leu
            180                 185                 190

Phe Ile Asp Asn Asn Asp Val Thr Ile Ala Gly His Pro Ser Ile Tyr
        195                 200                 205

Leu Lys Gly Tyr Glu Ile Ala Arg Thr Leu Glu Gly His Gly Leu Lys
    210                 215                 220

Val Ile Arg Ala Gln Gly Glu Asn Leu Asp Ser Leu Tyr Gly Ala Met
225                 230                 235                 240

Cys Glu Ile Ile Asn Tyr Asn Gly Pro Ala Ala Val Val Asp Arg
                245                 250                 255

Lys Met Ala Ala Gly Ile Glu Glu Ile Glu Gly Glu Thr His Ala His
            260                 265                 270

Asp Val Ile Pro Val Asp Ile Ala Arg Lys Tyr Leu Thr Lys Arg Gly
        275                 280                 285

Tyr Ser Lys Glu Gln Leu Ala Phe Tyr Asp Gln Ile Lys Pro Gly Ser
    290                 295                 300

Asn Pro His Gln Tyr Gln Gly Ser Thr Lys Lys Gly Ala Asn Arg
305                 310                 315                 320

Ala Ile Phe Gly Glu Ala Val Asn Ser Val Leu Asp Gly Leu Ser Lys
                325                 330                 335

Glu Glu Arg Val Arg Arg Val Met Val Ile Asp Ser Asp Leu Ala Gly
            340                 345                 350

Ser Thr Gly Leu Lys Ala Ile Gln Ser Lys His Pro Glu Val Phe Val
        355                 360                 365

Ala Ser Gly Val Met Glu Arg Gly Asn Phe Ser Ala Ala Ala Gly Phe
    370                 375                 380
```

Gly Phe Gly Ser Asn Gly Glu Arg Gln Gly Val Phe Ser Thr Phe Ser
385                 390                 395                 400

Ala Phe Leu Glu Met Cys Val Ser Glu Ile Thr Met Ala Arg Leu Asn
                405                 410                 415

Arg Cys Thr Val Leu Ser His Phe Ser His Ser Gly Val Asp Glu Met
            420                 425                 430

Ala Asp Asn Thr Cys His Phe Gly Leu Asn Leu Phe Phe Ala Asp Asn
            435                 440                 445

Gly Leu Met Asp Ala Glu Ser Thr Ser Leu Tyr Phe Pro Ala Asp Gly
        450                 455                 460

Glu Gln Met Lys Ala Val Val Asn Lys Val Phe Trp Asp Lys Ser Met
465                 470                 475                 480

Arg Phe Ile Phe Ser Thr Arg Ser Lys Val Pro Tyr Ile Leu Lys Glu
                485                 490                 495

Gly Thr Asp Gln Lys Leu Tyr Gly Asp Gly Tyr Glu Phe Val Pro Gly
            500                 505                 510

Lys Glu Glu Val Ile Arg Lys Gly Ser Ala Gly Tyr Val Val Ser Tyr
            515                 520                 525

Gly Asp Met Leu Tyr Arg Ser Leu Asp Ala Val Glu Arg Leu Arg Lys
        530                 535                 540

Glu Gly Leu Asp Val Gly Leu Ile Asn Lys Pro Thr Leu Asn Ile Val
545                 550                 555                 560

Asp Glu Asp Thr Ile Lys Val Tyr Gly Ser Thr Pro Phe Val Val
                565                 570                 575

Val Glu Ser Ile Ala Gln Lys Thr Gly Leu Gly Ser Arg Leu Gly Ser
            580                 585                 590

His Leu Leu Glu Arg Lys Leu Thr Pro Lys Phe Lys Ala Ile Gly Ala
        595                 600                 605

Val Arg Glu Gly Ser Gly Gly Leu Tyr Glu Gln Ile Asn Ala Gln Gly
        610                 615                 620

Leu Gly Pro Asn Asp Ile Ile Ala Ala Val Lys Glu Val Ser Gly Lys
625                 630                 635                 640

<210> SEQ ID NO 14
<211> LENGTH: 1635
<212> TYPE: DNA
<213> ORGANISM: Paecilomyces divaricatus

<400> SEQUENCE: 14
atggatctgc tgaaagagct ggatgcgccc tctctggcgc cctcgttgtt gggcaccggc        60
gtcgtcctgg tcgtcctgta cttcctcacc gtctccatcc agaaccgaat tccccgttc        120 gatgccccg tggtgtctca cgccaaagga ttcctcgcgg ctctgcagga gggcaaagcc        180
aaggtgagtg actttctgtc atcgtggctc gatcatgatg gatgaatcct gacgagactg        240
cagtaccgca tcaacccctt catcctcaac acgccccatc atcctacggt catcctcccc        300
cggaaatggt gggaggagct caagtcgctg cccgagagcc acatctcgtt cgaagccgaa        360
cggctgtatc gctggggcaa gggcaatccg atcgccctcg tcgaccatgt caccatcgag        420
accaccaaga acgagctgac ccgtcacact gcgcgctcct tcccctgct gctggatgag        480 accgtctacg cggtcgacaa gcacatcggg ccctgcgtgg actggacgcc catcaccgtc        540
tatcccacgg acctgcagct catcgccctg ctgagcagcc gcacctttgt cggcctgccg        600
ctcagtcgca acgagcgctg gctggagatc atgatccgct acaccatcct cagtaaggcc        660

-continued

```
gccgcgcggg ccctgtggcc gtatcccttc ctgctgcggc cgatcctcca gcgctttgcg    720
ccccagtcga aagagttgga gaagcagcgc aaggaggcca gcgccctggt gcgtcccatc    780
ctcgagcagc ggctggccga cctgaagcgc ccggacttca gcccccccaa cgacatgatg    840
cagtgggtgc tgcataactg taccccggcg gagcgcgagg atatcgactt cctcgtccag    900
cagcagctca cgctgagcat cgtctcgata cacaccaccg ctcacaacct gacccactgc    960
atcttcgacc tggccgccca tcccgagtgc atcgagccgc tgcgccagga gttcctgccg   1020
ctgctccggg agacgaacgg ccagatcgac aagcagctcc tgaccaagtg caacaagctg   1080
gacagcttct gcaaggaatc ccagcggttc tgcccgccgg ggcttatcgt catgtcccgc   1140
aagatcatga gcgacatccc catgagcaac ggcaccatcc tgcccaaggg cctcttcgtg   1200
gccacctcca actacgatgc cacgagcgac gagtccgtcc tggggaatcc ggaccagttc   1260
gacgccttcc ggtacgagcg gatgcgcctg cagccgcagc agcggaacct gcaccagctc   1320
gtgtcgacca ggtgagctct tttttcaacc cccatcctat tccttcttcg caatgaatga   1380 cccctacta agagcacatg cagcacgagt gaactctcgt ttggttttgg cacccacgcc   1440
tgtcccggcc gcttctttgc cgcctttgag atcaagatga tcctcatcta cttgctgctc   1500
aactacgacc tcaagttcca ggaggggtc ccgccacccc ggaatgagat cctcgtcacc   1560
gccgtcatgc cttctttcca gggcaaggtg atgatgaagc ggcgacgcga aagatcgga   1620 tggcatgtcg actga                                                   1635
```

<210> SEQ ID NO 15
<211> LENGTH: 500
<212> TYPE: PRT
<213> ORGANISM: Paecilomyces divaricatus

<400> SEQUENCE: 15

```
Met Asp Leu Leu Lys Glu Leu Asp Ala Pro Ser Leu Ala Pro Ser Leu
1               5                   10                  15

Leu Gly Thr Gly Val Val Leu Val Val Leu Tyr Phe Leu Thr Val Ser
            20                  25                  30

Ile Gln Asn Arg Ile Pro Pro Phe Asp Ala Pro Val Val Ser His Ala
        35                  40                  45

Lys Gly Phe Leu Ala Ala Leu Gln Glu Gly Lys Ala Lys Tyr Arg Asn
    50                  55                  60

Gln Pro Phe Ile Leu Asn Thr Pro His His Pro Thr Val Ile Leu Pro
65                  70                  75                  80

Arg Lys Trp Trp Glu Glu Leu Lys Ser Leu Pro Glu Ser His Ile Ser
                85                  90                  95

Phe Glu Ala Glu Arg Leu Tyr Arg Trp Gly Lys Gly Asn Pro Ile Ala
            100                 105                 110

Leu Val Asp His Val Thr Ile Glu Thr Thr Lys Asn Glu Leu Thr Arg
        115                 120                 125

His Thr Ala Arg Ser Phe Pro Leu Leu Leu Asp Glu Thr Val Tyr Ala
    130                 135                 140

Val Asp Lys His Ile Gly Pro Cys Val Asp Trp Thr Pro Ile Thr Val
145                 150                 155                 160

Tyr Pro Thr Asp Leu Gln Leu Ile Ala Leu Leu Ser Ser Arg Thr Phe
                165                 170                 175

Val Gly Leu Pro Leu Ser Arg Asn Glu Arg Trp Leu Glu Ile Met Ile
            180                 185                 190

Arg Tyr Thr Ile Leu Ser Lys Ala Ala Ala Arg Ala Leu Trp Pro Tyr
```

195                 200                 205
Pro Phe Leu Leu Arg Pro Ile Leu Gln Arg Phe Ala Pro Gln Ser Lys
    210                 215                 220

Glu Leu Glu Lys Gln Arg Lys Glu Ala Ser Ala Leu Val Arg Pro Ile
225                 230                 235                 240

Leu Glu Gln Arg Leu Ala Asp Leu Lys Arg Pro Asp Phe Lys Pro Pro
                245                 250                 255

Asn Asp Met Met Gln Trp Val Leu His Asn Cys Thr Pro Ala Glu Arg
            260                 265                 270

Glu Asp Ile Asp Phe Leu Val Gln Gln Gln Leu Thr Leu Ser Ile Val
        275                 280                 285

Ser Ile His Thr Thr Ala His Asn Leu Thr His Cys Ile Phe Asp Leu
    290                 295                 300

Ala Ala His Pro Glu Cys Ile Glu Pro Leu Arg Gln Glu Phe Leu Pro
305                 310                 315                 320

Leu Leu Arg Glu Thr Asn Gly Gln Ile Asp Lys Gln Leu Leu Thr Lys
                325                 330                 335

Cys Asn Lys Leu Asp Ser Phe Cys Lys Glu Ser Gln Arg Phe Cys Pro
            340                 345                 350

Pro Gly Leu Ile Val Met Ser Arg Lys Ile Met Ser Asp Ile Pro Met
        355                 360                 365

Ser Asn Gly Thr Ile Leu Pro Lys Gly Leu Phe Val Ala Thr Ser Asn
    370                 375                 380

Tyr Asp Ala Thr Ser Asp Glu Ser Val Leu Gly Asn Pro Asp Gln Phe
385                 390                 395                 400

Asp Ala Phe Arg Tyr Glu Arg Met Arg Leu Gln Pro Gln Gln Arg Asn
                405                 410                 415

Leu His Gln Leu Val Ser Thr Ser Thr Ser Glu Leu Ser Phe Gly Phe
            420                 425                 430

Gly Thr His Ala Cys Pro Gly Arg Phe Phe Ala Ala Phe Glu Ile Lys
        435                 440                 445

Met Ile Leu Ile Tyr Leu Leu Leu Asn Tyr Asp Leu Lys Phe Gln Glu
    450                 455                 460

Gly Val Pro Pro Pro Arg Asn Glu Ile Leu Val Thr Ala Val Met Pro
465                 470                 475                 480

Ser Phe Gln Gly Lys Val Met Met Lys Arg Arg Glu Lys Ile Gly
                485                 490                 495

Trp His Val Asp
            500

<210> SEQ ID NO 16
<211> LENGTH: 1509
<212> TYPE: DNA
<213> ORGANISM: Paecilomyces divaricatus

<400> SEQUENCE: 16
atgtcggcag aagcagagaa gcagtcctcc tctccggccg actccagcct ccagaccatc    60
catgatgacc gcgaccaacc cccgggcgat gcggaggatc cgaccctcat cacctgggat   120
ggacccgacg acccagccaa ccccaagaac tggtcccggc ggcgtaaatg gcggcgacg    180 atggtcgtgt ccggcttcaa cttcatctcg ccgctggcca gcgccatgat cgccccgtgt   240
ttgcccgcgc tggctgccga gctggacatc acctcctccg tcgagcagag catggcgctc   300
agcgtcttcg tcctgggcta cgcggtcggc ccgctcgtgg tcggtcccttt gtccgagctg   360

-continued

```
tacgggcgcg tgcccgtgtt gcagacgagc aacctggtgt ttctgctgtt caacctcgcc    420
tgtggcctgg cccggaccaa gggcgagatg atcgccttcc gcttcatcgc cggcctgggg    480
ggctccgcgc cccaggccac cggcggcggc gtcctggggg atctctgggc caccgaggag    540
cgtggccgcg cgctggcctt ctacagcctg gcgccgctgc tggggccggc cgttgggccc    600
atcgcgggcg gcttcgtcgc ggagaatacg agctggcgct ggatcttcta cgccaccacc    660
atctccaacg gggtcgtcat gctgctgggc ttcctcctcc tgcaggagac ccgggcctcc    720
gtcctgctgg agcgcaagaa cgccgccgc atccgtgaga ccggcagcaa ggcgtggcat     780
accgagactg ataacccgga tcacaccctg cgcaacatca tcctgaccgc gctcaaccgg    840
cccttccgcc tgctcttcac ccagccgatc gtgcaggtgc tggccgtgta cctggcctac    900
atctacggca tcgtgtactt ggtgctcgcc agtttcccgg atctctggac ctcccccgat    960
cactacggtg agtcggtcgg catcggcgga ctgaactaca tcgccctcgc gtgtgggttc   1020
ttgctgggcg cctatctgtg tgcgcccacg caggaccgga tctaccgtcg gttgaaggat   1080
cgcaacggcg gcgtgggccg gccggaatac cgcatcccgc tgatgatccc cagtgccatc   1140
ctcgtgcccg tcggtctttt catctacggc tggaccgccg agtaccgaac gttctggatc   1200
ggcccggaca tcggcatcgc cctgtatgcc gcgggctaca tcaccagctt ccagtgcgtc   1260
caggtctata tcgtcgacac gtacaccaat tatgcggcat cggcgctggc ctcggtgacc   1320
gtgctgcgca gtctctgtgc cttcaccttt ccgctgtttg ccccgaagat gtatgatgcg   1380
ctggggtatg gctggggaaa ctcgatgctg gccttcatcg ccatggggct cggatggccg   1440
ggtccgtttg tgttgtggcg ctatgggcag gctctgcgag agcgcagtcc atatgccgca   1500
gagatataa                                                           1509
```

<210> SEQ ID NO 17
<211> LENGTH: 502
<212> TYPE: PRT
<213> ORGANISM: Paecilomyces divaricatus

<400> SEQUENCE: 17

```
Met Ser Ala Glu Ala Glu Lys Gln Ser Ser Pro Ala Asp Ser Ser
1               5                   10                  15

Leu Gln Thr Ile His Asp Asp Arg Asp Gln Pro Pro Gly Asp Ala Glu
                20                  25                  30

Asp Pro Thr Leu Ile Thr Trp Asp Gly Pro Asp Pro Ala Asn Pro
            35                  40                  45

Lys Asn Trp Ser Arg Arg Arg Lys Trp Ala Ala Thr Met Val Val Ser
        50                  55                  60

Gly Phe Asn Phe Ile Ser Pro Leu Ala Ser Ala Met Ile Ala Pro Cys
65                  70                  75                  80

Leu Pro Ala Leu Ala Ala Glu Leu Asp Ile Thr Ser Ser Val Glu Gln
                85                  90                  95

Ser Met Ala Leu Ser Val Phe Val Leu Gly Tyr Ala Val Gly Pro Leu
            100                 105                 110

Val Val Gly Pro Leu Ser Glu Leu Tyr Gly Arg Val Pro Val Leu Gln
        115                 120                 125

Thr Ser Asn Leu Val Phe Leu Phe Asn Leu Ala Cys Gly Leu Ala
    130                 135                 140

Arg Thr Lys Gly Glu Met Ile Ala Phe Arg Phe Ile Ala Gly Leu Gly
145                 150                 155                 160

Gly Ser Ala Pro Gln Ala Thr Gly Gly Gly Val Leu Gly Asp Leu Trp
```

165                 170                 175
Ala Thr Glu Glu Arg Gly Arg Ala Leu Ala Phe Tyr Ser Leu Ala Pro
            180                 185                 190

Leu Leu Gly Pro Ala Val Gly Pro Ile Ala Gly Gly Phe Val Ala Glu
            195                 200                 205

Asn Thr Ser Trp Arg Trp Ile Phe Tyr Ala Thr Thr Ile Ser Asn Gly
            210                 215                 220

Val Val Met Leu Leu Gly Phe Leu Leu Gln Glu Thr Arg Ala Ser
225                 230                 235                 240

Val Leu Leu Glu Arg Lys Lys Arg Arg Ile Arg Glu Thr Gly Ser
            245                 250                 255

Lys Ala Trp His Thr Glu Thr Asp Asn Pro Asp His Thr Leu Arg Asn
            260                 265                 270

Ile Ile Leu Thr Ala Leu Asn Arg Pro Phe Arg Leu Leu Phe Thr Gln
            275                 280                 285

Pro Ile Val Gln Val Leu Ala Val Tyr Leu Ala Tyr Ile Tyr Gly Ile
            290                 295                 300

Val Tyr Leu Val Leu Ala Ser Phe Pro Asp Leu Trp Thr Ser Pro Asp
305                 310                 315                 320

His Tyr Gly Glu Ser Val Gly Ile Gly Gly Leu Asn Tyr Ile Ala Leu
            325                 330                 335

Ala Cys Gly Phe Leu Leu Gly Ala Tyr Leu Cys Ala Pro Thr Gln Asp
            340                 345                 350

Arg Ile Tyr Arg Arg Leu Lys Asp Arg Asn Gly Gly Val Gly Arg Pro
            355                 360                 365

Glu Tyr Arg Ile Pro Leu Met Ile Pro Ser Ala Ile Leu Val Pro Val
370                 375                 380

Gly Leu Phe Ile Tyr Gly Trp Thr Ala Glu Tyr Arg Thr Phe Trp Ile
385                 390                 395                 400

Gly Pro Asp Ile Gly Ile Ala Leu Tyr Ala Ala Gly Tyr Ile Thr Ser
            405                 410                 415

Phe Gln Cys Val Gln Val Tyr Ile Val Asp Thr Tyr Thr Asn Tyr Ala
            420                 425                 430

Ala Ser Ala Leu Ala Ser Val Thr Val Leu Arg Ser Leu Cys Ala Phe
            435                 440                 445

Thr Phe Pro Leu Phe Ala Pro Lys Met Tyr Asp Ala Leu Gly Tyr Gly
            450                 455                 460

Trp Gly Asn Ser Met Leu Ala Phe Ile Ala Met Gly Leu Gly Trp Pro
465                 470                 475                 480

Gly Pro Phe Val Leu Trp Arg Tyr Gly Gln Ala Leu Arg Glu Arg Ser
            485                 490                 495

Pro Tyr Ala Ala Glu Ile
            500

<210> SEQ ID NO 18
<211> LENGTH: 952
<212> TYPE: DNA
<213> ORGANISM: Paecilomyces divaricatus

<400> SEQUENCE: 18
atgtccggac acaacaaagc ctgtctctgc ctgcccgtcg cggtggtcga cgactaccaa     60
gcgaagggca gatatgaaac ggtgctggac acgaagacat gtacgtatat acttaccgat    120
ccccatttgc gacacacatc tgcgaaatgt cccgcctaac actctttct gacggaggat     180

```
gtagacatca ctggtccgtc cgacgcctct cgcgcccttt tgctgatata cgacgccttt    240
ggatactcgc cccagctcct gcagggcgcc gatatcctgg cggcgtcgct gaatgccctg    300
gtggtggtcc cggacttctt caagggcaag gtggcctccg agtcctggtt ccccccggac    360
accgaagaaa agaaggccgt atgtccgact gaacgctgt atgcgaatct ccagctgatt     420
tctggtccag gccattggcg actggtttgc cacggcgggc aactttgccg tgcatatcga    480
accgatgaag gaactcgtcc agcagctctc gacgcagtat cccagcgtga gcggcaaatg    540
gggcgcgttc ggctactgct ggggaggcaa gatggtcgcg ttgacgtcag gtgaagggac    600
cattttcaag acatccggcc agacgcaccc agggcaagtc ccttgaccat tcccctttga    660
gatctcaatc gacactaacc atgggggtg ttgcagaatg ctctcggccg acgatgtctc     720
caagatcaac atcccccata tcatcctggc gtcgaaggac gaagatgcca ccgcggtggc    780
cgagtgcaag aaggtcctcg agggtcccgg caagacaggc ctggtaaagt cgtatccgga    840
ccagatccac ggctggatgg ccgcccgtgc caatctgaag gacgagacgg tccgcaaggc    900
gtttgaagat gggtacaaga ccgccgcgga gttttttgag cagcatcttt aa            952
```

<210> SEQ ID NO 19
<211> LENGTH: 234
<212> TYPE: PRT
<213> ORGANISM: Paecilomyces divaricatus

<400> SEQUENCE: 19

```
Met Ser Gly His Asn Lys Ala Cys Leu Cys Leu Pro Val Ala Val Val
1               5                   10                  15

Asp Asp Tyr Gln Ala Lys Gly Arg Tyr Glu Thr Val Leu Asp Thr Lys
            20                  25                  30

Thr Tyr Ile Thr Gly Pro Ser Asp Ala Ser Arg Ala Leu Leu Leu Ile
        35                  40                  45

Tyr Asp Ala Phe Gly Tyr Ser Pro Gln Leu Leu Gln Gly Ala Asp Ile
    50                  55                  60

Leu Ala Ala Ser Leu Asn Ala Leu Val Val Val Pro Asp Phe Phe Lys
65                  70                  75                  80

Gly Lys Val Ala Ser Glu Ser Trp Phe Pro Pro Asp Thr Glu Glu Lys
                85                  90                  95

Lys Ala Ala Ile Gly Asp Trp Phe Ala Thr Ala Gly Asn Phe Ala Val
            100                 105                 110

His Ile Glu Pro Met Lys Glu Leu Val Gln Gln Leu Ser Thr Gln Tyr
        115                 120                 125

Pro Ser Val Ser Gly Lys Trp Gly Ala Phe Gly Tyr Cys Trp Gly Gly
    130                 135                 140

Lys Met Val Ala Leu Thr Met Leu Ser Ala Asp Asp Val Ser Lys Ile
145                 150                 155                 160

Asn Ile Pro His Ile Ile Leu Ala Ser Lys Asp Glu Asp Ala Thr Ala
                165                 170                 175

Val Ala Glu Cys Lys Lys Val Leu Glu Gly Pro Gly Lys Thr Gly Leu
            180                 185                 190

Val Lys Ser Tyr Pro Asp Gln Ile His Gly Trp Met Ala Ala Arg Ala
        195                 200                 205

Asn Leu Lys Asp Glu Thr Val Arg Lys Ala Phe Glu Asp Gly Tyr Lys
    210                 215                 220

Thr Ala Ala Glu Phe Phe Glu Gln His Leu
225                 230
```

<210> SEQ ID NO 20
<211> LENGTH: 1599
<212> TYPE: DNA
<213> ORGANISM: Paecilomyces divaricatus

<400> SEQUENCE: 20

| | | |
|---|---|---|
| atgccctccg ccagcgagac cactcccctt ctcggggagg accagtgccc aaaatcatcc | 60 |
| caggggccca tcgtcccaga cttcaagcca ccccaagatg agctgaaagc acatagcatt | 120 |
| ttcacacggc cacaaaagat cctgatcgtc atcatcgcct ccctggctgc cttcttctcc | 180 |
| ccggtttcgt cggccattta cttcccggcg ctgggcacct tggccgatgc cctcggagtg | 240 |
| tctgtctcgt tgatcaacct caccgtgacc acgtatctgg taacgtagga ccctacatga | 300 |
| tccctctatt gttctcccgc tgaccgactt ccccaggtca tgcaagggct ggcgccctcc | 360 |
| ttcattggga gctggtccga tcgagcgggg cgacggccgc tctacatcgc gtgcttcgtc | 420 |
| atctacattg atccaacat tggactggcc ctccagacca actacgtggc tttactgatc | 480 |
| ctgcgaatgg tccagagcgc gggcagcagt ccgttggtgt ccctggccca ggcagtcgtt | 540 |
| gcggacatgg cgacctccgc cgaacgaggc cgttatatca gctatgtcac ctccggggcc | 600 |
| atcctgggcc cggctgtggg accgttgatc ggaggcatgc tgatccagtc gtttggctgg | 660 |
| cggtcggtct tttggttcct ggccatcttc gcgggcgtcg tctttctcct catgctcgcc | 720 |
| tgcctgcccg agacctgtcg cgccgtcgtg ggagatggct cgattccccc tcccacctgg | 780 |
| atccatatgt cctggctggc atatcgacac cgacgacaaa taccctaaa cggccccccg | 840 |
| atgaccatct ccacgagtcc agcagccatt cgacccggac gcaaggccag cccgaccgga | 900 |
| tccctccgcg tgatcgccga ccgggaaacc agcctgatcc tgatctacgc cggctgcgtg | 960 |
| ctggccgggt accaaatggt gtccgcgaat ctgtcggagg cactctcggc gcagtacgcc | 1020 |
| ttcaacacct tccaggtggg cttgtgcttc ctgcccttcg gcgccggggc tttcctggcg | 1080 |
| accctcacga ccggccacat cgtcgactgg aacttccggc gcttggcgcg catccaccac | 1140 |
| ctggacctcc gccagggccg ccagcaggat ctgtcccagt tcccgatcga aaaggcgcgg | 1200 |
| ctgcaggtcg gcatgccgat tgtcgggggtc ggcgccctgt cggtgctggt gtacggctgg | 1260 |
| acgatgcaag cgcgcacccc tctggccgtg ccgctggtgg cgctgttcgt ggtgggctgg | 1320 |
| acggtcagca gctcgaccaa ctcgatctcg gtcctcatcg tcgatctgca tctggacacg | 1380 |
| ccggcgaccg cgacggcggc gaataatctg gtgcggtgct ggatgggggc gctggcggtg | 1440 |
| gccgtgatgg ggccggccgt cgaggcgatc gggatcggat ggatggggac ggtgatatgc | 1500 |
| gccgtctata tcggcctgtt gcccatgctg atgctggtgt ggaggaaagg gccgacatgg | 1560 |
| cggagggaga agagagaaaa atggccgatg atgacttga | 1599 |

<210> SEQ ID NO 21
<211> LENGTH: 513
<212> TYPE: PRT
<213> ORGANISM: Paecilomyces divaricatus

<400> SEQUENCE: 21

Met Pro Ser Ala Ser Glu Thr Thr Pro Leu Leu Gly Glu Asp Gln Cys
1               5                   10                  15

Pro Lys Ser Ser Gln Gly Ala Ile Val Pro Asp Phe Lys Pro Pro Gln
            20                  25                  30

Asp Glu Leu Lys Ala His Ser Ile Phe Thr Arg Pro Gln Lys Ile Leu
        35                  40                  45

```
Ile Val Ile Ile Ala Ser Leu Ala Ala Phe Phe Ser Pro Val Ser Ser
    50                  55                  60

Ala Ile Tyr Phe Pro Ala Leu Gly Thr Leu Ala Asp Ala Leu Gly Val
65                  70                  75                  80

Ser Val Ser Leu Ile Asn Leu Thr Val Thr Thr Tyr Leu Val Met Gln
                85                  90                  95

Gly Leu Ala Pro Ser Phe Ile Gly Ser Trp Ser Asp Arg Ala Gly Arg
                100                 105                 110

Arg Pro Leu Tyr Ile Ala Cys Phe Val Ile Tyr Ile Gly Ser Asn Ile
                115                 120                 125

Gly Leu Ala Leu Gln Thr Asn Tyr Val Ala Leu Leu Ile Leu Arg Met
130                 135                 140

Val Gln Ser Ala Gly Ser Ser Pro Leu Val Ser Leu Ala Gln Ala Val
145                 150                 155                 160

Val Ala Asp Met Ala Thr Ser Ala Glu Arg Gly Arg Tyr Ile Ser Tyr
                165                 170                 175

Val Thr Ser Gly Ala Ile Leu Gly Pro Ala Val Gly Pro Leu Ile Gly
                180                 185                 190

Gly Met Leu Ile Gln Ser Phe Gly Trp Arg Ser Val Phe Trp Phe Leu
                195                 200                 205

Ala Ile Phe Ala Gly Val Val Phe Leu Leu Met Leu Ala Cys Leu Pro
210                 215                 220

Glu Thr Cys Arg Ala Val Val Gly Asp Gly Ser Ile Pro Pro Pro Thr
225                 230                 235                 240

Trp Ile His Met Ser Trp Leu Ala Tyr Arg His Arg Arg Gln Ile Pro
                245                 250                 255

Leu Asn Gly Pro Pro Met Thr Ile Ser Thr Ser Pro Ala Ala Ile Arg
                260                 265                 270

Pro Gly Arg Lys Ala Ser Pro Thr Gly Ser Leu Arg Val Ile Ala Asp
                275                 280                 285

Arg Glu Thr Ser Leu Ile Leu Ile Tyr Ala Gly Cys Val Leu Ala Gly
                290                 295                 300

Tyr Gln Met Val Ser Ala Asn Leu Ser Glu Ala Leu Ser Ala Gln Tyr
305                 310                 315                 320

Ala Phe Asn Thr Phe Gln Val Gly Leu Cys Phe Leu Pro Phe Gly Ala
                325                 330                 335

Gly Ala Phe Leu Ala Thr Leu Thr Thr Gly His Ile Val Asp Trp Asn
                340                 345                 350

Phe Arg Arg Leu Ala Arg Ile His His Leu Asp Leu Arg Gln Gly Arg
                355                 360                 365

Gln Gln Asp Leu Ser Gln Phe Pro Ile Glu Lys Ala Arg Leu Gln Val
370                 375                 380

Gly Met Pro Ile Val Gly Val Gly Ala Leu Ser Val Leu Val Tyr Gly
385                 390                 395                 400

Trp Thr Met Gln Ala Arg Thr Pro Leu Ala Val Pro Leu Val Ala Leu
                405                 410                 415

Phe Val Val Gly Trp Thr Val Ser Ser Ser Thr Asn Ser Ile Ser Val
                420                 425                 430

Leu Ile Val Asp Leu His Leu Asp Thr Pro Ala Thr Ala Thr Ala Ala
                435                 440                 445

Asn Asn Leu Val Arg Cys Trp Met Gly Ala Leu Ala Val Ala Val Met
450                 455                 460

Gly Pro Ala Val Glu Ala Ile Gly Ile Gly Trp Met Gly Thr Val Ile
```

```
                465                 470                 475                 480
            Cys Ala Val Tyr Ile Gly Leu Leu Pro Met Leu Met Leu Val Trp Arg
                            485                 490                 495
            Lys Gly Pro Thr Trp Arg Arg Glu Lys Arg Glu Lys Trp Pro Met Met
                        500                 505                 510
            Thr

<210> SEQ ID NO 22
<211> LENGTH: 2240
<212> TYPE: DNA
<213> ORGANISM: Paecilomyces divaricatus

<400> SEQUENCE: 22
```

| | | | | | |
|---|---|---|---|---|---|
| atgaacctcg | tcagtctctt | tctcaccgtc | gccttcatcc | cctctgcatt | ggcccagtcg | 60 |
| tactatccac | ccgtaccggc | cggcaccacc | gtggtcaact | cgacccagta | tcccaatgcg | 120 |
| agcattgagt | acaaagaggt | gagatttcca | tgccttctgg | atctcgtagg | tacttaaagt | 180 |
| tggtgtctat | agaccacgat | ctgcgagacc | accccggag  | tcaagggta  | cagcggatat | 240 |
| gtccggctcc | ccagcgatgt | tgtgaacagc | gtgaatggac | cgcacacgtc | caattacttc | 300 |
| ttctggttct | tcgaggcgcg | tcacgatccg | gacaaggctc | cctggccat  | ctatctcgac | 360 |
| ggcggaccgg | ggttgagctc | gctgcagggg | gctttcaccg | agacgggacc | ctgctatgtc | 420 |
| aacgaggact | ccaacagcac | ccgactcaat | ccgtggtcgt | ggaataacca | tgtcaacatg | 480 |
| ctctacattg | accagcccct | gtccacgggc | ttttcctatg | atattctggt | gaatggcacg | 540 |
| ttcgactcgc | tacgcgacaa | acagccggcc | accgagcact | cgatcaaccc | tctggctgac | 600 |
| gaggacgagc | ctgtggccaa | caacaccctat | tttgttggga | ccttctcggg | gcagaacccc | 660 |
| ggtgagacgg | ccaactctac | cgccaacggc | gcggtgggca | tttggacctt | tttgcaaact | 720 |
| tggctctccg | agtacgcctg | tcttcgaggg | taactttcgc | aacgacagct | gacgtatggg | 780 |
| atcagatttc | cggaatatcg | gacgaaggat | gatcgaatca | gtctatgggg | tgaagcggtg | 840 |
| agtgactgat | ttggaagtct | aattgcagac | cagtgcggcg | tctctgacgg | ttatgcatat | 900 |
| aaacatgaag | tttgccgggc | aattcgctac | catctacgcc | gagtactttg | aagtccaaaa | 960 |
| tgagcggatt | cgaaatggca | gccttcgacg | cgattccaac | tcgcccgaga | gtccccggat | 1020 |
| catccccgtg | gacaccgtcg | ggctcatcaa | cggttggata | gacatgtttc | gccaggccgc | 1080 |
| cggctaccta | accctcccct | tcaacaacac | ctacggactg | caggtggcca | atgcgagcgt | 1140 |
| tcagcgtcag | atcacggacg | cgtactaccg | gccgggcgga | tgcgtggacc | agacgcagaa | 1200 |
| atgccagacg | gccgccgcag | agtcagatcc | gaagaatcgc | gcgcacaacg | cgacggtcaa | 1260 |
| tgagctctgc | ttccagtccg | cctacctctg | cacgaccacc | gtccgaggtc | ccattgcggc | 1320 |
| gacacaggta | tgttgcgagg | agcaagaggt | cacggcacag | aactgactgg | ggagcagtac | 1380 |
| aatacgttcg | acatgggcca | ttggaacccc | gatccatttc | cccgagcta  | ttacattggc | 1440 |
| tatctcaacc | aacgctgggt | ccaggaggct | ctggagtcc  | ccctcaactt | taccgcacac | 1500 |
| tcatcgttgg | tcaccatgtg | tatgtgtctc | cccagcggtt | atcgaaagct | ctacacaagg | 1560 |
| ctcacaggcc | agtagcattc | ctcaaaagcg | gcgcgtttgc | cctcccctgg | gcgcttcagg | 1620 |
| atctgggaaa | gcttctcgat | cgcggggtgc | aggtgacgat | gatgtacggt | gatcgtgata | 1680 |
| tggacgtgag | ctgtaagtat | tcccttctt  | tgtgcaatga | attggtaatt | gatgggagtc | 1740 |
| aatagggatc | ggtggtgagg | aagtcagcct | ggccatcgat | cattcctcgg | ccgcggaatt | 1800 |
| cgccgccagt | ggatatgaga | gtatctccgt | caatgcaggc | tatatcggcg | gcgtaacacg | 1860 |

```
gcaatatggg cgactgtcct tttcccgcgt ctttgaagca gcgaatagag gtattcattc    1920
ccaccgtgct atctcatact gttcactatg ctgatggcga tggcggccaa atcgcagtgc    1980
cctcgtacca accggaaacc gcctatcaaa tcttcatgcg cgccatcttt gggaaggaca    2040
tcgccaccgg gtcgacagtc gtcgatgccc gctatgcctc gaccgggcca tcatccagcg    2100
ggcatatccg caacggactg cccgtggccc cgcccccgga gtgctatatc tgggccccgg    2160
cgacatgcac gccggcgcag ctgaagtcac tcggggacgg gtcggcggtc gtccgtgatt    2220
atattgtggt cgagtggtga                                                2240
```

<210> SEQ ID NO 23
<211> LENGTH: 596
<212> TYPE: PRT
<213> ORGANISM: Paecilomyces divaricatus

<400> SEQUENCE: 23

```
Met Asn Leu Val Ser Leu Phe Leu Thr Val Ala Phe Ile Pro Ser Ala
1               5                   10                  15

Leu Ala Gln Ser Tyr Tyr Pro Pro Val Pro Ala Gly Thr Thr Val Val
            20                  25                  30

Asn Ser Thr Gln Tyr Pro Asn Ala Ser Ile Glu Tyr Lys Glu Thr Thr
        35                  40                  45

Ile Cys Glu Thr Thr Pro Gly Val Lys Gly Tyr Ser Gly Tyr Val Arg
 50                  55                  60

Leu Pro Ser Asp Val Val Asn Ser Val Asn Gly Pro His Thr Ser Asn
65                  70                  75                  80

Tyr Phe Phe Trp Phe Phe Glu Ala Arg His Asp Pro Asp Lys Ala Pro
                85                  90                  95

Leu Ala Ile Tyr Leu Asp Gly Gly Pro Gly Leu Ser Ser Leu Gln Gly
            100                 105                 110

Ala Phe Thr Glu Thr Gly Pro Cys Tyr Val Asn Glu Asp Ser Asn Ser
        115                 120                 125

Thr Arg Leu Asn Pro Trp Ser Trp Asn Asn His Val Asn Met Leu Tyr
130                 135                 140

Ile Asp Gln Pro Leu Ser Thr Gly Phe Ser Tyr Asp Ile Leu Val Asn
145                 150                 155                 160

Gly Thr Phe Asp Ser Leu Arg Asp Lys Gln Pro Ala Thr Glu His Ser
                165                 170                 175

Ile Asn Pro Leu Ala Asp Glu Asp Pro Val Ala Asn Asn Thr Tyr
            180                 185                 190

Phe Val Gly Thr Phe Ser Gly Gln Asn Pro Gly Glu Thr Ala Asn Ser
        195                 200                 205

Thr Ala Asn Gly Ala Val Gly Ile Trp Thr Phe Leu Gln Thr Trp Leu
    210                 215                 220

Ser Glu Tyr Ala Cys Leu Arg Gly Phe Pro Glu Tyr Arg Thr Lys Asp
225                 230                 235                 240

Asp Arg Ile Ser Leu Trp Gly Glu Ala Thr Ser Ala Ala Ser Leu Thr
                245                 250                 255

Val Met His Ile Asn Met Lys Phe Ala Gly Gln Phe Ala Thr Ile Tyr
            260                 265                 270

Ala Glu Tyr Phe Glu Val Gln Asn Glu Arg Ile Arg Asn Gly Ser Leu
        275                 280                 285

Arg Arg Asp Ser Asn Ser Pro Glu Ser Pro Arg Ile Ile Pro Val Asp
    290                 295                 300
```

```
Thr Val Gly Leu Ile Asn Gly Trp Ile Asp Met Phe Arg Gln Ala Ala
305                 310                 315                 320

Gly Tyr Leu Thr Leu Pro Phe Asn Asn Thr Tyr Gly Leu Gln Val Ala
            325                 330                 335

Asn Ala Ser Val Gln Arg Gln Ile Thr Asp Ala Tyr Tyr Arg Pro Gly
        340                 345                 350

Gly Cys Val Asp Gln Thr Gln Lys Cys Gln Thr Ala Ala Ala Glu Ser
    355                 360                 365

Asp Pro Lys Asn Arg Ala His Asn Ala Thr Val Asn Glu Leu Cys Phe
370                 375                 380

Gln Ser Ala Tyr Leu Cys Thr Thr Thr Val Arg Gly Pro Ile Ala Ala
385                 390                 395                 400

Thr Gln Arg Leu Ser Lys Ala Leu His Lys Ala His Arg Pro Val Ala
            405                 410                 415

Phe Leu Lys Ser Gly Ala Phe Ala Leu Pro Trp Ala Leu Gln Asp Leu
        420                 425                 430

Gly Lys Leu Leu Asp Arg Gly Val Gln Val Thr Met Met Tyr Gly Asp
    435                 440                 445

Arg Asp Met Asp Val Ser Trp Ile Gly Gly Glu Glu Val Ser Leu Ala
450                 455                 460

Ile Asp His Ser Ser Ala Ala Glu Phe Ala Ala Ser Gly Tyr Glu Ser
465                 470                 475                 480

Ile Ser Val Asn Ala Gly Tyr Ile Gly Val Thr Arg Gln Tyr Gly
            485                 490                 495

Arg Leu Ser Phe Ser Arg Val Phe Glu Ala Ala Asn Arg Val Pro Ser
        500                 505                 510

Tyr Gln Pro Glu Thr Ala Tyr Gln Ile Phe Met Arg Ala Ile Phe Gly
    515                 520                 525

Lys Asp Ile Ala Thr Gly Ser Thr Val Val Asp Ala Arg Tyr Ala Ser
530                 535                 540

Thr Gly Pro Ser Ser Ser Gly His Ile Arg Asn Gly Leu Pro Val Ala
545                 550                 555                 560

Pro Pro Pro Glu Cys Tyr Ile Trp Ala Pro Ala Thr Cys Thr Pro Ala
            565                 570                 575

Gln Leu Lys Ser Leu Gly Asp Gly Ser Ala Val Val Arg Asp Tyr Ile
        580                 585                 590

Val Val Glu Trp
        595

<210> SEQ ID NO 24
<211> LENGTH: 1473
<212> TYPE: DNA
<213> ORGANISM: Paecilomyces divaricatus

<400> SEQUENCE: 24
atgccatcct catccttccc acatccgccc agccctggcg aaacggcaag caagcccggc      60
gagccggtga aactgcgctc cacgtgtgac gcctgccaga aggccaaaca tcggtgctcg     120
cgcgaacagc cgtgccaaca ctgcaagtac aacaaagttc cctgcgtgta cagtgccctg     180
cgacgcattg acgtccgccg cggcggaaaa ccccccggcg acgcggccga gagagagaag     240
acccccaaga ggagcaaaaa ccgtgccttc cagggcaaca cacggcgtc cacacacgcc      300 tccgaaggca gtcccgccga gcctccattg ccccgacga cggcatccat ctccatcagc     360
caccgtgcgg tcgattcctt ctcgtcttcc tcctcatacg atcatgcctt ctgctcggg     420
```

```
cacggcccgg ccgccgccgc caggatggat gacgacgcct ggctggagat ggatggctcg    480
aatcatgacc ccgcggggga ccctcggga ccccccgcat tcgatctgga gtctatcctg    540
gacttcgacg ggccgacgct gagcggaatg accgccggtg cgtccatggc ccccagtgac    600
cagggcccct gtccgcccgg caccgagccc ccatccttcc ttgaatcgtt caaatcggcg    660
gcggctccga tgggggatgc cttcctgttc ctcgagaacc ctccgccctt cgagtcgtcg    720
gcgggccccg gactgcctcc gccggccccg gaggagccag gggtcggcta cccgatgtcc    780
atgccggcgg acagccatcc cgaggggtcg gcgccgaggc cgcagcgtct cccatcggcg    840
ccgccggccc ggcactgcga atgctatcag tcggtgctgg ccagcctggg ggatttcgat    900
cgccgcacct cgctgggact ggcgtgctcg atcgacatgc tcgtggccct ggagcagagc    960
gcccaccggc aggcggcgca ggtcctgcag tgccagggat gttccggcag tcgcccggac    1020
ctcctcctgc tggtggcgct gaagatcgac aacaccgtgg gcatgctgga gagcgtgtcc    1080
aagttcaatc tgacgctcat ccgcccgggc gccgcctcct cgctcctggc tggttcccgg    1140
cggtcgtcgt gtggcgcgtg cgacagcgcc agcgtcagca gcggcggcag cagtcagggg    1200
tctcgggcgt cgaacaacag tctgtcgggg ctcatgaaca ccggcggct gttggcgggc    1260 gcgttcgaga tccaagccga agagaagatc catttcttca agcagttct ctgcaagcgc    1320 ctgcgccggc tctcctcggt cttgcagcag ctgcagcagc gcatgctcca ggcgccgcag    1380
acgtccatct cacagacggg gttcaatctg gtgtcggaga atcgtcgacg cctgcagtcg    1440
gtcatcggcc ggctggagct gtggcaaggg taa                                1473

<210> SEQ ID NO 25
<211> LENGTH: 490
<212> TYPE: PRT
<213> ORGANISM: Paecilomyces divaricatus

<400> SEQUENCE: 25

Met Pro Ser Ser Ser Phe Pro His Pro Pro Ser Gly Glu Thr Ala
1               5                   10                  15

Ser Lys Pro Gly Glu Pro Val Lys Leu Arg Ser Thr Cys Asp Ala Cys
            20                  25                  30

Gln Lys Ala Lys His Arg Cys Ser Arg Glu Gln Pro Cys Gln His Cys
        35                  40                  45

Lys Tyr Asn Lys Val Pro Cys Val Tyr Ser Ala Leu Arg Arg Ile Gly
    50                  55                  60

Arg Pro Pro Arg Lys Pro Pro Gly Asp Ala Ala Glu Arg Glu Lys
65                  70                  75                  80

Thr Pro Lys Arg Ser Lys Asn Arg Ala Phe Gln Gly Asn Asn Thr Ala
                85                  90                  95

Ser Thr His Ala Ser Glu Gly Ser Pro Ala Glu Pro Pro Leu Pro Pro
            100                 105                 110

Thr Thr Ala Ser Ile Ser Ile Ser His Arg Ala Val Asp Ser Phe Ser
        115                 120                 125

Ser Ser Ser Ser Tyr Asp His Ala Phe Leu Leu Gly His Gly Pro Ala
    130                 135                 140

Ala Ala Ala Arg Met Asp Asp Asp Ala Trp Leu Glu Met Asp Gly Ser
145                 150                 155                 160

Asn His Asp Pro Ala Gly Asp Pro Ser Gly Pro Pro Ala Phe Asp Leu
                165                 170                 175

Glu Ser Ile Leu Asp Phe Asp Gly Pro Thr Leu Ser Gly Met Thr Ala
```

```
                    180                 185                 190
Gly Ala Ser Met Ala Pro Ser Asp Gln Gly Pro Cys Pro Pro Gly Thr
                195                 200                 205

Glu Pro Pro Ser Phe Leu Glu Ser Phe Lys Ser Ala Ala Ala Pro Met
            210                 215                 220

Gly Asp Ala Phe Leu Phe Leu Glu Asn Pro Pro Pro Phe Glu Ser Ser
225                 230                 235                 240

Ala Gly Pro Gly Leu Pro Pro Ala Pro Glu Glu Pro Gly Val Gly
                245                 250                 255

Tyr Pro Met Ser Met Pro Ala Asp Ser His Pro Glu Gly Ser Ala Pro
                260                 265                 270

Arg Pro Gln Arg Leu Pro Ser Ala Pro Pro Ala Arg His Cys Glu Cys
            275                 280                 285

Tyr Gln Ser Val Leu Ala Ser Leu Gly Asp Phe Asp Arg Arg Thr Ser
                290                 295                 300

Leu Gly Leu Ala Cys Ser Ile Asp Met Leu Val Ala Leu Glu Gln Ser
305                 310                 315                 320

Ala His Arg Gln Ala Ala Gln Val Leu Gln Cys Gln Gly Cys Ser Gly
                325                 330                 335

Ser Arg Pro Asp Leu Leu Leu Val Ala Leu Lys Ile Asp Asn Thr
                340                 345                 350

Val Gly Met Leu Glu Ser Val Ser Lys Phe Asn Leu Thr Leu Ile Arg
                355                 360                 365

Pro Gly Ala Ala Ser Ser Leu Leu Ala Gly Ser Arg Arg Ser Ser Cys
            370                 375                 380

Gly Ala Cys Asp Ser Ala Ser Val Ser Ser Gly Gly Ser Ser Gln Gly
385                 390                 395                 400

Ser Arg Ala Ser Asn Asn Ser Leu Ser Gly Leu Met Asn Ser Arg Arg
                405                 410                 415

Leu Leu Ala Gly Ala Phe Glu Ile Gln Ala Glu Glu Lys Ile His Phe
                420                 425                 430

Phe Lys Gln Phe Leu Cys Lys Arg Leu Arg Arg Leu Ser Ser Val Leu
            435                 440                 445

Gln Gln Leu Gln Gln Arg Met Leu Gln Ala Pro Gln Thr Ser Ile Ser
            450                 455                 460

Gln Thr Gly Phe Asn Leu Val Ser Glu Asn Arg Arg Arg Leu Gln Ser
465                 470                 475                 480

Val Ile Gly Arg Leu Glu Leu Trp Gln Gly
                485                 490

<210> SEQ ID NO 26
<211> LENGTH: 1131
<212> TYPE: DNA
<213> ORGANISM: Paecilomyces divaricatus

<400> SEQUENCE: 26
atgcatttca atcttctcct cgtcttgacc gtcctcctcc gccaggctac ggcactcgtc     60
ctgccgccgt ccaacagcac ctccaattcg accggcaaat tctccgcccg caccgtcttc    120
cagttccccc agggatactg gctggagaat ctggccgtcc ggggcaatgg ccaggtcctc    180
gcaaccacct acatgccgtc ggccggcctg tatctcatcg accccactcc caatgccagc    240
tatcccgcgg tcctcgtcca ccagttcgag aactcgacct cggccctggg catcgtggag    300
gcggagggga cagagcccga caccttctat ctggcgacgc tgaacttctc cgccgcggac    360
```

-continued

| | |
|---|---|
| ggcttcgtcc cccgcaccag ccaggtctgg cgagtggaca tgtcctcgtt ccactactca | 420 |
| ccccagaccg ggcaggtctc cgggaaggcg gccgtctcgc atgttacgac gctgtcgtcg | 480 |
| gtgggcatgg ccaacggtat gaccctgctg gctccggact cgtcgcacat cctgatcgcg | 540 |
| gactcccttc ggggcgccat ctgggacctg gacaccgcga cgggccacta tggcctctcg | 600 |
| tcgtccttcc ccgccatgcg gtccgacaat ccggcgcgcc gcttcctcgg gatcgacgga | 660 |
| gtcaaggtgc accagggcag cctgtatttc aacaatgcgg gtgaattcac cctcgcccgc | 720 |
| atgcccatcc acagcgatgg catcgccaag ggggagccgg tcgtcctggc cacggacctc | 780 |
| tacagcgatg ggttctgtct gtacgacgcc gacacggtgc tggtgacgat gaacatcgac | 840 |
| aacggcctcg ccgcgctgga cctggagagc atcgccggt ggatggtggc cggcaacatg | 900 |
| cccgacgggg tctttacgac tccaacgtcg gtcgagctgg gccgcgggga ggacgcgggc | 960 |
| aaactcgcct acgtgaccat gggaggcacc tacgtggcga ccggtgccga ggatctcgtc | 1020 |
| gggggcagct tagtcgtggt ggacctgaag tcggccacga ccgatccgaa aggaacggga | 1080 |
| agaggtgggc tgctggtgca ggagacagag acgatttggt tggagctgta g | 1131 |

<210> SEQ ID NO 27
<211> LENGTH: 376
<212> TYPE: PRT
<213> ORGANISM: Paecilomyces divaricatus

<400> SEQUENCE: 27

Met His Phe Asn Leu Leu Val Leu Thr Val Leu Arg Gln Ala
1               5                   10                  15

Thr Ala Leu Val Leu Pro Pro Ser Asn Ser Thr Ser Asn Ser Thr Gly
                20                  25                  30

Lys Phe Ser Ala Arg Thr Val Phe Gln Phe Pro Gln Gly Tyr Trp Leu
            35                  40                  45

Glu Asn Leu Ala Val Arg Gly Asn Gly Gln Val Leu Ala Thr Thr Tyr
        50                  55                  60

Met Pro Ser Ala Gly Leu Tyr Leu Ile Asp Pro Thr Pro Asn Ala Ser
65                  70                  75                  80

Tyr Pro Ala Val Leu Val His Gln Phe Glu Asn Ser Thr Ser Ala Leu
                85                  90                  95

Gly Ile Val Glu Ala Glu Gly Thr Glu Pro Asp Thr Phe Tyr Leu Ala
            100                 105                 110

Thr Leu Asn Phe Ser Ala Ala Asp Gly Phe Val Pro Arg Thr Ser Gln
        115                 120                 125

Val Trp Arg Val Asp Met Ser Ser Phe His Tyr Ser Pro Gln Thr Gly
    130                 135                 140

Gln Val Ser Gly Lys Ala Ala Val Ser His Val Thr Thr Leu Ser Ser
145                 150                 155                 160

Val Gly Met Ala Asn Gly Met Thr Leu Leu Ala Pro Asp Ser Ser His
                165                 170                 175

Ile Leu Ile Ala Asp Ser Leu Arg Gly Ala Ile Trp Asp Leu Asp Thr
            180                 185                 190

Ala Thr Gly His Tyr Gly Leu Ser Ser Ser Phe Pro Ala Met Arg Ser
        195                 200                 205

Asp Asn Pro Ala Arg Arg Phe Leu Gly Ile Asp Gly Val Lys Val His
    210                 215                 220

Gln Gly Ser Leu Tyr Phe Asn Asn Ala Gly Glu Phe Thr Leu Ala Arg
225                 230                 235                 240

```
Met Pro Ile His Ser Asp Gly Ile Ala Lys Gly Glu Pro Val Val Leu
            245                 250                 255

Ala Thr Asp Leu Tyr Ser Asp Gly Phe Cys Leu Tyr Asp Ala Asp Thr
        260                 265                 270

Val Leu Val Thr Met Asn Ile Asp Asn Gly Leu Ala Ala Leu Asp Leu
    275                 280                 285

Glu Ser His Arg Arg Trp Met Val Ala Gly Asn Met Pro Asp Gly Val
290                 295                 300

Phe Thr Thr Pro Thr Ser Val Glu Leu Gly Arg Gly Glu Asp Ala Gly
305                 310                 315                 320

Lys Leu Ala Tyr Val Thr Met Gly Gly Thr Tyr Val Ala Thr Gly Ala
                325                 330                 335

Glu Asp Leu Val Gly Gly Ser Leu Val Val Val Asp Leu Lys Ser Ala
            340                 345                 350

Thr Thr Asp Pro Lys Gly Thr Gly Arg Gly Gly Leu Leu Val Gln Glu
        355                 360                 365

Thr Glu Thr Ile Trp Leu Glu Leu
    370                 375

<210> SEQ ID NO 28
<211> LENGTH: 1598
<212> TYPE: DNA
<213> ORGANISM: Paecilomyces divaricatus

<400> SEQUENCE: 28
atgtcgcatg agctctaca tatccgagac tcccgcacat cgcgggagta tgagatcccc    60
atccggcgca acaccgtcct cgccaccgat ctcaagcaga tcaaggcgtc cccggtgggc   120
gcggatcgag cggacaaagt gggcgatggc ctgcgggtct tgatccgggg tctcaagaac   180
acctgcgtgg tggagaccaa catgacatat acgtagggaa cgggtccaag agagttcccc   240
cccgggggaa ggttctttat ttcactaatg ctcaatttag ggacggacat cgcgggctgt   300 tgcttttcg gggctatgcc ctggagcaac tatggcaggc cgagttcgag acatgctgc    360 atctcttggt ctggggcaaa tatcccacgc cgtctcagcg agaggcgttg cgtctgacct   420
tggccacgct catgtcgacc acgcccaaac atgtcgcgga ggtgattgag acattcccgt   480
aggtcttcta ctgtgctttt catcgtccat cacgatcacc ttgaatgaat gaagaactga   540
accccctgca gtccgacaag ccccccgatg cccatgattg tggccgggct gtccgcgtat   600
ctggcccacc atgccgactc catcccagcc tgtgccgggg caacatctca ccatggaaat   660
cccgaacaga ctgaccgtgc cattctccgg acggcagccg cctacgcggt ggtgatgggc   720
atggcggcca ccaccgtcg cggcatcgcc ttcacgccgg ccacgacgga taacacctac   780
tttgagaacc tgttcatcat gatgggcctg gttgaaccgt acaccggtcg tccagacccg   840
gtgaagctgt cctgcttccg gcggtttgcg gcgctcaact ccgagcacgg catggcgctg   900
tcctcgtttg cgatggtggt aaccgcctcc tcgctgacgg atcccatctc gggcctcatc   960
agctccctgg tggctgcgta cgggcccctg cactttggcg ccccggaggc ggaatacaaa  1020
accatccaag cggtcggcag cgtcgaccag gtgccggctt ttctggagga ggtcaagtct  1080
ggcaagcggc ggctgtttgg gtacggccat cgcacgtaca cgacgatcga ccccggtgtg  1140
aagcccatca agatatgct cttcagcgag ctggacgggg actcggatcc gctggtcaag  1200
gtggcgcggg agatcgatcg cctctcgtcg accgatgagt atttcatcaa acgaaaactg  1260
catgcgaacg cggacttta cggaaccttt ttctttaatc gcctgtaagt tgttttctg   1320
```

-continued

```
ttgattgcag tggatgacaa ttgaccggtc gggtcgtagg ggattccaac cggaggaaat    1380
cccggttgca atggtagcac agcggttggt gggcatcctg gcgcattatc gggagtccat    1440
gtgtaggtcc agccgatttc caactttcaa gcaagggcaa gagagctgat aaaatgcccg    1500
cagtgaaaaa caaatccgc ctcttccggc ccacgcacgt ctacacgggg gagaccgaac     1560
cagtgctcga gatgacggcg ccgtcggcga agctatga                            1598
```

<210> SEQ ID NO 29
<211> LENGTH: 446
<212> TYPE: PRT
<213> ORGANISM: Paecilomyces divaricatus

<400> SEQUENCE: 29

```
Met Ser His Gly Ala Leu His Ile Arg Asp Ser Arg Thr Ser Arg Glu
1               5                   10                  15

Tyr Glu Ile Pro Ile Arg Arg Asn Thr Val Leu Ala Thr Asp Leu Lys
            20                  25                  30

Gln Ile Lys Ala Ser Pro Val Gly Ala Asp Arg Ala Asp Lys Val Gly
        35                  40                  45

Asp Gly Leu Arg Val Phe Asp Pro Gly Leu Lys Asn Thr Cys Val Val
    50                  55                  60

Glu Thr Asn Met Thr Tyr Thr Asp Gly His Arg Gly Leu Leu Leu Phe
65                  70                  75                  80

Arg Gly Tyr Ala Leu Glu Gln Leu Trp Gln Ala Glu Phe Glu Asp Met
                85                  90                  95

Leu His Leu Leu Val Trp Gly Lys Tyr Pro Thr Pro Ser Gln Arg Glu
            100                 105                 110

Ala Leu Arg Leu Thr Leu Ala Thr Leu Met Ser Thr Thr Pro Lys His
        115                 120                 125

Val Ala Glu Val Ile Glu Thr Phe Pro Pro Thr Ser Pro Pro Met Pro
    130                 135                 140

Met Ile Val Ala Gly Leu Ser Ala Tyr Leu Ala His His Ala Asp Ser
145                 150                 155                 160

Ile Pro Ala Cys Ala Gly Gly Asn Ile Tyr His Gly Asn Pro Glu Gln
                165                 170                 175

Thr Asp Arg Ala Ile Leu Arg Thr Ala Ala Ala Tyr Ala Val Val Met
            180                 185                 190

Gly Met Ala Ala Ser His Arg Arg Gly Ile Ala Phe Thr Pro Ala Thr
        195                 200                 205

Thr Asp Asn Thr Tyr Phe Glu Asn Leu Phe Ile Met Met Gly Leu Val
    210                 215                 220

Glu Pro Tyr Thr Gly Arg Pro Asp Pro Val Lys Leu Ser Cys Phe Arg
225                 230                 235                 240

Arg Phe Ala Ala Leu Asn Ser Glu His Gly Met Ala Leu Ser Ser Phe
                245                 250                 255

Ala Met Val Val Thr Ala Ser Ser Leu Thr Asp Pro Ile Ser Gly Leu
            260                 265                 270

Ile Ser Ser Leu Val Ala Ala Tyr Gly Pro Leu His Phe Gly Ala Pro
        275                 280                 285

Glu Ala Glu Tyr Lys Thr Ile Gln Ala Val Gly Ser Val Asp Gln Val
    290                 295                 300

Pro Ala Phe Leu Glu Glu Val Lys Ser Gly Lys Arg Arg Leu Phe Gly
305                 310                 315                 320

Tyr Gly His Arg Thr Tyr Thr Thr Ile Asp Pro Arg Val Lys Pro Ile
```

```
                325                 330                 335
Lys Asp Met Leu Phe Ser Glu Leu Asp Gly Asp Ser Asp Pro Leu Val
                340                 345                 350

Lys Val Ala Arg Glu Ile Asp Arg Leu Ser Ser Thr Asp Glu Tyr Phe
                355                 360                 365

Ile Lys Arg Lys Leu His Ala Asn Ala Asp Phe Tyr Gly Thr Phe Phe
                370                 375                 380

Phe Asn Arg Leu Gly Phe Gln Pro Glu Glu Ile Pro Val Ala Met Val
385                 390                 395                 400

Ala Gln Arg Leu Val Gly Ile Leu Ala His Tyr Arg Glu Ser Met Leu
                405                 410                 415

Lys Asn Lys Ile Arg Leu Phe Arg Pro Thr His Val Tyr Thr Gly Glu
                420                 425                 430

Thr Glu Pro Val Leu Glu Met Thr Ala Pro Ser Ala Lys Leu
                435                 440                 445

<210> SEQ ID NO 30
<211> LENGTH: 1094
<212> TYPE: DNA
<213> ORGANISM: Paecilomyces divaricatus

<400> SEQUENCE: 30
atggcctcca aggaaacttt cagcaaatac cctgccttcc ccgacaacat ccccacggcg     60
gcggtcccca agatctccct ccgccagatt ttgtcccgcg accccaccgt gtcgaagcgt    120
ctggtcgacg cgggcaagga attcggctgc ttcaaggtcg acctgaccga tgccatcgac    180
ggccctgtcc tctgtcaggg cgtcgagcgc ggctttgacc tgggcaaggc cttcttcgac    240
caagacatcg agaccaagaa ggcatacaag ctgagtcacg agaacgtcgg gtaggtttct    300
ccccagccga cgtcggccca gatgatactc acccacgggt gcacaggtac aagcaggcc     360 gcgttctggt cattaccaag gagcggcgag accaggtcga gacatgctcc gtctcgcgcg    420
atgatctggc ggccagccga cccgacctgc cctctgtgtt cgaccagcag cggctgctgc    480
tccagggcct cgttgcgcag ctcgggcagc tctcgcacct ggccgtctac catctgtcgg    540
agggtctggg gctggattat ggagtcgtgt cggcgcgcca tgatcccgc gaccagtccg     600 ccacgatgat ccgtttcctg cataatccgc cgcagagagg accgcgcgag gagctgccct    660
cgaccgagga cccgggttcg cgggcctacc tgatgggcca cagcgacggg ggcacggtga    720
ccatcctgtt caacgtcctg ggtggactgc agctccagcg ccagcagccc gatggctcca    780
tcgagtggca gtacattccg cccgagcccg gctgtgcctt gatcatggtg ggcgacgcct    840
tcaagtcctt cacggacggg gaagtcccct cgtgcgtgca ccgggtcatc cagccgccgg    900
gcgagcagga tcgcttcgat cggtatgcgc tgggcttctt cctcaagccc gccaacgggg    960
cctccattgg accagtgccg cgccggggcg tgacggagaa tggcgtcaac aaggcgtcgg   1020
actatggaga gtgggcaaag aacaagaacg cggcgttgta caacgagatg cgccaggaga   1080
atgtggcaat ttag                                                    1094

<210> SEQ ID NO 31
<211> LENGTH: 345
<212> TYPE: PRT
<213> ORGANISM: Paecilomyces divaricatus

<400> SEQUENCE: 31

Met Ala Ser Lys Glu Thr Phe Ser Lys Tyr Pro Ala Phe Pro Asp Asn
1               5                   10                  15
```

Ile Pro Thr Ala Ala Val Pro Lys Ile Ser Leu Arg Gln Ile Leu Ser
            20                  25                  30

Arg Asp Pro Thr Val Ser Lys Arg Leu Val Asp Ala Gly Lys Glu Phe
        35                  40                  45

Gly Cys Phe Lys Val Asp Leu Thr Asp Ala Ile Asp Gly Pro Val Leu
    50                  55                  60

Cys Gln Gly Val Glu Arg Gly Phe Asp Leu Gly Lys Ala Phe Phe Asp
65                  70                  75                  80

Gln Asp Ile Glu Thr Lys Lys Ala Tyr Lys Leu Ser His Glu Asn Val
                85                  90                  95

Gly Tyr Lys Gln Ala Gly Val Leu Val Ile Thr Lys Glu Arg Arg Asp
            100                 105                 110

Gln Val Glu Thr Cys Ser Val Ser Arg Asp Asp Leu Ala Ala Ser Arg
        115                 120                 125

Pro Asp Leu Pro Ser Val Phe Asp Gln Gln Arg Leu Leu Leu Gln Gly
    130                 135                 140

Leu Val Ala Gln Leu Gly Gln Leu Ser His Leu Ala Val Tyr His Leu
145                 150                 155                 160

Ser Glu Gly Leu Gly Leu Asp Tyr Gly Val Val Ser Ala Arg His Asp
                165                 170                 175

Pro Arg Asp Gln Ser Ala Thr Met Ile Arg Phe Leu His Asn Pro Pro
            180                 185                 190

Gln Arg Gly Pro Arg Glu Glu Leu Pro Ser Thr Glu Asp Pro Gly Ser
        195                 200                 205

Arg Ala Tyr Leu Met Gly His Ser Asp Gly Gly Thr Val Thr Ile Leu
    210                 215                 220

Phe Asn Val Leu Gly Gly Leu Gln Leu Gln Arg Gln Gln Pro Asp Gly
225                 230                 235                 240

Ser Ile Glu Trp Gln Tyr Ile Pro Pro Glu Pro Gly Cys Ala Leu Ile
                245                 250                 255

Met Val Gly Asp Ala Phe Lys Ser Phe Thr Asp Gly Glu Val Pro Ser
            260                 265                 270

Cys Val His Arg Val Ile Gln Pro Pro Gly Glu Gln Asp Arg Phe Asp
        275                 280                 285

Arg Tyr Ala Leu Gly Phe Phe Leu Lys Pro Ala Asn Gly Ala Ser Ile
    290                 295                 300

Gly Pro Val Pro Arg Arg Gly Val Thr Glu Asn Gly Val Asn Lys Ala
305                 310                 315                 320

Ser Asp Tyr Gly Glu Trp Ala Lys Asn Lys Asn Ala Ala Leu Tyr Asn
                325                 330                 335

Glu Met Arg Gln Glu Asn Val Ala Ile
            340                 345

<210> SEQ ID NO 32
<211> LENGTH: 1661
<212> TYPE: DNA
<213> ORGANISM: Paecilomyces divaricatus

<400> SEQUENCE: 32
atgggggatc atttaatatt cttggatcag attgtacagg ctccctcag gctttgccca      60 ggttcaatgc actctgtcat ggcttcatcc accaagatcc ccatccccg ggtcaccgtc     120 gacgaagcca ctgctcttct tgcaccgccg caaccgcctt actcggtgtt ttccccagtg    180
cagaagaagc tcattgtctt cacggcagcc ttggcctcga cctttcgcc tctctcatcc    240

```
aatatctact acccggctat caactccatt gccgatgagt tgaagatcag tcccggaatg   300
gtcaacctaa ccatcacggc ctatatggta agctcgtatg ctttgtcata ctttctcacg   360
gctctcgaga cagttcctga tcaacactac aggttttca agggctaacc cccgcccttta  420 tgggagatct ctcggatacg gccggccgac ggccggtata tgtcctctgc ttcggcatct   480
atatcgtagc caacatcggc ttagctctgc aacgagattt tgtgactctt ctggtgctgc   540
gggccctgca aagtaccggc atcagcgcca ctgtcgcgct atccaacgcc gttgcggccg   600
acaccgtgac gtccgccgag cggggatgt atttgggcat cgcctctctc gggggaatcc    660
tgggacccgc gctggggcca acctaggcg gtctcttgag tcaatccctc ggatggcggt    720
ctatcttctg gtttctggcg ctcgtggctg ccgtcttttt cgtgcttttg atgctgttct   780
tccccgagac ctgccgtgcg atcgtgggca atgggtccat tccacctcct cggtggaatc   840
gctctctgct cgactgtatg gtcggacgga ctcgagggaa gcaacagcta aatctgtcgc   900
cggaagctga taatgctcct cccaagccac accaaaagtc gcggatccgt gtgcccaacc   960
cctggagcac gctgcgtctg ctctttgaaa tgccaacggg gttggtcctt ctgagcaatg  1020
gaatcggata cgcggcctat tacgccgtca cctcgacggt gccgacgcag tggaacgaga  1080
tttaccatct caacgacttc cagctcggac tcacctatat tcccattggg ttgggcacca  1140
tcctgtcggc cttcaccaac ggatggctcg tcgactggaa cttccaacgc atcgcccgcc  1200
aggtcggaca gctgccgatc cgcaacggga agcaggatct ccggcagttt cccattgagc  1260
gcgcacggct gcagattgcc atgccgtcag cgatgctggc ggccgcctcg attgccctct  1320
acggctgggt gatcgcggcc gaacgcccca tcgtggaggc gctggccatg ctccttctga  1380
tcggatatct cgtcacggcg agctacaatg tcatgaacgt gctgattgta gatctccatt  1440
acggaaagcc ggccacagcg accgccgcaa acaacctggt gcgctgctta ctcggggcgg  1500
gagccacggc gggcgtcacg cccctcctgg atcttctggg ccgacaatgg tgtttctgcg  1560
tggtgggtgc catctacgtg atatctctgc ctctgagcgg gcttgtgtat gggtttggcg  1620
caggatggcg agaaaaaaga gatgccgaga gagatgggta g                     1661
```

<210> SEQ ID NO 33
<211> LENGTH: 531
<212> TYPE: PRT
<213> ORGANISM: Paecilomyces divaricatus

<400> SEQUENCE: 33

Met Gly Asp His Leu Ile Phe Leu Asp Gln Ile Val Gln Gly Ser Leu
1               5                   10                  15

Arg Leu Cys Pro Gly Ser Met His Ser Val Met Ala Ser Ser Thr Lys
            20                  25                  30

Ile Pro Ile Pro Arg Val Thr Val Asp Glu Ala Thr Ala Leu Leu Ala
        35                  40                  45

Pro Pro Gln Pro Pro Tyr Ser Val Phe Ser Pro Val Gln Lys Lys Leu
    50                  55                  60

Ile Val Phe Thr Ala Ala Leu Ala Ser Thr Phe Ser Pro Leu Ser Ser
65                  70                  75                  80

Asn Ile Tyr Tyr Pro Ala Ile Asn Ser Ile Ala Asp Glu Leu Lys Ile
                85                  90                  95

Ser Pro Gly Met Val Asn Leu Thr Ile Thr Ala Tyr Met Val Phe Gln
            100                 105                 110

Gly Leu Thr Pro Ala Phe Met Gly Asp Leu Ser Asp Thr Ala Gly Arg

```
            115                 120                 125
Arg Pro Val Tyr Val Leu Cys Phe Gly Ile Tyr Ile Val Ala Asn Ile
130                 135                 140

Gly Leu Ala Leu Gln Arg Asp Phe Val Thr Leu Leu Val Leu Arg Ala
145                 150                 155                 160

Leu Gln Ser Thr Gly Ile Ser Ala Thr Val Ala Leu Ser Asn Ala Val
                    165                 170                 175

Ala Ala Asp Thr Val Thr Ser Ala Glu Arg Gly Met Tyr Leu Gly Ile
                180                 185                 190

Ala Ser Leu Gly Gly Ile Leu Gly Pro Ala Leu Gly Pro Thr Leu Gly
            195                 200                 205

Gly Leu Leu Ser Gln Ser Leu Gly Trp Arg Ser Ile Phe Trp Phe Leu
            210                 215                 220

Ala Leu Val Ala Ala Val Phe Phe Val Leu Leu Met Leu Phe Phe Pro
225                 230                 235                 240

Glu Thr Cys Arg Ala Ile Val Gly Asn Gly Ser Ile Pro Pro Pro Arg
                245                 250                 255

Trp Asn Arg Ser Leu Leu Asp Cys Met Val Gly Arg Thr Arg Gly Lys
                260                 265                 270

Gln Gln Leu Asn Leu Ser Pro Glu Ala Asp Asn Ala Pro Pro Lys Pro
            275                 280                 285

His Gln Lys Ser Arg Ile Arg Val Pro Asn Pro Trp Ser Thr Leu Arg
            290                 295                 300

Leu Leu Phe Glu Met Pro Thr Gly Leu Val Leu Leu Ser Asn Gly Ile
305                 310                 315                 320

Gly Tyr Ala Ala Tyr Tyr Ala Val Thr Ser Thr Val Pro Thr Gln Trp
                325                 330                 335

Asn Glu Ile Tyr His Leu Asn Asp Phe Gln Leu Gly Leu Thr Tyr Ile
                340                 345                 350

Pro Ile Gly Leu Gly Thr Ile Leu Ser Ala Phe Thr Asn Gly Trp Leu
            355                 360                 365

Val Asp Trp Asn Phe Gln Arg Ile Ala Arg Gln Val Gly Gln Leu Pro
370                 375                 380

Ile Arg Asn Gly Lys Gln Asp Leu Arg Gln Phe Pro Ile Glu Arg Ala
385                 390                 395                 400

Arg Leu Gln Ile Ala Met Pro Ser Ala Met Leu Ala Ala Ser Ile
                405                 410                 415

Ala Leu Tyr Gly Trp Val Ile Ala Ala Glu Arg Pro Ile Val Glu Ala
            420                 425                 430

Leu Ala Met Leu Leu Leu Ile Gly Tyr Leu Val Thr Ala Ser Tyr Asn
            435                 440                 445

Val Met Asn Val Leu Ile Val Asp Leu His Tyr Gly Lys Pro Ala Thr
450                 455                 460

Ala Thr Ala Ala Asn Asn Leu Val Arg Cys Leu Leu Gly Ala Gly Ala
465                 470                 475                 480

Thr Ala Gly Val Thr Pro Leu Leu Asp Leu Leu Gly Arg Gln Trp Cys
                485                 490                 495

Phe Cys Val Val Gly Ala Ile Tyr Val Ile Ser Leu Pro Leu Ser Gly
                500                 505                 510

Leu Val Tyr Gly Phe Gly Ala Gly Trp Arg Glu Lys Arg Asp Ala Glu
            515                 520                 525

Arg Asp Gly
    530
```

<210> SEQ ID NO 34
<211> LENGTH: 1087
<212> TYPE: DNA
<213> ORGANISM: Paecilomyces divaricatus

<400> SEQUENCE: 34

```
atggtggcga caaagctttt ctccacggct ctggtggccg ccgccctggt gttaccgggc      60
tctgcgctca gcataatccc cttccagaag cccatggaga tccgcacct gtgtgatggc     120
accggcatcg tggaccccga cggcaactgc aacggggacg gtgtcattga tgagcctccc     180
gcacgtccac cacgcttcgg aaacccaccg ccgcacgagg gcaggacag ggatgggttc     240
aagttcgaga cccctccac ccagtgcaag tacatgtcgc agccggacct ctgggacaac     300
ttcaagtcgc tagagaagga catgagcaag atctttacca tgatccacaa ggacgtcgat     360
tttaccatcg tcggtcacca tcccggtgct gggcactaca ccgacctgct gcacttctac     420
accaatgccc tgcgtcgcta cagcgtctgc ttctcccagt accccgagta tttccgcatc     480
tatccccagg ccatccacgg aggctgcaat agcgagtggt ccgtccagga gattctcttc     540
ctcggccgta ccaaccacgg taagcaaccc tgattgagta tccaaaggga aatagagcta     600
acggtggata ggcgtcgact ttgatgtgat caacgtatgg gtcacccgct ggaaggacgg     660
ccagatggtc gaggtccgca cctacatcga ctccatgcgc atgactggct tgctccatga     720
gaacgagctc tggtggaact ccagcaccta cgaggagcat cccaactaca tcccgggccc     780
aacgggtttg ccagacctcg acgagctgcg cggtctgatg cgcaagccgg atggaagcag     840
gtacgacgac atgtagagag tgtcacggag taaggtcgtg atggatcaac gctgctaaat     900
gatggacgat gtgcaagaat tggaaacgaa atattgtaga tggatttcgc tcgttgctgt     960
tgttgctgat tgccatgttt tgttcgttga tatagttgag taaccagact gagatggatg    1020
agttggggta tatgttggtg tacataggtc aaccgacctc cctcatttaa tatggccctt    1080
gcactag                                                               1087
```

<210> SEQ ID NO 35
<211> LENGTH: 275
<212> TYPE: PRT
<213> ORGANISM: Paecilomyces divaricatus

<400> SEQUENCE: 35

Met Val Ala Thr Lys Leu Phe Ser Thr Ala Leu Val Ala Ala Leu
1               5                   10                  15

Val Leu Pro Gly Ser Ala Leu Ser Ile Ile Pro Phe Gln Lys Pro Met
                20                  25                  30

Glu Asn Pro His Leu Cys Asp Gly Thr Gly Ile Val Asp Pro Asp Gly
            35                  40                  45

Asn Cys Asn Gly Asp Gly Val Ile Asp Glu Pro Pro Ala Arg Pro Pro
        50                  55                  60

Arg Phe Gly Asn Pro Pro His Glu Gly Arg Asp Arg Asp Gly Phe
65                  70                  75                  80

Lys Phe Glu Asn Pro Ser Thr Gln Cys Lys Tyr Met Ser Gln Pro Asp
                85                  90                  95

Leu Trp Asp Asn Phe Lys Ser Leu Glu Lys Asp Met Ser Lys Ile Phe
            100                 105                 110

Thr Met Ile His Lys Asp Val Asp Phe Thr Ile Val Gly His His Pro
        115                 120                 125

Gly Ala Gly His Tyr Thr Asp Leu Leu His Phe Tyr Thr Asn Ala Leu
130                 135                 140
Arg Arg Tyr Ser Val Cys Phe Ser Gln Tyr Pro Glu Tyr Phe Arg Ile
145                 150                 155                 160
Tyr Pro Gln Ala Ile His Gly Gly Cys Asn Ser Glu Trp Ser Val Gln
            165                 170                 175
Glu Ile Leu Phe Leu Gly Arg Thr Asn His Gly Val Asp Phe Asp Val
            180                 185                 190
Ile Asn Val Trp Val Thr Arg Trp Lys Asp Gly Gln Met Val Glu Val
            195                 200                 205
Arg Thr Tyr Ile Asp Ser Met Arg Met Thr Gly Leu Leu His Glu Asn
210                 215                 220
Glu Leu Trp Trp Asn Ser Ser Thr Tyr Glu Glu His Pro Asn Tyr Ile
225                 230                 235                 240
Pro Gly Pro Thr Gly Leu Pro Asp Leu Asp Glu Leu Arg Gly Leu Met
                245                 250                 255
Arg Lys Pro Asp Gly Ser Arg Ser Thr Asp Leu Pro His Leu Ile Trp
            260                 265                 270
Pro Leu His
        275

<210> SEQ ID NO 36
<211> LENGTH: 1530
<212> TYPE: DNA
<213> ORGANISM: Paecilomyces divaricatus

<400> SEQUENCE: 36

```
atgcaagcgt acgaccaggt cattgtggat atcaaagact atgtcttcca ctatgatatc      60
cactccccgc aggcatggac caccgcccgc gtggctcttc tggatgccat gggctgtgcc     120
atcgagactg tcgctctgag tgccgattgt aggcgattct ttggccccat cgttcccgac     180
acggtgactc cctatggctt ccacatgccc gggacctcct atgtcttgga ccccttgaaa     240
ggctcgttcg acatggccac ggcggtgcga tatctggacc ataatgatgc catcgcgggg     300
gcagactggg gacatccgtc gggtatactc tttccatttc ttcttttcga acaaagaag      360
ccgaggacag tcgctgacat ggtccgggca gataatctcg gggcgatcct ggccgtcagt     420
gactggctgt gtcgatccgt cgccagctgc cgcatcgtgc acactgggcc cccattgacg     480
atgcgtacat tgctgacggc gctgatcaag gcctatgaaa tccaggggtg catgctgctc     540
cagaatgcct ttcattcaca cggtctggac catgtcgtgc tggtcaagct ggcctcgacg     600
gccgtcgtgg catggctcct tggcctgtcc gagacgcaga cgatggcggc tatctcgcag     660
gtctggatgg acggtcatcc cctgcgcgtc tatcgctctg gcagtaatac catcccgcgc     720
aagggctggg ccgccggtga tgcctgtatg aaggccacgc atctggcctt gctgactcgc     780
gcgggacaac cgggctcccc gacccccgttg acgatgcccc ggtggggatt ctatgccacc     840
tcgttcggaa ataagacctt cgacctgccg cagccatacg gcagttgggt gatggagaac     900
atcattttca aggtcatgcc cgtcgagggc cacgcactgt cgtcggtcga gcggcgctc       960
cgtcatcggg cagcgatgca ggcgcgaggc atgaagcatc ccgagaagga tattgactgt    1020
atcgagatca ggaccaatgc cgcggccgac atgatcatca caaacgggg ccccgctgtcc    1080
aacgccgcgg accgggatca ttgtctgcag tacatcgtga gcctggcgtt cctcaagggg    1140
gcgatgcccg aagtccgtga ctaccaggat gacagtgtct ggtcgtcaag ccgagccatc    1200
actgcactgc gcgagaagat ccagattcaa ccagatgagc aactgacgcg cgattatctg    1260
```

```
gatctcgacg tgaagagtct ggcgtcggga atgacggtgc gcctgatcga tggcacggtg   1320
ctcgacgaga ttctggtcca cttcccagtc gggcacagca agcatccgca gacgttcacg   1380
acggtccgtg aaaaggtccg gaggaatctg agtctgatgt tttccacgga agaaatctcg   1440
cggatggagg cggcggtgga ggaggagtct ctggggattt ctgggtttgt ggatctcttt   1500
gtccgtcccc ggtctgaagt gaagctttaa                                   1530

<210> SEQ ID NO 37
<211> LENGTH: 509
<212> TYPE: PRT
<213> ORGANISM: Paecilomyces divaricatus

<400> SEQUENCE: 37

Met Gln Ala Tyr Asp Gln Val Ile Val Asp Ile Lys Asp Tyr Val Phe
1               5                   10                  15

His Tyr Asp Ile His Ser Pro Gln Ala Trp Thr Thr Ala Arg Val Ala
            20                  25                  30

Leu Leu Asp Ala Met Gly Cys Ala Ile Glu Thr Val Ala Leu Ser Ala
        35                  40                  45

Asp Cys Arg Arg Phe Phe Gly Pro Ile Val Pro Asp Thr Val Thr Pro
    50                  55                  60

Tyr Gly Phe His Met Pro Gly Thr Ser Tyr Val Leu Asp Pro Leu Lys
65                  70                  75                  80

Gly Ser Phe Asp Met Ala Thr Ala Val Arg Tyr Leu Asp His Asn Asp
                85                  90                  95

Ala Ile Ala Gly Ala Asp Trp Gly His Pro Ser Gly Ile Leu Phe Pro
            100                 105                 110

Phe Leu Leu Phe Glu Thr Lys Lys Pro Arg Thr Val Ala Asp Met Val
        115                 120                 125

Arg Ala Asp Asn Leu Gly Ala Ile Leu Ala Val Ser Asp Trp Leu Cys
    130                 135                 140

Arg Ser Val Ala Ser Cys Arg Ile Val His Thr Gly Pro Pro Leu Thr
145                 150                 155                 160

Met Arg Thr Leu Leu Thr Ala Leu Ile Lys Ala Tyr Glu Ile Gln Gly
                165                 170                 175

Cys Met Leu Leu Gln Asn Ala Phe His Ser His Gly Leu Asp His Val
            180                 185                 190

Val Leu Val Lys Leu Ala Ser Thr Ala Val Val Ala Trp Leu Leu Gly
        195                 200                 205

Leu Ser Glu Thr Gln Thr Met Ala Ala Ile Ser Gln Val Trp Met Asp
    210                 215                 220

Gly His Pro Leu Arg Val Tyr Arg Ser Gly Ser Asn Thr Ile Pro Arg
225                 230                 235                 240

Lys Gly Trp Ala Ala Gly Asp Ala Cys Met Lys Ala Thr His Leu Ala
                245                 250                 255

Leu Leu Thr Arg Ala Gly Gln Pro Gly Ser Pro Thr Pro Leu Thr Met
            260                 265                 270

Pro Arg Trp Gly Phe Tyr Ala Thr Ser Phe Gly Asn Lys Thr Phe Asp
        275                 280                 285

Leu Pro Gln Pro Tyr Gly Ser Trp Val Met Glu Asn Ile Ile Phe Lys
    290                 295                 300

Val Met Pro Val Glu Gly His Ala Leu Ser Ser Val Glu Ala Ala Leu
305                 310                 315                 320
```

```
Arg His Arg Ala Ala Met Gln Ala Arg Gly Met Lys His Pro Glu Lys
            325                 330                 335

Asp Ile Asp Cys Ile Glu Ile Arg Thr Asn Ala Ala Asp Met Ile
        340                 345                 350

Ile Asn Lys Arg Gly Pro Leu Ser Asn Ala Ala Asp Arg Asp His Cys
            355                 360                 365

Leu Gln Tyr Ile Val Ser Leu Ala Phe Leu Lys Gly Ala Met Pro Glu
    370                 375                 380

Val Arg Asp Tyr Gln Asp Ser Val Trp Ser Ser Arg Ala Ile
385                 390                 395                 400

Thr Ala Leu Arg Glu Lys Ile Gln Ile Gln Pro Asp Glu Gln Leu Thr
                405                 410                 415

Arg Asp Tyr Leu Asp Leu Asp Val Lys Ser Leu Ala Ser Gly Met Thr
            420                 425                 430

Val Arg Leu Ile Asp Gly Thr Val Leu Asp Glu Ile Leu Val His Phe
        435                 440                 445

Pro Val Gly His Ser Lys His Pro Gln Thr Phe Thr Thr Val Arg Glu
            450                 455                 460

Lys Val Arg Arg Asn Leu Ser Leu Met Phe Ser Thr Glu Glu Ile Ser
465                 470                 475                 480

Arg Met Glu Ala Ala Val Glu Glu Ser Leu Gly Ile Ser Gly Phe
                485                 490                 495

Val Asp Leu Phe Val Arg Pro Arg Ser Glu Val Lys Leu
            500                 505

<210> SEQ ID NO 38
<211> LENGTH: 814
<212> TYPE: DNA
<213> ORGANISM: Paecilomyces divaricatus

<400> SEQUENCE: 38
atgccggtga gatttctttg tctgcatggc tggggcacca atatccaggt tcgtgcgatg      60
accgaaagta atccaatggc tcgcgcctcg agtgactgac cataatttat ctggcagatc     120
ttacagtccc aactcggtag acaccgcagc cctacaaaag aaaaaacaaa aaaaaacccc     180
ctaaccgtga acaggccccc taatgcgaga gctgcagaaa gacaacagcg cggaatttca     240
tttcatccag gcgatgtcg aggcagatcc cggcccaggt atcgagggct tctacgaagg      300
gccctactac agcttctacc aattcccccg gactttcccc gacagtgatg acgaggagga     360
cgatggcgga gatgcgtcca tgttcgaggc tatgagatg atctacgaca tcatagccga     420
ggagggtcct tttgacggca tcctcggctt ctctcacggc ggcaccttgg cctcgggctt     480
cctcatccat cacagtaaga cctccccctta tacgccgccc ccttccgat gcgccgtgtt     540 tttcaattca ctgccgccgt tccgcatgga tcccggcgag gagcttgtcg tggatgatga     600
tctggcccgg cacctcacga taccgaccct cagcattgcg gggacgcggg actttgtcta     660
caagcagtct ctgatgctgc accagttgtg cgatgagaag tcgtcgcagc tgatcctgca     720
tggaaagggc cacgagatcc gggggatgc ggcgacggtg gcgcggatgg ctaaggcatt     780
tcgggcactg tgtttgcggg ccatgtattt gtag                                 814

<210> SEQ ID NO 39
<211> LENGTH: 200
<212> TYPE: PRT
<213> ORGANISM: Paecilomyces divaricatus

<400> SEQUENCE: 39
```

```
Met Pro Lys Asp Asn Ser Ala Glu Phe His Phe Ile Gln Gly Asp Val
1               5                   10                  15

Glu Ala Asp Pro Gly Pro Gly Ile Glu Gly Phe Tyr Glu Gly Pro Tyr
            20                  25                  30

Tyr Ser Phe Tyr Gln Phe Pro Arg Thr Phe Pro Asp Ser Asp Asp Glu
        35                  40                  45

Glu Asp Asp Gly Gly Asp Ala Ser Met Phe Glu Ala Tyr Glu Met Ile
    50                  55                  60

Tyr Asp Ile Ile Ala Glu Gly Pro Phe Asp Gly Ile Leu Gly Phe
65                  70                  75                  80

Ser His Gly Gly Thr Leu Ala Ser Gly Phe Leu Ile His His Ser Lys
                85                  90                  95

Thr Ser Pro Tyr Thr Pro Pro Phe Arg Cys Ala Val Phe Phe Asn
                100                 105                 110

Ser Leu Pro Pro Phe Arg Met Asp Pro Gly Glu Glu Leu Val Val Asp
            115                 120                 125

Asp Asp Leu Ala Arg His Leu Thr Ile Pro Thr Leu Ser Ile Ala Gly
    130                 135                 140

Thr Arg Asp Phe Val Tyr Lys Gln Ser Leu Met Leu His Gln Leu Cys
145                 150                 155                 160

Asp Glu Lys Ser Ser Gln Leu Ile Leu His Gly Lys Gly His Glu Ile
                165                 170                 175

Pro Gly Asp Ala Ala Thr Val Ala Arg Met Ala Lys Ala Phe Arg Ala
            180                 185                 190

Leu Cys Leu Arg Ala Met Tyr Leu
            195                 200

<210> SEQ ID NO 40
<211> LENGTH: 7783
<212> TYPE: DNA
<213> ORGANISM: Paecilomyces divaricatus

<400> SEQUENCE: 40
atggttgaga atgtctcctc tccttcgtcg ccacggactt cgagtccgag tggctcctgt        60
acgcccacca gcgccaccag cgtgggatcc gacgacaaga gtatgcccat tgctgtcgtc       120
gggatgagct tcggggcccc agggatgcca tcagcgtgg agagtctctg gaggatgatc        180
tccgagggcc gcgagggatg gagtaaaatc cccaagtcac gatggaataa tgacgccttc       240
taccatccgg atcatagtcg gcatggaacg gtgagggctt cctttctctt gaaagctgaa       300
cgcgaagcga gatcaaatgg aaagttaaat tcctaataaa aattacgagt ggctaatgga       360
aacgcttaga tcaatgttga aggagggcat ttcttggaag aagatctcgc tcgcttcgat       420 gctcccttt tcaatatgac caacgcagaa gcagccgtga gtattaagag atttctgaca        480
tgcaactatc gtggctgaaa cccgtcaggc actggatccc caacaacgac tgctactcga       540
aagcaccttc gaggctgtcg aaaatggtga gttgttggtc tttgtttccc agaccaaaat       600
gaatccctga cgatcgtagc gggaatacec ctggacaaga tgcttgggtc caagacctcc       660
tgcttcgtgg gctccttctg cggcgactac accgacatgc ttgtgcgaga ccccgaggcc       720
atccccatgt accaatgcac caacgccggt cagtcgcggg ccatcacggc caaccgggtc       780
tcctacttct tcgatctgcg tgggcccagc gtcaccgttg atacggcttg ctccggggagt       840 ctagttgccc tccacctggc ctgtcagagc ttacgaacgg gggatgcgaa aatggccatt       900
gtctccgggg tcaataccat tctgagccat gagtttatga gcactatgag catgatgcgg       960
```

-continued

```
taagagtcgt accccctatcg ttttgcggat ccagtctctc acaatgtcag gttcctgtcc    1020
cccgatggac gatgttacac gtttgatgag cgggccaatg gctacgcccg aggcgaagga    1080
gtcggctgtc tacttctgaa accctgtcg gatgccctac gggacaatga tacgatccgc    1140
gccgtcattc gagggacggg ctccaaccag gacggtaaaa cgtcgggcat caccttacca    1200
aacgccaatg cccagcagga attgatccgc gacgtctacg cggctgcggg gctggatcct    1260
ctggaaaccg agtatgtcga gtgccacggt accggcactc aggccggcga tcctctcgag    1320
accggcgccg tggccaaggt ctttctcct ggccggccgg acgatcggcc gctgcgcatc    1380
ggctctatca agacgaatgt cggccacttg aaggggcga gcggcattgc aggcgtgatc    1440
aaagcggtcc tgacgctgga gaaccaatgt ttcctcccaa atcgaaactt caagagcatt    1500
aacccgcgca ttccgctcaa ggagtggaaa ttgaaggtgc gtgagttgtc gtcgtctgct    1560
accatcgtcg tctgctacca acaagaaact gacatcgtca gatccaactg gagaatgaac    1620
gatgggaaac agtaggcccc catcgggtct ccgtcaacag tttcgggtac gggggaagca    1680
atgcacacgc cgttcttgaa gacaccaagg gttaccttga acagagatcc ctaacaggct    1740
ccttccgccg cgtacgagcg cttccccatg ccgccactga cctcgagcca gtctcggacc    1800
cgggttctgg cccagagcgt acccgacttt ttgtcctgtc cagttttgat caggcgtctg    1860
gtcagcaaca gatcgaccaa ctgcgggaat acttggagca gaactcctct cgaatagatg    1920
atcaatacct ggcagatctc gcttacactc tcggcgagcg ccgctcgccc tttctctgga    1980
agacggcgat gccggcatcg tccgtgtcca gtctcgtcga agggttgaag actcgcgcca    2040
aggtctctcg ggccgagaag aagaagccga cgctgggctt catcttcacg ggtcaaggcg    2100
ctcaatggtg cggcatgggt cgcgagcttc tggcagcgta tcccgtcttt gcttcgagcg    2160
tggacgctat cgccacctat ctgaaaagcc ttggggctcc cttcgacgtc cgggaggagc    2220
tcgtccggga tcccaaggac tccaagatca atcaaccgtt gtacagccag ccgatatgca    2280
ccgccgtcca gattgccctg gtagatctgc tcaccttctg gggaatccgg cctgcctctg    2340
tgaccggcca ctccagcggc gagcttgcgg gggcatacac ggcagggcc ctgagcatgg    2400 aacacagtat ggccgctgcg tattatcgag gcgttgcgtc cagtgatctt ccccgagacc    2460
acacgcaacg aggcgccatg atggcggtgg gagccagtaa agacgccatc cagccccgat    2520
tgtcctcgct gacgacgggc accgccgtgg tcgcgtgcgt caacagcccc tccagcgtca    2580
ccatctcggg cgatgcatcc gctgtggacg agctgcatgg tttgctcgag aaggaccagg    2640
tgttcgcgcg gaagttggcc gtcgacgtcg cctatcactc gcaccatatg aaagccgtgg    2700
ccgaccaata tcgcaccgcc atggccgccg ccggcgtcac cgcggttcag cctgagtcca    2760
cggagcccga agtggaattc ttctcgtccg tgacgggcga gaaagccagc ctcaccgacc    2820
tgggaatcga atactgggtc gccaacctgc tcagccaggt caagtttgcc gattccgtgc    2880
atcgcctgtg catggagacg tcggcttccg gacgggctcg caagaccaaa accaaggcac    2940
cgaaacgctc aggggccaac aacaaggcca aggtcgacat gctcgtcgag attggcccgc    3000
attcaacgct ggcagggcca attcgccaga tcctcggggc cgaccagacg ctggagcagg    3060
cgtcgatccg ctatgccagt gccctgctgc gcaagtcgag tgcggtcgat accacgctga    3120
ccctggcgtc gaccttactg atggccgggt atccgatcga catggctgcc atcaatcgac    3180
cgtcggatca ccaccgagtg ggcgtcctcg tcgatctccc tccctatccg tggaaccact    3240
cgggatcata ctgggcagag ccgcgcggttga gcaaagccta tcgcaaccgc gctcatcccc    3300
```

```
ggaacgacct tctgggagtg ttggatacgc attccagccc gcgggagccc cggtggcgca    3360
attatctccg gacgagcgag atcccttgga tcaaagacca tatgatccag tcgaacgtgg    3420
tgtatccggc ggccggctac ctcaccatgg cggtcgaagc catcgggcaa cggattgggg    3480
acaacttccc gggccaccgc atctcgggat accgactacg agatgtcgcg atcgaggcgg    3540
ctttggtgat tagcgacgac tcggagccgg aggtcatgct ctccttgcgt ccgtctggcg    3600
acagtggcct ggttccggcc gaacggtggc atgaattcca cgtcctttca gtgaccccg     3660
acaaccggtg gacggagcat tgtcgcgggc tcatctgcgc cgaggtcgcg gccatggacg    3720
gggacgaaga tgaccgtggc gcagaggcag ggttgaccgc cgagacagag cgctggatcg    3780
aggaagcgga gcagctctgc cagaaagacg tcgatatccc ccggttctac gcagagttga    3840
ccggtctggg tctggaatac ggggagacct tgccaacat gacgcgagca cgttcggcct      3900
cccatgtctg cctcgcggag atcgaagtcg cggacactgc ggctgtcatg cctctgggat    3960
tccagtctcc gttcgtggtc catccctcca ccctggacag tctcttccat cctctcttcg    4020
tcgctctgtc ctccgacgag tcactgcaag atcctgccgt gccggtggcc atcgaggaga    4080
tatggatccg ccacggcatg gccaaggagg ccggacacaa gttccaggtc tgcgcgtcga    4140
cccaggagac gggtcgagac cgcattcagg cagctatctc ggtggttgat gctcagaggg    4200
ctcgcagcgg accggcgttg acggtccgcg gcctgacgtg ccagttcctg gaccgcgcat    4260
cgggagatgt cgagggcgac gagcagccta cacggcttgc atacgagctt cactgggagg    4320
cagatgtaga cctgctgtcg tcgagcgacc tggccacgct gtgtgcggtt ggccgtcccc    4380
gtgatgtagg ggagaaggtc gctcgatatg tgaagcttct cggacacaag aaccctcatc    4440
ttgccatcct ggaggtcgga gccggtcagg gagagctgtg tattccggtg tttcgagccc    4500
tggcagggga ggccaacagc acgccctcgt tccagtcata tacactcgcc gacaccgagc    4560
cgggactgtc ggagaccatt gccacaattg ccgaccagtt tgacgaacgc gccgatctga    4620
ttcaatataa ggagctcgac atctcgtcgg accgctgca gcagggcttc aacgctcact      4680
ctttggacct catccttctt ccttcccggg gagtgtcggc cacgctccga tcgaagatcc    4740
tcaaacatgc gcaccaattg ctcacgcccg aagggagact gattgtggtc gacacgaggg    4800
acctgcagga atggtggcaa gctcttcgtg agagcaactt tactgatccg gaagtgattc    4860
acgacagtcc gagcgagacg gaggccgaca tctcggtgct ggtgtcgaaa ccacaaccac    4920
aacctcggga tcagacccca tcagaccctc cggatgtcct ggttatcgcc gagaaccaag    4980
actccggcgt gtccattgag catctccagc gtctgctggc ggacgctcat gtgccggcga    5040
ccgtcacgga tttcgctcat gcagacccgg agggcaagac gtgcattgtt ctcagcgagt    5100
tgacgacctc tctgctgagc catcccgacc agcattcgtt tgaaacgctc aaaaggatcc    5160
tcgtcgccgg gggtcgcggc gttctctggg tcgttcgggg agcaaccggc ccagcgccca    5220
ccagcagtct ggccaccggt ctgctgcgca cgattcgctc cgagaccgac gatgatcgac    5280
cgattgtgag cctggatctg gatgcctccc atccctgtc ggcggaatcc gcagcgcaat      5340
cgatcttctc cgcgttccgc caccgattcg tctccccgg agggagtcac gaggtcgaat      5400
acgccgaacg cgatgggatc ctgcgcatcc ctcgcgtcgt cgagagttcc ctcgtcaacc    5460
acgagattgt ctcgtccttg cggccggcgg tggccgagga ccagccattc ttccagcccg    5520
gacgtccgct ggaactcacc gtcggcaccc cgggacgtct cgacagtctc tactatgtcg    5580
accgctcctg catctcggag ctacccagtg actacgtcga gatcgaagtc aaagccatcg    5640
ggctcgggaa cggcgatgtc aagaccgctc tgggacatga cgatgccgca accgtctcg     5700
```

```
gagcggaatg cagcggtgtg gtgactgctc tcggggacgc cgtttcgggc ttcaagatcg    5760
gagaccgtgt cgctggcttt ggcgcaggaa ccgtcgccac tttataccga gaccaggcgg    5820
cgcggttcca gctcatcccc gacgacatga gctttgcgcg tgcggccgct ctccccgtgg    5880
catatatcac tgctttcttc gcggtccacg cgctgggcca ggtgagccga ggggaccgag    5940
tcctcatcca ggacgccggc acggccgcgg gccaggctct cctggagctc tgtgccctcg    6000
ccggggggga tatcatcgcc gtggtggatt cgccctcgca aagagccttc ctcgttggcg    6060
agtacgacct cccggcgagc agaatcctgg tcggtctccg cggacgacgt ctagcaacca    6120
gcgtcatgac gctgactagg ggctgcggag tcgatgccat cttcaatttc gcggaggcg    6180 aggagagacg cctgtgctgg agctgcgtgg caccatatgg ccggttcatt gacctgggcg    6240
gcggaccgtc cgacctgacg gatatgccgc agctcgagat ggccagcttc ttttccaaga    6300
atgcttcctt cacggctctg gacttccact acctggtcac gcaaaagcca caggcggtgc    6360
accggatctg gtccgacgtg atgggccctgg tgcgagcaaa ggccatccgg ggcccgccca    6420
ggcttcaact tcattccgtc tccgaggtcg agaccgcgtt gaaacagagt caggacggat    6480
gtgatgtcga gaaagtggtg atccgtgccg aacgggatac aatcgtccag gtctgttgcc    6540
actctgcccc ttatgatatc ctccctcgtg ctaatatgtt ctcttgcagg ccattcctcc    6600
tccgaagggc gacctgctga gggccgacgc gtcatatgtg ctagtcggcg gcctcggagg    6660
cattggacga gcgatggcat cgtggatgat tgccaacgga gcccgacact taatctttgt    6720
caaccgcagt ggcctcgccc gcaacgaagc ccgggagacg gtcgagtctc tcgagggtca    6780
cggtgcccac gtggcggtct attcttgcga tgtcagcgat cgcgaccaag tcgctcagat    6840
ggttgctcag agctccaaag agatgccgcc cattcgaggc gtgattcagg cggccatgat    6900
tctccgggta tgtctgcctt ctcgaaatta gtaggtcgag gactgactgt agtaggatat    6960
gctgtttgag aaaatgagcg tcgacgactt caacaccgtc ctacagccca aatggcaggg    7020
cacatggaat cttcatggcc tcctaccccg agacatggac ttctttatca tgctgtcctc    7080
catcagcggg gtcatcggca acgccactca ggctgcctat gccgctggat cgacgttctt    7140
gggcgcgttc gcccagtatc gcagctccct gggactaccg gccgtgacgc tggatctcgg    7200
cgttatcact ggaatcgggt acctgtccga gcacgaggag ctgctccagg gcatgcagcg    7260
acaaggcttt gaaggcacca acgagcagac gctgatggcc ctcatccgat cagccattgt    7320
cagccctcgt cggacggggt cacaagccga gatcgtcacc gggctgggga cctggcgaga    7380
gggcgtctcg ctgggcaact tcgaccagcc cttgttcgcg cacttccgcc gtcaagccct    7440
gggactccga gatgccacgg cagagggccc gggcaccagc gtccgggaga gtctccgggg    7500
atgcaagacc ctcgacgatg cggtggctct ggtctgtgcg gctctgatcg accgcctggc    7560
ctcgagattg aacaccccgg tggacaatat cgactcccag cgggcgatgt cggagtacgg    7620
ggtggactcg ctggtggcgg tggagatgcg caactggatc ggcaaggaga tggagagcac    7680
gatgcccatt ctggagctgc tggcgaatca atccatctcg cagttgtcgg agaagatagc    7740
tcagcggtca aggtggtgg cagtgagtgg aagtgaagag tag                       7783
```

<210> SEQ ID NO 41
<211> LENGTH: 2451
<212> TYPE: PRT
<213> ORGANISM: Paecilomyces divaricatus

<400> SEQUENCE: 41

-continued

```
Met Val Glu Asn Val Ser Ser Pro Ser Ser Pro Arg Thr Ser Ser Pro
1               5                   10                  15

Ser Gly Ser Cys Thr Pro Thr Ser Ala Thr Ser Val Gly Ser Asp Asp
                20                  25                  30

Lys Ser Met Pro Ile Ala Val Val Gly Met Ser Phe Arg Gly Pro Arg
            35                  40                  45

Asp Ala Ile Ser Val Glu Ser Leu Trp Arg Met Ile Ser Glu Gly Arg
        50                  55                  60

Glu Gly Trp Ser Lys Ile Pro Lys Ser Arg Trp Asn Asn Asp Ala Phe
65                  70                  75                  80

Tyr His Pro Asp His Ser Arg His Gly Thr Ile Asn Val Glu Gly Gly
                85                  90                  95

His Phe Leu Glu Glu Asp Leu Ala Arg Phe Asp Ala Pro Phe Phe Asn
            100                 105                 110

Met Thr Asn Ala Glu Ala Ala Leu Asp Pro Gln Gln Arg Leu Leu
        115                 120                 125

Leu Glu Ser Thr Phe Glu Ala Val Glu Asn Ala Gly Ile Pro Leu Asp
        130                 135                 140

Lys Met Leu Gly Ser Lys Thr Ser Cys Phe Val Gly Ser Phe Cys Gly
145                 150                 155                 160

Asp Tyr Thr Asp Met Leu Val Arg Asp Pro Glu Ala Ile Pro Met Tyr
                165                 170                 175

Gln Cys Thr Asn Ala Gly Gln Ser Arg Ala Ile Thr Ala Asn Arg Val
            180                 185                 190

Ser Tyr Phe Phe Asp Leu Arg Gly Pro Ser Val Thr Val Asp Thr Ala
        195                 200                 205

Cys Ser Gly Ser Leu Val Ala Leu His Leu Ala Cys Gln Ser Leu Arg
    210                 215                 220

Thr Gly Asp Ala Lys Met Ala Ile Val Ser Gly Val Asn Thr Ile Leu
225                 230                 235                 240

Ser His Glu Phe Met Ser Thr Met Ser Met Met Arg Phe Leu Ser Pro
                245                 250                 255

Asp Gly Arg Cys Tyr Thr Phe Asp Glu Arg Ala Asn Gly Tyr Ala Arg
            260                 265                 270

Gly Glu Gly Val Gly Cys Leu Leu Leu Lys Pro Leu Ser Asp Ala Leu
        275                 280                 285

Arg Asp Asn Asp Thr Ile Arg Ala Val Ile Arg Gly Thr Gly Ser Asn
    290                 295                 300

Gln Asp Gly Lys Thr Ser Gly Ile Thr Leu Pro Asn Ala Asn Ala Gln
305                 310                 315                 320

Gln Glu Leu Ile Arg Asp Val Tyr Ala Ala Ala Gly Leu Asp Pro Leu
                325                 330                 335

Glu Thr Glu Tyr Val Glu Cys His Gly Thr Gly Thr Gln Ala Gly Asp
            340                 345                 350

Pro Leu Glu Thr Gly Ala Val Ala Lys Val Phe Ser Pro Gly Arg Pro
        355                 360                 365

Asp Asp Arg Pro Leu Arg Ile Gly Ser Ile Lys Thr Asn Val Gly His
    370                 375                 380

Leu Glu Gly Ala Ser Gly Ile Ala Gly Val Ile Lys Ala Val Leu Thr
385                 390                 395                 400

Leu Glu Asn Gln Cys Phe Leu Pro Asn Arg Asn Phe Lys Ser Ile Asn
                405                 410                 415

Pro Arg Ile Pro Leu Lys Glu Trp Lys Leu Lys Ile Gln Leu Glu Asn
```

```
            420                 425                 430
Glu Arg Trp Glu Thr Val Gly Pro His Arg Val Ser Val Asn Ser Phe
            435                 440                 445
Gly Tyr Gly Gly Ser Asn Ala His Ala Val Leu Glu Asp Thr Lys Gly
            450                 455                 460
Tyr Leu Glu Gln Arg Ser Leu Thr Gly Ser Phe Arg Arg Val Arg Ala
465                 470                 475                 480
Leu Pro His Ala Ala Thr Asp Leu Glu Pro Val Ser Asp Pro Gly Ser
                485                 490                 495
Gly Pro Glu Arg Thr Arg Leu Phe Val Leu Ser Ser Phe Asp Gln Ala
            500                 505                 510
Ser Gly Gln Gln Gln Ile Asp Gln Leu Arg Glu Tyr Leu Glu Gln Asn
            515                 520                 525
Ser Ser Arg Ile Asp Asp Gln Tyr Leu Ala Asp Leu Ala Tyr Thr Leu
            530                 535                 540
Gly Glu Arg Arg Ser Pro Phe Leu Trp Lys Thr Ala Met Pro Ala Ser
545                 550                 555                 560
Ser Val Ser Ser Leu Val Glu Gly Leu Lys Thr Arg Ala Lys Val Ser
                565                 570                 575
Arg Ala Glu Lys Lys Pro Thr Leu Gly Phe Ile Phe Thr Gly Gln
            580                 585                 590
Gly Ala Gln Trp Cys Gly Met Gly Arg Glu Leu Leu Ala Ala Tyr Pro
            595                 600                 605
Val Phe Ala Ser Ser Val Asp Ala Ile Ala Thr Tyr Leu Lys Ser Leu
            610                 615                 620
Gly Ala Pro Phe Asp Val Arg Glu Glu Leu Val Arg Asp Pro Lys Asp
625                 630                 635                 640
Ser Lys Ile Asn Gln Pro Leu Tyr Ser Gln Pro Ile Cys Thr Ala Val
                645                 650                 655
Gln Ile Ala Leu Val Asp Leu Leu Thr Phe Trp Gly Ile Arg Pro Ala
            660                 665                 670
Ser Val Thr Gly His Ser Ser Gly Glu Leu Ala Gly Ala Tyr Thr Ala
            675                 680                 685
Gly Ala Leu Ser Met Glu His Ser Met Ala Ala Tyr Tyr Arg Gly
            690                 695                 700
Val Ala Ser Ser Asp Leu Pro Arg Asp His Thr Gln Arg Gly Ala Met
705                 710                 715                 720
Met Ala Val Gly Ala Ser Lys Asp Ala Ile Gln Pro Arg Leu Ser Ser
                725                 730                 735
Leu Thr Thr Gly Thr Ala Val Val Ala Cys Val Asn Ser Pro Ser Ser
            740                 745                 750
Val Thr Ile Ser Gly Asp Ala Ser Ala Val Asp Glu Leu His Gly Leu
            755                 760                 765
Leu Glu Lys Asp Gln Val Phe Ala Arg Lys Leu Ala Val Asp Val Ala
            770                 775                 780
Tyr His Ser His His Met Lys Ala Val Ala Asp Gln Tyr Arg Thr Ala
785                 790                 795                 800
Met Ala Ala Ala Gly Val Thr Ala Val Gln Pro Glu Ser Thr Glu Pro
                805                 810                 815
Glu Val Glu Phe Phe Ser Ser Val Thr Gly Glu Lys Ala Ser Leu Thr
            820                 825                 830
Asp Leu Gly Ile Glu Tyr Trp Val Ala Asn Leu Leu Ser Gln Val Lys
            835                 840                 845
```

-continued

Phe Ala Asp Ser Val His Arg Leu Cys Met Glu Thr Ser Ala Ser Gly
          850                 855                 860
Arg Ala Arg Lys Thr Lys Thr Lys Ala Pro Lys Arg Ser Gly Ala Asn
865                 870                 875                 880
Asn Lys Ala Lys Val Asp Met Leu Val Glu Ile Gly Pro His Ser Thr
              885                 890                 895
Leu Ala Gly Pro Ile Arg Gln Ile Leu Gly Ala Asp Gln Thr Leu Glu
          900                 905                 910
Gln Ala Ser Ile Arg Tyr Ala Ser Ala Leu Leu Arg Lys Ser Ser Ala
              915                 920                 925
Val Asp Thr Thr Leu Thr Leu Ala Ser Thr Leu Leu Met Ala Gly Tyr
          930                 935                 940
Pro Ile Asp Met Ala Ala Ile Asn Arg Pro Ser Asp His His Arg Val
945                 950                 955                 960
Gly Val Leu Val Asp Leu Pro Pro Tyr Pro Trp Asn His Ser Gly Ser
              965                 970                 975
Tyr Trp Ala Glu Pro Arg Leu Ser Lys Ala Tyr Arg Asn Arg Ala His
              980                 985                 990
Pro Arg Asn Asp Leu Leu Gly Val Leu Asp Thr His Ser Ser Pro Arg
          995                 1000                1005
Glu Pro Arg Trp Arg Asn Tyr Leu Arg Thr Ser Glu Ile Pro Trp
     1010                1015                1020
Ile Lys Asp His Met Ile Gln Ser Asn Val Val Tyr Pro Ala Ala
     1025                1030                1035
Gly Tyr Leu Thr Met Ala Val Glu Ala Ile Gly Gln Arg Ile Gly
     1040                1045                1050
Asp Asn Phe Pro Gly His Arg Ile Ser Gly Tyr Arg Leu Arg Asp
     1055                1060                1065
Val Ala Ile Glu Ala Ala Leu Val Ile Ser Asp Ser Glu Pro
     1070                1075                1080
Glu Val Met Leu Ser Leu Arg Pro Ser Gly Asp Ser Gly Leu Val
     1085                1090                1095
Pro Ala Glu Arg Trp His Glu Phe His Val Leu Ser Val Thr Pro
     1100                1105                1110
Asp Asn Arg Trp Thr Glu His Cys Arg Gly Leu Ile Cys Ala Glu
     1115                1120                1125
Val Ala Ala Met Asp Gly Asp Glu Asp Asp Arg Gly Ala Glu Ala
     1130                1135                1140
Gly Leu Thr Ala Glu Thr Glu Arg Trp Ile Glu Glu Ala Glu Gln
     1145                1150                1155
Leu Cys Gln Lys Asp Val Asp Ile Pro Arg Phe Tyr Ala Glu Leu
     1160                1165                1170
Thr Gly Leu Gly Leu Glu Tyr Gly Glu Thr Phe Ala Asn Met Thr
     1175                1180                1185
Arg Ala Arg Ser Ala Ser His Val Cys Leu Ala Glu Ile Glu Val
     1190                1195                1200
Ala Asp Thr Ala Ala Val Met Pro Leu Gly Phe Gln Ser Pro Phe
     1205                1210                1215
Val Val His Pro Ser Thr Leu Asp Ser Leu Phe His Pro Leu Phe
     1220                1225                1230
Val Ala Leu Ser Ser Asp Glu Ser Leu Gln Asp Pro Ala Val Pro
     1235                1240                1245

```
Val Ala Ile Glu Glu Ile Trp Ile Arg His Gly Met Ala Lys Glu
    1250                1255                1260

Ala Gly His Lys Phe Gln Val Cys Ala Ser Thr Gln Glu Thr Gly
    1265                1270                1275

Arg Asp Arg Ile Gln Ala Ala Ile Ser Val Val Asp Ala Gln Arg
    1280                1285                1290

Ala Arg Ser Gly Pro Ala Leu Thr Val Arg Gly Leu Thr Cys Gln
    1295                1300                1305

Phe Leu Asp Arg Ala Ser Gly Asp Val Glu Gly Asp Glu Gln Pro
    1310                1315                1320

Thr Arg Leu Ala Tyr Glu Leu His Trp Glu Ala Asp Val Asp Leu
    1325                1330                1335

Leu Ser Ser Ser Asp Leu Ala Thr Leu Cys Ala Val Gly Arg Pro
    1340                1345                1350

Arg Asp Val Gly Glu Lys Val Ala Arg Tyr Val Lys Leu Leu Gly
    1355                1360                1365

His Lys Asn Pro His Leu Ala Ile Leu Glu Val Gly Ala Gly Gln
    1370                1375                1380

Gly Glu Leu Cys Ile Pro Val Phe Arg Ala Leu Ala Gly Glu Ala
    1385                1390                1395

Asn Ser Thr Pro Ser Phe Gln Ser Tyr Thr Leu Ala Asp Thr Glu
    1400                1405                1410

Pro Gly Leu Ser Glu Thr Ile Ala Thr Ile Ala Asp Gln Phe Asp
    1415                1420                1425

Glu Arg Ala Asp Leu Ile Gln Tyr Lys Glu Leu Asp Ile Ser Ser
    1430                1435                1440

Asp Pro Leu Gln Gln Gly Phe Asn Ala His Ser Leu Asp Leu Ile
    1445                1450                1455

Leu Leu Pro Ser Arg Gly Val Ser Ala Thr Leu Arg Ser Lys Ile
    1460                1465                1470

Leu Lys His Ala His Gln Leu Leu Thr Pro Glu Gly Arg Leu Ile
    1475                1480                1485

Val Val Asp Thr Arg Asp Leu Gln Glu Trp Trp Gln Ala Leu Arg
    1490                1495                1500

Glu Ser Asn Phe Thr Asp Pro Glu Val Ile His Asp Ser Pro Ser
    1505                1510                1515

Glu Thr Glu Ala Asp Ile Ser Val Leu Val Ser Lys Pro Gln Pro
    1520                1525                1530

Gln Pro Arg Asp Gln Thr Pro Ser Asp Pro Pro Asp Val Leu Val
    1535                1540                1545

Ile Ala Glu Asn Gln Asp Ser Gly Val Ser Ile Glu His Leu Gln
    1550                1555                1560

Arg Leu Leu Ala Asp Ala His Val Pro Ala Thr Val Thr Asp Phe
    1565                1570                1575

Ala His Ala Asp Pro Glu Gly Lys Thr Cys Ile Val Leu Ser Glu
    1580                1585                1590

Leu Thr Thr Ser Leu Leu Ser His Pro Asp Gln His Ser Phe Glu
    1595                1600                1605

Thr Leu Lys Arg Ile Leu Val Ala Gly Gly Arg Gly Val Leu Trp
    1610                1615                1620

Val Val Arg Gly Ala Thr Gly Pro Ala Pro Thr Ser Ser Leu Ala
    1625                1630                1635

Thr Gly Leu Leu Arg Thr Ile Arg Ser Glu Thr Asp Asp Asp Arg
```

```
                1640                1645                1650

Pro Ile Val Ser Leu Asp Leu Asp Ala Ser His Pro Leu Ser Ala
    1655                1660                1665

Glu Ser Ala Ala Gln Ser Ile Phe Ser Ala Phe Arg His Arg Phe
    1670                1675                1680

Val Ser Pro Gly Gly Ser His Glu Val Glu Tyr Ala Glu Arg Asp
    1685                1690                1695

Gly Ile Leu Arg Ile Pro Arg Val Val Glu Ser Leu Val Asn
    1700                1705                1710

His Glu Ile Val Ser Ser Leu Arg Pro Ala Val Ala Glu Asp Gln
    1715                1720                1725

Pro Phe Phe Gln Pro Gly Arg Pro Leu Glu Leu Thr Val Gly Thr
    1730                1735                1740

Pro Gly Arg Leu Asp Ser Leu Tyr Tyr Val Asp Arg Ser Cys Ile
    1745                1750                1755

Ser Glu Leu Pro Ser Asp Tyr Val Glu Ile Glu Val Lys Ala Ile
    1760                1765                1770

Gly Leu Gly Asn Gly Asp Val Lys Thr Ala Leu Gly His Asp Asp
    1775                1780                1785

Ala Ala Thr Arg Leu Gly Ala Glu Cys Ser Gly Val Val Thr Ala
    1790                1795                1800

Leu Gly Asp Ala Val Ser Gly Phe Lys Ile Gly Asp Arg Val Ala
    1805                1810                1815

Gly Phe Gly Ala Gly Thr Val Ala Thr Leu Tyr Arg Asp Gln Ala
    1820                1825                1830

Ala Arg Phe Gln Leu Ile Pro Asp Asp Met Ser Phe Ala Arg Ala
    1835                1840                1845

Ala Ala Leu Pro Val Ala Tyr Ile Thr Ala Phe Phe Ala Val His
    1850                1855                1860

Ala Leu Gly Gln Val Ser Arg Gly Asp Arg Val Leu Ile Gln Asp
    1865                1870                1875

Ala Gly Thr Ala Ala Gly Gln Ala Leu Leu Glu Leu Cys Ala Leu
    1880                1885                1890

Ala Gly Gly Asp Ile Ile Ala Val Val Asp Ser Pro Ser Gln Arg
    1895                1900                1905

Ala Phe Leu Val Gly Glu Tyr Asp Leu Pro Ala Ser Arg Ile Leu
    1910                1915                1920

Val Gly Leu Arg Gly Arg Arg Leu Ala Thr Ser Val Met Thr Leu
    1925                1930                1935

Thr Arg Gly Cys Gly Val Asp Ala Ile Phe Asn Phe Arg Gly Gly
    1940                1945                1950

Glu Glu Arg Arg Leu Cys Trp Ser Cys Val Ala Pro Tyr Gly Arg
    1955                1960                1965

Phe Ile Asp Leu Gly Gly Gly Pro Ser Asp Leu Thr Asp Met Pro
    1970                1975                1980

Gln Leu Glu Met Ala Ser Phe Phe Ser Lys Asn Ala Ser Phe Thr
    1985                1990                1995

Ala Leu Asp Phe His Tyr Leu Val Thr Gln Lys Pro Gln Ala Val
    2000                2005                2010

His Arg Ile Trp Ser Asp Val Met Ala Leu Val Arg Ala Lys Ala
    2015                2020                2025

Ile Arg Gly Pro Pro Arg Leu Gln Leu His Ser Val Ser Glu Val
    2030                2035                2040
```

-continued

```
Glu Thr Ala Leu Lys Gln Ser Gln Asp Gly Cys Asp Val Glu Lys
    2045                2050                2055

Val Val Ile Arg Ala Glu Arg Asp Thr Ile Val Gln Ala Ile Pro
    2060                2065                2070

Pro Pro Lys Gly Asp Leu Leu Arg Ala Asp Ala Ser Tyr Val Leu
    2075                2080                2085

Val Gly Gly Leu Gly Gly Ile Gly Arg Ala Met Ala Ser Trp Met
    2090                2095                2100

Ile Ala Asn Gly Ala Arg His Leu Ile Phe Val Asn Arg Ser Gly
    2105                2110                2115

Leu Ala Arg Asn Glu Ala Arg Glu Thr Val Glu Ser Leu Glu Gly
    2120                2125                2130

His Gly Ala His Val Ala Val Tyr Ser Cys Asp Val Ser Asp Arg
    2135                2140                2145

Asp Gln Val Ala Gln Met Val Ala Gln Ser Ser Lys Glu Met Pro
    2150                2155                2160

Pro Ile Arg Gly Val Ile Gln Ala Ala Met Ile Leu Arg Asp Met
    2165                2170                2175

Leu Phe Glu Lys Met Ser Val Asp Asp Phe Asn Thr Val Leu Gln
    2180                2185                2190

Pro Lys Trp Gln Gly Thr Trp Asn Leu His Gly Leu Leu Pro Arg
    2195                2200                2205

Asp Met Asp Phe Phe Ile Met Leu Ser Ser Ile Ser Gly Val Ile
    2210                2215                2220

Gly Asn Ala Thr Gln Ala Ala Tyr Ala Ala Gly Ser Thr Phe Leu
    2225                2230                2235

Gly Ala Phe Ala Gln Tyr Arg Ser Ser Leu Gly Leu Pro Ala Val
    2240                2245                2250

Thr Leu Asp Leu Gly Val Ile Thr Gly Ile Gly Tyr Leu Ser Glu
    2255                2260                2265

His Glu Glu Leu Leu Gln Gly Met Gln Arg Gln Gly Phe Glu Gly
    2270                2275                2280

Thr Asn Glu Gln Thr Leu Met Ala Leu Ile Arg Ser Ala Ile Val
    2285                2290                2295

Ser Pro Arg Arg Thr Gly Ser Gln Ala Glu Ile Val Thr Gly Leu
    2300                2305                2310

Gly Thr Trp Arg Glu Gly Val Ser Leu Gly Asn Phe Asp Gln Pro
    2315                2320                2325

Leu Phe Ala His Phe Arg Arg Gln Ala Leu Gly Leu Arg Asp Ala
    2330                2335                2340

Thr Ala Glu Gly Pro Gly Thr Ser Val Arg Glu Ser Leu Arg Gly
    2345                2350                2355

Cys Lys Thr Leu Asp Asp Ala Val Ala Leu Val Cys Ala Ala Leu
    2360                2365                2370

Ile Asp Arg Leu Ala Ser Arg Leu Asn Thr Pro Val Asp Asn Ile
    2375                2380                2385

Asp Ser Gln Arg Ala Met Ser Glu Tyr Gly Val Asp Ser Leu Val
    2390                2395                2400

Ala Val Glu Met Arg Asn Trp Ile Gly Lys Glu Met Glu Ser Thr
    2405                2410                2415

Met Pro Ile Leu Glu Leu Leu Ala Asn Gln Ser Ile Ser Gln Leu
    2420                2425                2430
```

```
Ser Glu  Lys Ile Ala Gln Arg  Ser Lys Val Val Ala  Val Ser Gly
    2435                 2440                 2445

Ser Glu  Glu
    2450
```

<210> SEQ ID NO 42
<211> LENGTH: 709
<212> TYPE: DNA
<213> ORGANISM: Paecilomyces divaricatus

<400> SEQUENCE: 42

```
atgcgtccag acttgtggct tcttctggcc ttggtgtgcc tcccttgat cgccgcccag    60 acgccaccag gatactggcc aaagaccccg aggggcctgg atgtcatatt tcgtgaccag   120
cagctcattc aaccgggcca attagtcctt cccgatggta atgtgatata ttcttccgac   180
cagtcagagc tttccccact aatatctgat tcgtgtagat gccatcgacc ccccggtatt   240
cggtcggcaa ggtctcagtg tgttccagtc ctacctcgcc gtgatgatcg acgtcgaagt   300
caaccacgaa ggcaccgcaa cgcccctggt gcactggcta cagcccgacc tgaaggtccg   360
cgatcccttc accggccggc tggcgaggtt gagtgatgag gacgtcccct atgtcggccc   420
gcgcccggtc cccggccctc gccataccta cgtgctcctt ttatttgagc agcccacgac   480
atatcgcttc cccgaatgct tctcgagcac ccggccgatc agcgtcgaca cccgctcggg   540
cttcaacctg gcccagttca tgcacgtcgc ggggttgcag gaacctattg cggcgagtta   600
tttcacggct cggaacgaag agacgccctc ggcgcctccg ccgagagtga cgacaacctc   660
gctgagtacc gcgccttgtg cgactccgac tcgatttgtc tggtgttga             709
```

<210> SEQ ID NO 43
<211> LENGTH: 215
<212> TYPE: PRT
<213> ORGANISM: Paecilomyces divaricatus

<400> SEQUENCE: 43

```
Met Arg Pro Asp Leu Trp Leu Leu Leu Ala Leu Val Cys Leu Pro Leu
1               5                   10                  15

Ile Ala Ala Gln Thr Pro Pro Gly Tyr Trp Pro Lys Thr Pro Arg Gly
            20                  25                  30

Leu Asp Val Ile Phe Arg Asp Gln Gln Leu Ile Gln Pro Gly Gln Leu
        35                  40                  45

Val Leu Pro Asp Asp Ala Ile Asp Pro Pro Val Phe Gly Arg Gln Gly
    50                  55                  60

Leu Ser Val Phe Gln Ser Tyr Leu Ala Val Met Ile Asp Val Glu Val
65                  70                  75                  80

Asn His Glu Gly Thr Ala Thr Pro Leu Val His Trp Leu Gln Pro Asp
                85                  90                  95

Leu Lys Val Arg Asp Pro Phe Thr Gly Arg Leu Ala Arg Leu Ser Asp
            100                 105                 110

Glu Asp Val Pro Tyr Val Gly Pro Arg Pro Val Pro Gly Pro Arg His
        115                 120                 125

Thr Tyr Val Leu Leu Leu Phe Glu Gln Pro Thr Thr Tyr Arg Phe Pro
    130                 135                 140

Glu Cys Phe Ser Ser Thr Arg Pro Ile Ser Val Asp Thr Arg Ser Gly
145                 150                 155                 160

Phe Asn Leu Ala Gln Phe Met His Val Ala Gly Leu Gln Glu Pro Ile
                165                 170                 175
```

```
Ala Ala Ser Tyr Phe Thr Ala Arg Asn Glu Glu Thr Pro Ser Ala Pro
            180                 185                 190

Pro Pro Arg Val Thr Thr Thr Ser Leu Ser Thr Ala Pro Cys Ala Thr
        195                 200                 205

Pro Thr Arg Phe Val Trp Cys
    210                 215

<210> SEQ ID NO 44
<211> LENGTH: 911
<212> TYPE: DNA
<213> ORGANISM: Paecilomyces divaricatus

<400> SEQUENCE: 44
atgtaccagg aagtcgactc catgatcgcc cagatagtag aagacgctgg aagcctccat     60
cgagctgttg cccaggtgga ggagttgacc ccgaagcttg ttgcagcgag tccttcctcc    120
gagaaagtac tcgtcccaat caagaaacaa atcgcagagt gcaaggcaga tctcagttcc    180
tggaataaga gaattgattc attggggcta tcgagagcga aagggatttc agcattcagg    240
aagaggttca agcaactgt ggacaggtcg ttttcgaga atgtcagaag ccggctttgc     300
ttccatcggg agcaactgac tctgctactt acaaccgccg acgcgtatgt gactctatta    360
ccttgccgtt atttatccat ctaactgttg gtcaagtaat gttggagttg agagcctccc    420
gatgacaaac aaatccgaga tacgttccaa cttcgcgtcc gggaaccggg attccaagaa    480
cctgtctcgc gtcagctcac cacgattgac aaccggataa cagatcaatc agctagtttt    540
tttcctctac tcaacggcag ttcgataggt cttcgatgg ctatttggag cagggaggac     600
aaactatatg ccgtcttgaa gctattgata cgaggttgca atgcctgcaa gcccggcttg    660
agcagtcgat caatccccaa agccagaaaa caacttacaa cccgaagaag tctagaagac    720
aagcatatgt acgacagatc ccacgcaaga cacggttgct ggagctcgtg ggctcgggaa    780
gaggtctcta tcatgctcac gaaagacaga ccgacattga agaatttcct ctgcgcgtga    840
tacagactgg gttgttgctc accgagcaaa aaggaaagat tatgtcgacc cttctcgctc    900
ttgaggattg a                                                         911

<210> SEQ ID NO 45
<211> LENGTH: 228
<212> TYPE: PRT
<213> ORGANISM: Paecilomyces divaricatus

<400> SEQUENCE: 45

Met Tyr Gln Glu Val Asp Ser Met Ile Ala Gln Ile Val Glu Asp Ala
1               5                   10                  15

Gly Ser Leu His Arg Ala Val Ala Gln Val Glu Glu Leu Thr Pro Lys
            20                  25                  30

Leu Val Ala Ala Ser Pro Ser Glu Lys Val Leu Val Pro Ile Lys
        35                  40                  45

Lys Gln Ile Ala Glu Cys Lys Ala Asp Leu Ser Ser Trp Asn Lys Arg
    50                  55                  60

Ile Asp Ser Leu Gly Leu Ser Arg Ala Lys Gly Ile Ser Ala Phe Arg
65                  70                  75                  80

Lys Arg Phe Lys Ala Thr Val Asp Arg Ser Phe Glu Asn Val Arg
                85                  90                  95

Ser Arg Leu Cys Phe His Arg Glu Gln Leu Thr Leu Leu Thr Thr
            100                 105                 110

Ala Asp Ala Phe Phe Asp Gly Tyr Leu Glu Gln Gly Gly Gln Thr Ile
```

```
            115                 120                 125
Cys Arg Leu Glu Ala Ile Asp Thr Arg Leu Gln Cys Leu Gln Ala Arg
    130                 135                 140

Leu Glu Gln Ser Ile Asn Pro Gln Ser Gln Lys Thr Thr Tyr Asn Pro
145                 150                 155                 160

Lys Lys Ser Arg Arg Gln Ala Tyr Val Arg Gln Ile Pro Arg Lys Thr
                165                 170                 175

Arg Leu Leu Glu Leu Val Gly Ser Gly Arg Gly Leu Tyr His Ala His
            180                 185                 190

Glu Arg Gln Thr Asp Ile Glu Glu Phe Pro Leu Arg Val Ile Gln Thr
        195                 200                 205

Gly Leu Leu Leu Thr Glu Gln Lys Gly Lys Ile Met Ser Thr Leu Leu
    210                 215                 220

Ala Leu Glu Asp
225

<210> SEQ ID NO 46
<211> LENGTH: 1368
<212> TYPE: DNA
<213> ORGANISM: Paecilomyces divaricatus

<400> SEQUENCE: 46
```

| | |
|---|---|
| atgtatcccg acgatgaagc tcgcaagcgc gtcgatacca tgtacatagt gtggacgagg | 60 |
| aatctgaagc agtgcttgac agagcgccta gctgccatgc tggcagcgaa gcatcgggga | 120 |
| ggcattccga tcgaggctgt cgcgtacaga gatggggcct acaatcggtg ctacaggatg | 180 |
| actttcagag aagggcccga tgccattgtg cggctcccca ttctgggaaa ggtggctctg | 240 |
| cggagagaga aagtcaacga cgagttatgc attatgggt atattacccg aaatacttcc | 300 |
| attcctcttc ccaaggtcct tggaagtggt atctgtgctg ttggccctta catggtgatg | 360 |
| aacttcgccg aagggagtcc gcttggagac tacctttcgg cgcccttgcc cgaccgtacc | 420 |
| cgagtggctg tcttggagcc ggagattagc atttccaagc tgaaaactgc gtaccgcgaa | 480 |
| atggcgagag tactgctgga gttgtcccga tctcgattct ctcgcatcgg agcacccacc | 540 |
| caaaacacag acggggcctg gtccgtctat aagcgaccat tgacatacaa cattaatgag | 600 |
| ctgctcacat acgcgaattt ccctccgcag gacctgcata aaggcccatt ttccactgca | 660 |
| aacgaatact tcttagccct cgccgaagac catctgcaac acctgcggac ccagcgcaat | 720 |
| gacgctgttg acgacgaggc ggactgcaag aagaaatatg tggcccggtg tctattcaga | 780 |
| aacattgcgc gtaacttctc gaccgcatat aataatggtc cattcagctt gttctgtgat | 840 |
| gacctgcgtc cctcaaatgt gcttgtggac tcagaccttc atatcacaag cgtcattgac | 900 |
| tgggaatact gctacgctgc accgctggag ttcacgtatt gctctccctg gtggctcctg | 960 |
| ctggcccatc cggacagctg ggagaatggg ttcaacgact tcttcaccca gtacatgccc | 1020 |
| cgacagaaga tcttcctcga agtcctgcga gagtgcgaag atgaagccgc agcccgtagc | 1080 |
| gcggttgtag actcgccgcg actgtctgag cacatggagc agtcgatcca caatggaagt | 1140 |
| ttctggtttt gccttgcggc caggtcgagc ttctcgttcg atgacattta ctgggaattc | 1200 |
| atcgatcaga gatattacgg ggagtttacc tcggttgagg atagaatggc gcttctgagt | 1260 |
| gaagaggagc gggctgaact tggtggtctt taccacctga agatggagca agaagcagag | 1320 |
| cgtaaattgg atgagcatcg gacgctagat gagatccttg cttcttga | 1368 |

<210> SEQ ID NO 47

<211> LENGTH: 455
<212> TYPE: PRT
<213> ORGANISM: Paecilomyces divaricatus

<400> SEQUENCE: 47

```
Met Tyr Pro Asp Asp Glu Ala Arg Lys Arg Val Asp Thr Met Tyr Ile
1               5                   10                  15

Val Trp Thr Arg Asn Leu Lys Gln Cys Leu Thr Glu Arg Leu Ala Ala
            20                  25                  30

Met Leu Ala Ala Lys His Arg Gly Gly Ile Pro Ile Glu Ala Val Ala
        35                  40                  45

Tyr Arg Asp Gly Ala Tyr Asn Arg Cys Tyr Arg Met Thr Phe Arg Glu
    50                  55                  60

Gly Pro Asp Ala Ile Val Arg Leu Pro Ile Leu Gly Lys Val Ala Leu
65                  70                  75                  80

Arg Arg Glu Lys Val Asn Asp Glu Leu Cys Ile Met Gly Tyr Ile Thr
                85                  90                  95

Arg Asn Thr Ser Ile Pro Leu Pro Lys Val Leu Gly Ser Gly Ile Cys
            100                 105                 110

Ala Val Gly Pro Tyr Met Val Met Asn Phe Ala Glu Gly Ser Pro Leu
        115                 120                 125

Gly Asp Tyr Leu Ser Ala Pro Leu Pro Asp Arg Thr Arg Val Ala Val
    130                 135                 140

Leu Glu Pro Glu Ile Ser Ile Ser Lys Leu Lys Thr Ala Tyr Arg Glu
145                 150                 155                 160

Met Ala Arg Val Leu Leu Glu Leu Ser Arg Ser Arg Phe Ser Arg Ile
                165                 170                 175

Gly Ala Pro Thr Gln Asn Thr Asp Gly Ala Trp Ser Val Tyr Lys Arg
            180                 185                 190

Pro Leu Thr Tyr Asn Ile Asn Glu Leu Leu Thr Tyr Ala Asn Phe Pro
        195                 200                 205

Pro Gln Asp Leu His Lys Gly Pro Phe Ser Thr Ala Asn Glu Tyr Phe
    210                 215                 220

Leu Ala Leu Ala Glu Asp His Leu Gln His Leu Arg Thr Gln Arg Asn
225                 230                 235                 240

Asp Ala Val Asp Glu Ala Asp Cys Lys Lys Lys Tyr Val Ala Arg
                245                 250                 255

Cys Leu Phe Arg Asn Ile Ala Arg Asn Phe Ser Thr Ala Tyr Asn Asn
                260                 265                 270

Gly Pro Phe Ser Leu Phe Cys Asp Asp Leu Arg Pro Ser Asn Val Leu
            275                 280                 285

Val Asp Ser Asp Leu His Ile Thr Ser Val Ile Asp Trp Glu Tyr Cys
        290                 295                 300

Tyr Ala Ala Pro Leu Glu Phe Thr Tyr Cys Ser Pro Trp Leu Leu
305                 310                 315                 320

Leu Ala His Pro Asp Ser Trp Glu Asn Gly Phe Asn Asp Phe Thr
                325                 330                 335

Gln Tyr Met Pro Arg Gln Lys Ile Phe Leu Glu Val Leu Arg Glu Cys
            340                 345                 350

Glu Asp Glu Ala Ala Arg Ser Ala Val Val Asp Ser Pro Arg Leu
        355                 360                 365

Ser Glu His Met Glu Gln Ser Ile His Asn Gly Ser Phe Trp Phe Cys
    370                 375                 380

Leu Ala Ala Arg Ser Ser Phe Ser Phe Asp Asp Ile Tyr Trp Glu Phe
```

```
            385                 390                 395                 400
Ile Asp Gln Arg Tyr Tyr Gly Glu Phe Thr Ser Val Glu Asp Arg Met
                    405                 410                 415

Ala Leu Leu Ser Glu Glu Arg Ala Glu Leu Gly Gly Leu Tyr His
                420                 425                 430

Leu Lys Met Glu Gln Glu Ala Glu Arg Lys Leu Asp Glu His Arg Thr
                435                 440                 445

Leu Asp Glu Ile Leu Ala Ser
                450                 455

<210> SEQ ID NO 48
<211> LENGTH: 20
<212> TYPE: DNA
<213> ORGANISM: Artificial Sequence
<220> FEATURE:
<223> OTHER INFORMATION: P1f primer

<400> SEQUENCE: 48
ggaataagca ggaatggttc                                              20

<210> SEQ ID NO 49
<211> LENGTH: 20
<212> TYPE: DNA
<213> ORGANISM: Artificial Sequence
<220> FEATURE:
<223> OTHER INFORMATION: P1r primer

<400> SEQUENCE: 49
cgcatccatt ctggagaaac                                              20

<210> SEQ ID NO 50
<211> LENGTH: 20
<212> TYPE: DNA
<213> ORGANISM: Artificial Sequence
<220> FEATURE:
<223> OTHER INFORMATION: P2f primer

<400> SEQUENCE: 50
cgctggatct cggcgttatc                                              20

<210> SEQ ID NO 51
<211> LENGTH: 23
<212> TYPE: DNA
<213> ORGANISM: Artificial Sequence
<220> FEATURE:
<223> OTHER INFORMATION: P2r primer

<400> SEQUENCE: 51
gctgagctat cttctccgac aac                                          23

<210> SEQ ID NO 52
<211> LENGTH: 23
<212> TYPE: DNA
<213> ORGANISM: Artificial Sequence
<220> FEATURE:
<223> OTHER INFORMATION: primer sequence

<400> SEQUENCE: 52
cgacggccag tgaattgtaa tac                                          23

<210> SEQ ID NO 53
<211> LENGTH: 20
<212> TYPE: DNA
<213> ORGANISM: Artificial Sequence
```

```
<220> FEATURE:
<223> OTHER INFORMATION: primer sequence

<400> SEQUENCE: 53
ggaggtaacc cacctttctg                                              20

<210> SEQ ID NO 54
<211> LENGTH: 20
<212> TYPE: DNA
<213> ORGANISM: Artificial Sequence
<220> FEATURE:
<223> OTHER INFORMATION: primer sequence

<400> SEQUENCE: 54
gagccacctt tcccagaatg                                              20

<210> SEQ ID NO 55
<211> LENGTH: 22
<212> TYPE: DNA
<213> ORGANISM: Artificial Sequence
<220> FEATURE:
<223> OTHER INFORMATION: primer sequence

<400> SEQUENCE: 55
gctcctatgt tgtgtggaat tg                                           22

<210> SEQ ID NO 56
<211> LENGTH: 300
<212> TYPE: DNA
<213> ORGANISM: Artificial Sequence
<220> FEATURE:
<223> OTHER INFORMATION: 300 bp homologous sequences to the 5' flanking
      region of the cornexistin/hydroxycornexistin cluster "first hook"

<400> SEQUENCE: 56
gtggttatct gagcgaattt gccggcgcag ccagggtagc tgagtacgga tgcgtgagaa    60
tattacctgt taaaggctca aaatgacaag catttcctcc tgtgggatgc aataccatct   120
tatcagaggg tccgttcact cagtgcctgc gatatttatt ggctcttgag cccctcgatt   180
atttccttat ctctcatgct catgttgagg aatctggtaa taactccctg gtgatcgctt   240
ttgcgcgaag acggcaccta ctcagtacaa cttgtgttct ttcttgacag ttttgcaaag   300

<210> SEQ ID NO 57
<211> LENGTH: 300
<212> TYPE: DNA
<213> ORGANISM: Artificial Sequence
<220> FEATURE:
<223> OTHER INFORMATION: 300 bp homologous sequences of the 3'-flanking
      region of the cornexistin/hydroxycornexistin cluster

<400> SEQUENCE: 57
ggctcaaaat gcggtgttat cgataaaaag aggctggaca accagagctt tgtagaaggg    60
aggtgaatcg gccttagaac cacccggat tgctcctctt ctactccgta taatgcgatg    120
tttggacacc agcacgatct gcaggaaaaa ggggtccctg actgaaatga ggttagcgcc   180
agaaccaggg gtgttttgga tggagtctgc tagattgatc acaacagcag atcctcctac   240
cgagtcaatg aaatatatag atgtcatgcg gatttgacta tgtctgttat tcttgcaaga   300

<210> SEQ ID NO 58
<211> LENGTH: 3382
<212> TYPE: DNA
<213> ORGANISM: Artificial Sequence
<220> FEATURE:
```

<223> OTHER INFORMATION: Plasmid pPtrpC-Pcnat1

<400> SEQUENCE: 58

| | | | | | |
|---|---|---|---|---|---|
| ctaaattgta | agcgttaata | ttttgttaaa | attcgcgtta | aattttgtt | aaatcagctc | 60 |
| atttttaac | caataggccg | aaatcggcaa | aatcccttat | aaatcaaaag | aatagaccga | 120 |
| gatagggttg | agtggccgct | acagggcgct | cccattcgcc | attcaggctg | cgcaactgtt | 180 |
| gggaagggcg | tttcggtgcg | ggcctcttcg | ctattacgcc | agctggcgaa | aggggggatgt | 240 |
| gctgcaaggc | gattaagttg | ggtaacgcca | gggttttccc | agtcacgacg | ttgtaaaacg | 300 |
| acggccagtg | agcgcgacgt | aatacgactc | actatagggc | gaattggcgg | aaggccgtca | 360 |
| aggccgcatg | agctcattta | aatgaattcg | aagttcctat | actttctaga | gataggaac | 420 |
| ttccgttaac | tgatattgaa | ggagcatttt | ttgggcttgg | ctggagctag | tggaggtcaa | 480 |
| caatgaatgc | ctattttggt | ttagtcgtcc | aggcggtgag | cacaaaattt | gtgtcgtttg | 540 |
| acaagatggt | tcatttaggc | aactggtcag | atcagcccca | cttgtagcag | tagcggcggc | 600 |
| gctcgaagtg | tgactcttat | tagcagacag | gaacgaggac | attattatca | tctgctgctt | 660 |
| ggtgcacgat | aacttggtgc | gtttgtcaag | caaggtaagt | ggacgacccg | gtcataccct | 720 |
| cttaagttcg | cccttcctcc | ctttatttca | gattcaatct | gacttaccta | ttctacctaa | 780 |
| gcattcatgg | ccaccctcga | tgacacggct | taccgctacc | gtaccagcgt | ccccggcgac | 840 |
| gccgaagcca | tcgaggccct | ggatggctct | tcaccacgg | ataccgtctt | tcgcgttacc | 900 |
| gctaccggtg | acggcttcac | gctccgtgag | gtgcccgtcg | accctcccct | gaccaaggtt | 960 |
| ttccctgatg | acgaatctga | cgatgaatcc | gacgatggcg | aggacggcga | tcccgactct | 1020 |
| cgcacgttcg | tcgcttacgg | cgatgacggt | gacctggccg | gctttgtcgt | tgtgtcctat | 1080 |
| tccggttgga | accgtcgcct | gaccgtcgaa | gacatcgagg | ttgcccccga | gcatcgcggc | 1140 |
| cacggtgtcg | gccgcgctct | catgggtctc | gccacggagt | tcgcccgtga | gcgcggcgcc | 1200 |
| ggtcacctct | ggctggaggt | taccaatgtc | aacgctcccg | ccattcacgc | ctaccgtcgc | 1260 |
| atgggcttta | ccctctgcgg | cctggatacc | gctctctacg | atggcaccgc | ctccgatggc | 1320 |
| gagcaggccc | tctatatgag | catgccttgc | ccctgagaag | ttcctatact | ttctagagaa | 1380 |
| taggaacttc | gggcccattt | aaatggtacc | ctgggcctca | tgggccttcc | gctcactgcc | 1440 |
| cgctttccag | tcgggaaacc | tgtcgtgcca | gctgcattaa | catggtcata | gctgtttcct | 1500 |
| tgcgtattgg | gcgctctccg | cttcctcgct | cactgactcg | ctgcgctcgg | tcgttcgggt | 1560 |
| aaagcctggg | gtgcctaatg | agcaaaaggc | cagcaaaagg | ccaggaaccg | taaaaaggcc | 1620 |
| gcgttgctgg | cgttttccca | taggctccgc | cccctgacg | agcatcacaa | aaatcgacgc | 1680 |
| tcaagtcaga | ggtggcgaaa | cccgacagga | ctataaagat | accaggcgtt | tccccctgga | 1740 |
| agctccctcg | tgcgctctcc | tgttccgacc | ctgccgctta | ccggatacct | gtccgccttt | 1800 |
| ctcccttcgg | gaagcgtggc | gctttctcat | agctcacgct | gtaggtatct | cagttcggtg | 1860 |
| taggtcgttc | gctccaagct | gggctgtgtg | cacgaaccc | ccgttcagcc | cgaccgctgc | 1920 |
| gccttatccg | gtaactatcg | tcttgagtcc | aacccggtaa | gacacgactt | atcgccactg | 1980 |
| gcagcagcca | ctggtaacag | gattagcaga | gcgaggtatg | taggcggtgc | tacagagttc | 2040 |
| ttgaagtggt | ggcctaacta | cggctacact | agaagaacag | tatttggtat | ctgcgctctg | 2100 |
| ctgaagccag | ttaccttcgg | aaaaagagtt | ggtagctctt | gatccggcaa | acaaaccacc | 2160 |
| gctggtagcg | gtggtttttt | tgtttgcaag | cagcagatta | cgcgcagaaa | aaaaggatct | 2220 |
| caagaagatc | ctttgatctt | ttctacgggg | tctgacgctc | agtggaacga | aaactcacgt | 2280 |

```
taagggattt tggtcatgag attatcaaaa aggatcttca cctagatcct tttaaattaa    2340
aaatgaagtt ttaaatcaat ctaaagtata tatgagtaaa cttggtctga cagttaccaa    2400
tgcttaatca gtgaggcacc tatctcagcg atctgtctat ttcgttcatc catagttgcc    2460
tgactccccg tcgtgtagat aactacgata cgggagggct taccatctgg ccccagtgct    2520
gcaatgatac cgcgagaacc acgctcaccg gctccagatt tatcagcaat aaaccagcca    2580
gccggaaggg ccgagcgcag aagtggtcct gcaactttat ccgcctccat ccagtctatt    2640
aattgttgcc gggaagctag agtaagtagt tcgccagtta atagtttgcg caacgttgtt    2700
gccattgcta caggcatcgt ggtgtcacgc tcgtcgtttg gtatggcttc attcagctcc    2760
ggttcccaac gatcaaggcg agttacatga tcccccatgt tgtgcaaaaa agcggttagc    2820
tccttcggtc ctccgatcgt tgtcagaagt aagttggccg cagtgttatc actcatggtt    2880
atggcagcac tgcataattc tcttactgtc atgccatccg taagatgctt ttctgtgact    2940
ggtgagtact caaccaagtc attctgagaa tagtgtatgc ggcgaccgag ttgctcttgc    3000
ccggcgtcaa tacgggataa taccgcgcca catagcagaa ctttaaaagt gctcatcatt    3060
ggaaaacgtt cttcggggcg aaaactctca aggatcttac cgctgttgag atccagttcg    3120
atgtaaccca ctcgtgcacc caactgatct tcagcatctt ttactttcac cagcgtttct    3180
gggtgagcaa aaacaggaag gcaaaatgcc gcaaaaaagg gaataagggc gacacggaaa    3240
tgttgaatac tcatactctt ccttttcaa tattattgaa gcatttatca gggttattgt    3300
ctcatgagcg gatacatatt tgaatgtatt tagaaaaata aacaaatagg ggttccgcgc    3360
acatttcccc gaaaagtgcc ac                                            3382
```

GENE CLUSTER FOR BIOSYNTHESIS OF CORNEXISTIN AND HYDROXYCORNEXISTIN

CROSS-REFERENCE TO RELATED APPLICATIONS

This application claims benefit (under 35 USC 119(e)) of U.S. Provisional Application No. 61/728,256, filed Nov. 20, 2012, which is incorporated by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_01589. The size of the text file is 232 KB and the text file was created on Nov. 15, 2013.

FIELD OF THE INVENTION

The invention pertains to the field of production of natural products and, in particular, in the field of production of cornexistin and hydroxycornexistin. It provides polynucleotides encoding polypeptides involved in the biosynthesis of cornexistin and hydroxycornexistin as well as vectors and recombinant microorganisms comprising such polynucleotides. Also provided are methods for the production of natural products, in particular methods for the production of cornexistin and hydroxycornexistin, using such polynucleotides and polpeptides encoded therein, as well as vectors and recombinant microorganisms comprising such polynucleotides and polypeptides.

BACKGROUND OF THE INVENTION

Cornexistin and hydroxycornexistin are natural products derived from the fungus *Paecilomyces divaricatus* formerly known as *Paecilomyces variotii* SANK21086. Both, cornexistin and hydroxycornexistin, are highly potent herbicides that have the unique quality of being harmless to corn plants. Because of this quality, both molecules have attracted research interest. Their interesting nine-membered ring structure contains a maleic anhydride and a key exocyclic ethylidene; this structure also indicates membership in the nonadride family activity and its highly functionalized structure. As part of these discovery efforts, the Sankyo Corporation discovered cornexistin during the screening of biological extracts for herbicidal use (JP2256602). Cornexistin showed good activity as a herbicide as well as relative inactivity towards corn plants. Sankyo's characterization showed this fungal natural product to be a member of the nonadride family, a group of natural products known for their interesting structural characteristics including a central nine-membered ring, fused maleic anhydrides and pendant alkyl chains. Cornexistin and hydroxycornexistin has been synthesized by chemical synthesis only as diastereomeres (Org. Biomol. Chem., 2008, 6, 4012-4025). Nine-membered carbocyclic structures in general are rare in nature and their synthesis as well as the genes involved in the synthesis are still unknown and not described.

Isolation of cornexistin from the cultures of *Paecilomyces* species originally identified as *Paecilomyces variotii* SANK21086 was published as early as 1989 by the Sankyo research group JP2256602). Later work from the DOW Elanco group described identification of hydroxycornexistin also produced in *Paecilomyces variotii* SANK 21086 (U.S. Pat. No. 5,424,78). The yield of the producing strain SANK 21086 in fermentation is believed to be too low for production purposes.

The technical problem underlying the present invention can be seen as the provision of additional means and methods for the production of cornexistin or hydroxycornexistin or for the production of cornexistin and hydroxycornexistin. The technical problem is solved by the embodiments characterized in the claims and herein below.

SUMMARY OF THE INVENTION

The invention provides for recombinant polynucleotides comprising nucleic acid sequences being at least 80% identical to the nucleic acid sequence as shown in SEQ ID NO: 1 or being at least 80% identical to the nucleic acid sequence as shown by the sequence of nucleotide 1001 to nucleotide 57525 of SEQ ID NO: 1, or being at least 80% identical to a nucleic acid sequence as shown by the sequence of nucleotide 12423 to nucleotide 52300 of SEQ ID NO: 1, or comprising a nucleic acid sequence being at least 80% identical to a nucleic acid sequence as shown in SEQ ID NOs: 2, 4, 6, 8, 10, 12, 14, 16, 18, 20, 22, 24, 26, 28, 30, 32, 34, 36, 38, 40, 42, 44 or 46, or comprising a nucleic acid sequence encoding a polypeptide having an amino acid sequence being at least 80% identical to an amino acid sequence as shown in SEQ ID NOs: 3, 5, 7, 9, 11, 13, 15, 17, 19, 21, 23, 25, 27, 29, 31, 33, 35, 37, 39, 41, 43, 45, or 47, or comprising a nucleic acid sequence comprising at least one expression cassette for at least one polypeptide having an amino acid sequence being at least 80% identical to an amino acid sequence as shown in SEQ ID NOs: 3, 5, 7, 9, 11, 13, 15, 17, 19, 21, 23, 25, 27, 29, 31, 33, 35, 37, 39, 41, 43, 45, or 47, or comprising a nucleic acid sequence being at least 70% identical to a nucleic acid sequence as shown in SEQ ID NO: 1 and comprising at least one expression cassette for at least one polypeptide having an amino acid sequence being at least 80% identical to an amino acid sequence as shown in SEQ ID NOs: 3, 5, 7, 9, 13, 15, 17, 19, 21, 23, 25, 27, 29, 31, 33, 35, 37, 39, 41, 43, 45, or 47, or comprising a nucleic acid sequence being at least 80% identical to a nucleic acid sequence as shown by the sequence of nucleotide 1001 to nucleotide 57525 of SEQ ID NO: 1 and comprising at least one expression cassette for at least one polypeptide having an amino acid sequence being at least 80% identical to an amino acid sequence as shown in SEQ ID NOs: 3, 5, 7, 9, 13, 15, 17, 19, 21, 23, 25, 27, 29, 31, 33, 35, 37, 39, 41, 43, 45, or 47, or comprising a nucleic acid sequence being at least 70% identical to the nucleic acid sequence as shown by the sequence of nucleotide 12423 to nucleotide 52300 of SEQ ID NO: 1 and comprising at least one expression cassette for at least one polypeptide having an amino acid sequence being at least 80% identical to an amino acid sequence as shown in SEQ ID NOs: 13, 15, 19, 25, 27, 29, 35, 37 and 41, or comprising a nucleic acid sequence having a combination of features of at least two of the polynucleotides described above. The invention does also provide for polynucleotides comprising a nucleic acid sequence which enables these polynucleotides to hybridize under stringent conditions to at least one of the polynucleotides described above. Further embodiments of the invention are recombinant polynucleotides as described above, comprising an expression cassette for a polypeptide having an amino acid sequence being at least 80% identical to an amino acid sequence selected from the group of sequences shown in SEQ ID NOs: 13, 15, 19, 25, 27, 29, 35, 37 and 41 and comprising at least one further expression cassette having an amino acid sequence being at least 80% identical to an amino acid sequence selected from the group of sequences shown in SEQ ID NOs: 13, 15, 19, 25, 27, 29, 35, 37 and 41. Additional embodiments are recombinant polynucleotides as described above, comprising an expression cassette for each one of the polypeptides having an amino acid sequence as shown in SEQ ID NOs: 13, 15, 19, 25, 27, 29, 35, 37 and 41. All of the polynucleotides described so far may or may not be comprised in a vector or a recombinant microorganism. Accordingly, these vectors and recombinant microorganisms are also part of the invention. The recombinant microorganisms may be bacterial, fungi or yeasts. Preferably, the recombinant microorganism is *Paecilomyces divaricatus*. Also part of the invention are processes to produce a recombinant microorganism as described above. Wherein the process comprises the following steps: a) transforming a microorganism with a polynucleotide of the invention, and b) selecting a microorganism comprising a polynucleotide of the invention. A further process of the invention is a process to produce a recombinant microorganism for the production of cornexistin or hydroxycornexistin or the production of cornexistin and hydroxycornexistin comprising the steps of: a) transforming a microorganism with at least one of the polynucleotides or vectors described above, b) selecting a microorganism comprising at least one of these polynucleotides or at least one of the vectors and selecting a recombinant microorganism producing cornexistin or hydroxycornexistin or producing cornexistin and hydroxycornexistin. Also part of the invention is a process for the production of cornexistin or hydrocornexistin or the production of cornexistin and hydroxycornexistin comprising the steps of: a) cultivating at least one of the recombinant microorganisms described above under conditions which allow for the production of cornexistin or hydroxycornexistin or cornexistin and hydroxycornexistin by said recombinant microorganism and b) obtaining all or part of the produced cornexistin or produced hydroxycornexistin or obtaining all or part of the produced cornexistin and hydroxycornexistin. Preferably, the cornexistin or hydroxycornexistin or cornexistin and hydroxycornexistin are obtained from the culture broth used to cultivate the recombinant microorganism. In further group of embodiments, at least one of cornexistin or hydroxycornexistin is obtained as dibasic acid thereof or in the form of its agriculturally acceptable salt. The recombinant polynucleotides provided by the invention can be used in a method to identify microorganisms capable to produce cornexistin or hydroxycornexistin or capable to produce cornexistin and hydroxycornexistin. Hence, a further part of the invention is a method to identify microorganisms capable to produce cornexistin or hydroxycornexistin or capable to produce cornexistin and hydroxycornexistin comprising the steps of: a) providing genomic DNA or cDNA of a microorganism or of a recombinant microorganism and b) testing the genomic DNA or cDNA for the presence of at least one polynucleotide having a nucleic acid sequence being at least 80% identical to at least one of a nucleic acid sequences as shown in SEQ ID NOs: 1, 2, 4, 6, 8, 10, 12, 14, 16, 18, 20, 22, 24, 26, 28, 30, 32, 34, 36, 38, 40, 42, 44 or 46, or encoding at least one polypeptide having an amino acid sequence being at least 80% identical to an amino acid sequence as shown in SEQ ID NOs: 3, 5, 7, 9, 13, 15, 17, 19, 21, 23, 25, 27, 29, 31, 33, 35, 37, 39, 41, 43, 45, or 47. Other parts of the invention are the use of any one of the recombinant polynucleotides described above or a vector as described above to produce a recombinant microorganism or the use in at least one of the processes or methods as described above. A further part of the invention is the use of at least one of the recombinant polynucleotides described above, or at least one of the vectors described above, or at least one of the recombinant microorganisms described above for the manufacture of cornexistin or hydroxycornexistin or for the manufacture of cornexistin and hydroxycornexistin. Also part of the invention is a method to enhance the production of cornexistin or hydroxycornexistin or cornexistin and hydroxycornexistin in *Paecilomyces divaricatus* or *Byssochlamys verrucosa* by upregulating the activity of at least one polypeptide having an amino acid sequence being at least 80%, identical to an amino acid sequence as shown in SEQ ID NOs: 13, 15, 19, 25, 27, 29, 35, 37 and 41, or having at least 80% of the sequence length of a nucleic acid sequence as shown by SEQ ID NOs: 13, 15, 19, 25, 27, 29, 35, 37 and 41. Preferably, at least two polypeptides polypeptide having an amino acid sequence being at least 80% identical to an amino acid sequence as shown in at least one of SEQ ID NOs: 13, 15, 25, 35 and 41 are upregulated. More preferred, the activity of at least one polypeptide having an amino acid sequence being at least 80%, identical to an amino acid sequence as shown in SEQ ID NOs: 13 or 25, or having at least 80% of the sequence length of a nucleic acid sequence as shown by SEQ ID NOs: 13 or 25 is upregulated.

Additional parts of the invention is a method to enhance the production of hydroxycornexistin in *Paecilomyces divaricatus* or *Byssochlamys verrucosa* by upregulating the activity of a polypeptide having an amino acid sequence being at least 80% identical to an amino acid sequence as shown in SEQ ID NO: 15, or having at least 80% of the sequence length of a nucleic acid sequence as shown by SEQ ID NOs: 15, and a method to enhance the production of cornexistin in *Paecilomyces divaricatus* or *Byssochlamys verrucosa* by downregulating the activity of a polypeptide having an amino acid sequence being at least 80% identical to an amino acid sequence as shown in SEQ ID NO: 15, or having at least 80% of the sequence length of a nucleic acid sequence as shown by SEQ ID NOs: 15.

BRIEF DESCRIPTION OF THE DRAWINGS

FIG. 1 shows a schematic drawing of the cornexistin and hydroxycornexistin gene cluster

GENERAL DEFINITIONS

The term "cornexistin" means a compound of Formula (I)

Formula (I)

The term "dibasic acid of cornexistin" means a compound of Formula (II) as well as salts of this compound, in particular agriculturally acceptable salts of a compound of Formula (IV).

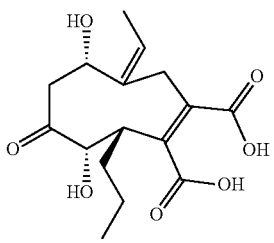

Formula (II)

The term "hydroxycornexistin" means a compound of Formula (III).

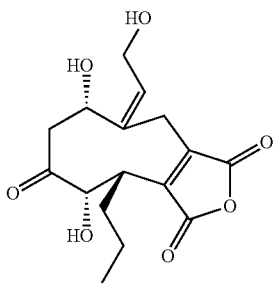

Formula (III)

The term "dibasic acid of hydroxycornexistin" means a compound of Formula (IV) as well as salts of this compound, in particular agriculturally acceptable salts of a compound of Formula (IV).

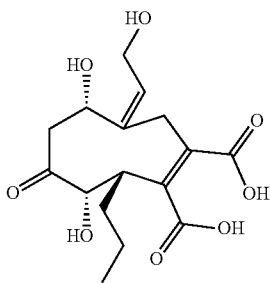

Formula (IV)

The compounds of Formulas I to IV as described herein are capable of forming geometrical isomers, for example E/Z isomers. They possess also several centers of chirality and, as a consequence, van be present as enantiomers or diastereomers. The compounds of Formulas II and IV are capable to form salts. Accordingly, the terms "cornexistin" "dibasic acid of cornexistin", "hydroxycornexistin" and "dibasic acid of hydroxycornexistin", in a broad sense, will also encompass the isomers and mixtures thereof as well as the pure enantiomers and diastereomers and their mixtures, as well as the salts of compounds of the Formula I to IV, preferably agriculturally acceptable salts of compounds of the Formula I to IV, more preferred preferably agriculturally acceptable salts of compounds of the Formula II and IV.

In a strict interpretation of the terms "cornexistin" "dibasic acid of cornexistin", "hydroxycornexistin" and "dibasic acid of hydroxycornexistin" these terms will mean compounds as described by the respective Formula I to IV and their agriculturally acceptable salts The term "agriculturally acceptable salts" is used herein to mean in general, the salts of those cations and the acid addition salts of those acids whose cations and anions, respectively, have no adverse effect on the herbicidal activity of the dibasic acid of cornexistin, the dibasic acid of hydroxycornexistin and preferably have no adverse effect on the herbicidal activity of the dibasic acid of cornexistin and the dibasic acid of hydroxycornexistin.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by C1-C4-alkyl, hydroxy-C1-C4-alkyl, C1-C4-alkoxy-C1-C4-alkyl, hydroxy-C1-C4-alkoxy-C1-C4-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2 hydroxyethylammonium (olamine salt), 2-(2-hydroxyeth-1-oxy)eth-1-ylammonium (diglycolamine salt), di(2-hydroxyeth-1-yl)-ammonium (diolamine salt), tris(2-hydroxyethyl) ammonium (trolamine salt), tris(2-hydroxypropyl) ammonium, benzyltrimethylammonium, benzyltriethylammonium, N,N,N-trimethylethanolammonium (choline salt), furthermore phosphonium ions, sulfonium ions, preferably tri(C1-C4-alkyl)sulfonium, such as trimethylsulfonium, and sulfoxonium ions, preferably tri(C1-C4-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogen¬phosphate, nitrate, bicarbonate, carbonate, hexafluorosilicate, hexafluorophosphate, benzoate and also the anions of C1-C4-alkanoic acids, preferably formate, acetate, propionate and butyrate.

The term "about" is used herein to mean approximately, roughly, around, or in the region of. When the term "about" is used in conjunction with a numerical range, it modifies that range by extending the boundaries above and below the numerical values-set forth. In general, the term "about" is used herein to modify a numerical value above and below the stated value by a variance of 20 percent up or down (higher or lower), preferably 15 percent, more preferably 10 percent and most preferably 5 percent.

The term "genome" or "gnomic DNA" is referring to the heritable genetic information of a host organism. Said genomic DNA comprises the entire genetic material of a cell or an organism, including the DNA of the nucleus (chromosomal DNA), extrachromosomal DNA, and organellar DNA (e.g. of mitochondria). Preferably, the terms genome or genomic DNA is referring to the chromosomal DNA of the nucleus.

The term "chromosomal DNA" or "chromosomal DNA sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), in situ PCR and next generation sequencing (NGS).

The term "Promoter" refers to a polynucleotide which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent, if the promoter is a constitutive promoter.

The term "Enhancer" refers to a polynucleotide. An enhancer can increase the efficiency with which a particular gene is transcribed into mRNA irrespective of the distance or orientation of the enhancer relative to the start site of transcription. Usually an enhancer is located close to a promoter, a 5'-untranslated sequence or in an intron.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

"Transgene", "transgenic" or "recombinant" refers to a polynucleotide manipulated by man or a copy or complement of a polynucleotide manipulated by man. For instance, a transgenic expression cassette comprising a promoter operably linked to a second polynucleotide may include a promoter that is heterologous to the second polynucleotide as the result of manipulation by man (e.g., by methods described in Sambrook et al., Molecular Cloning-A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, restriction sites or plasmid vector sequences manipulated by man may flank or separate the promoter from the second polynucleotide. One of skill will recognize that polynucleotides can be manipulated in many ways and are not limited to the examples above.

In case the term "recombinant" is used to specify an organism or cell, e.g. a microorganism, it is used to express that the organism or cell comprises at least one "Transgene", "transgenic" or "recombinant" polynucleotide, which is usually specified later on.

A polynucleotide "exogenous to" an individual organism is a polynucleotide which is introduced into the organism by any means other than by a sexual cross.

The terms "operable linkage" or "operably linked" are generally understood as meaning an arrangement in which a genetic control sequence, e.g. a promoter, enhancer or terminator, is capable of exerting its function with regard to a polynucletide being operably linked to it, for example a polynucleotide encoding a polypeptide. Function, in this context, may mean for example control of the expression, i.e. transcription and/or translation, of the nucleic acid sequence. Control, in this context, encompasses for example initiating, increasing, governing or suppressing the expression, i.e. transcription and, if appropriate, translation. Controlling, in turn, may be, for example, tissue- and/or time-specific. It may also be inducible, for example by certain chemicals, stress, pathogens and the like. Preferably, operable linkage is understood as meaning for example the sequential arrangement of a promoter, of the nucleic acid sequence to be expressed and, if appropriate, further regulatory elements such as, for example, a terminator, in such a way that each of the regulatory elements can fulfill its function when the nucleic acid sequence is expressed. An operably linkage does not necessarily require a direct linkage in the chemical sense. Genetic control sequences such as, for example, enhancer sequences are also capable of exerting their function on the target sequence from positions located at a distance to the polynucleotide, which is operably linked. Preferred arrangements are those in which the nucleic acid sequence to be expressed is positioned after a sequence acting as promoter so that the two sequences are linked covalently to one another. The distance between the promoter sequence and the nucleic acid sequence in an expression cassette, is preferably less than 200 base pairs, especially preferably less than 100 base pairs, very especially preferably less than 50 base pairs. The skilled worker is familiar with a variety of ways in order to obtain such an expression cassette. However, an expression cassette may also be constructed in such a way that the nucleic acid sequence to be expressed is brought under the control of an endogenous genetic control element, for example an endogenous promoter, for example by means of homologous recombination or else by random insertion. Such constructs are likewise understood as being expression cassettes for the purposes of the invention.

The term "expression cassette" means those construct in which the polynucleotide sequence to be expressed is linked operably to at least one genetic control element which enables or regulates its expression (i.e. transcription and/or translation). The expression may be, for example, stable or transient, constitutive or inducible.

The terms "express," "expressing," "expressed" and "expression" refer to expression of a gene product (e.g., a biosynthetic enzyme of a gene of a pathway or reaction defined and described in this application) at a level that the resulting enzyme activity of this protein encoded for, or the pathway or reaction that it refers to allows metabolic flux through this pathway or reaction in the organism in which this gene/pathway is expressed in. The expression can be done by genetic alteration of the microorganism that is used as a starting organism. In some embodiments, a microorganism can be genetically altered (e.g., genetically engineered) to express a gene product at an increased level relative to that produced by the starting microorganism or in a comparable microorganism which has not been altered. Genetic alteration includes, but is not limited to, altering or modifying regulatory sequences or sites associated with expression of a particular gene (e.g. by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins).

In some embodiments, a microorganism can be physically or environmentally altered to express a gene product at an increased or lower level relative to level of expression of the gene product unaltered microorganism. For example, a microorganism can be treated with, or cultured in the presence of an agent known, or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

The terms "deregulate," "deregulated" and "deregulation" refer to alteration or modification of at least one gene in a microorganism, wherein the alteration or modification results in increasing efficiency of production of a given compound in the microorganism relative to production in absence of the alteration or modification. In some embodiments, a gene that is altered or modified encodes an enzyme in a biosynthetic pathway, or a transport protein, such that the level or activity of the biosynthetic enzyme in the microorganism is altered or modified, or that the transport specificity or efficiency is altered or modified. In some embodiments, at least one gene that encodes an enzyme in a biosynthetic pathway, i.e. a polypeptide bringing about a specific activity in the biosynthetic pathway, is altered or modified such that the level or activity of the enzyme is enhanced or increased relative to the level in presence of the unaltered or wild type gene.

Deregulation also includes altering the coding region of one or more genes to yield, for example, an enzyme that is feedback resistant or has a higher or lower specific activity. Also, deregulation further encompasses genetic alteration of genes encoding transcriptional factors (e.g., activators, repressors) which regulate expression of genes coding for enzymes or transport proteins. The terms "deregulate," "deregulated" and "deregulation" can further be specified in regard to the kind of deregulation present.

In case the particular activity, is altered or modified such that the level or activity of the enzyme is enhanced or increased relative to the level in presence of the unaltered or wild type gene, the term "up-regulated" is used. In case particular activity, is altered or modified such that the level or activity of the enzyme is lowered or decreased relative to the level in presence of the unaltered or wild type gene, the term "down-regulated" is used.

The term "deregulated" includes expression of a gene product at a level lower or higher than that expressed prior to manipulation of the microorganism or in a comparable microorganism which has not been manipulated. In one embodiment, the microorganism can be genetically manipulated (e.g., genetically engineered) to express a level of gene product at a lesser or higher level than that expressed prior to manipulation of the microorganism or in a comparable microorganism which has not been manipulated. Genetic manipulation can include, but is not limited to, altering or modifying regulatory sequences or sites associated with expression of a particular gene (e.g., by removing strong promoters, inducible promoters or multiple promoters), modifying the chromosomal location of a particular gene, altering nucleic acid sequences adjacent to a particular gene such as a ribosome binding site or transcription terminator, decreasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, or other methods to knock-out or block expression of the target protein). The term "deregulated gene activity" also means that a gene activity is introduced into a microorganism where the respective gene activity, e.g. the lysine decarboxylase activity, has not been observed before, e.g. by introducing a recombinant gene, e.g. a heterologous gene, in one or more copies into the microorganism preferably by means of genetic engineering.

The phrase "deregulated pathway or reaction" refers to a biosynthetic pathway or reaction in which at least one gene that encodes an enzyme in a biosynthetic pathway or reaction is altered or modified such that the level or activity of at least one biosynthetic enzyme is altered or moVied. The phrase "deregulated pathway" includes a biosynthetic pathway in which more than one gene has been altered or modified, thereby altering level and/or activity of the corresponding gene products/enzymes. In some cases the ability to "deregulate" a pathway (e.g., to simultaneously deregulate more than one gene in a given biosynthetic pathway) in a microorganism arises from the particular phenomenon of microorganisms in which more than one enzyme (e.g., two or three biosynthetic enzymes) are encoded by genes occurring adjacent to one another on a contiguous piece of genetic material termed a "cluster" or "gene cluster" In other cases, in order to deregulate a pathway, a number of genes must be deregulated in a series of sequential engineering steps.

To express the deregulated genes according to the invention, the DNA sequence encoding the polypeptide must be operably linked to regulatory sequences that control transcriptional expression in an expression vector and then, introduced into either microorganism. In addition to transcriptional regulatory sequences, such as promoters and enhancers, expression vectors can include translational regulatory sequences and a marker gene which is suitable for selection of cells that carry the expression vector.

The terms "overexpress", "overexpressing", "overexpressed" and "overexpression" refer to expression of a gene product, in particular to enhancing the expression of a gene product at a level greater than that present prior to a genetic alteration of the starting microorganism. In some embodiments, a microorganism can be genetically altered (e.g., genetically engineered) to express a gene product at an increased level relative to that produced by the starting microorganism. Genetic alteration includes, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins). Another way to overexpress a gene product is to enhance the stability of the gene product to increase its life time.

The term "sequence identity" between two nucleic acid sequences is understood as meaning the percent identity of the nucleic acid sequence over in each case the entire sequence length which is calculated by alignment with the aid of the program algorithm GAP (Wisconsin Package Version 10.0, University of Wisconsin, Genetics Computer Group (GCG), Madison, USA), setting the following parameters:
Gap Weight: 12 Length Weight: 4
Average Match: 2,912 Average Mismatch:−2,003

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002) & The Pfam protein families database: R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily/be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimizms e alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

Typically, this involves a first BLAST involving BLASTing a query sequence (for example using any of the sequences listed in Table A of the Examples section) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived. The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The $T_m$ may be calculated using the following equations, depending on the types of hybrids:

1) DNA-DNA hybrids (Meinkoth and Wahl, Anal. Biochem., 138: 267-284, 1984):
$T_m=81.5°$ C.$+16.6 \times \log_{10}$ [Na$^+$]$^a+0.41 \times \%$[G/C$^b$]$-500 \times$ [L$^c$]$^{-1}-0.61 \times \%$ formamide 2) DNA-RNA or RNA-RNA hybrids:
$T_m=79.8°$ C.$+18.5$ ($\log_{10}$ [Na$^+$]$^a$)$+0.58$ (% G/C$^b$)$+11.8$ (% G/C$^b$)$^2-820/L^c$ 3) oligo-DNA or oligo-RNA$^d$ hybrids:
For <20 nucleotides: $T_m=2$ (I$_n$)
For 20-35 nucleotides: $T_m=22+1.46$ (I$_n$)

$^a$ or for other monovalent cation, but only accurate in the 0.01-0.4 M range.
$^b$ only accurate for % GC in the 30% to 75% range.
$^c$ L=length of duplex in base pairs.
$^d$ oligo, oligonucleotide; I$_n$,=effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions. For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate. For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag• 100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions | Residue | Conservative Substitutions |
|---------|---------------------------|---------|---------------------------|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Reference herein to an "endogenous" gene not only refers to the gene in question as found in an organism in its natural form (i.e., without there being any human intervention), but also refers to that same gene (or a substantially homologous nucleic acid/gene) in an isolated form subsequently (re) introduced into a microorganism (a transgene). For example, a transgenic microorganism containing such a transgene may encounter a substantial reduction of the transgene expression and/or substantial reduction of expression of the endogenous gene. The isolated gene may be isolated from an organism or may be manmade, for example by chemical synthesis.

The terms "orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

The term "vector", preferably, encompasses phage, plasmid, fosmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a recombinant microorganism. The vector may be incorporated into a recombinant microorganism by various techniques well known in the art. If introduced into a recombinant microorganism, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a recombinant microorganism, including calcium phosphate, rubidium chloride or calcium chloride co-precipitation, DEAE-dextran-mediated transfection, lipofection, natural competence, carbon-based clusters, chemically mediated transfer, electroporation or particle bombardment. Methods for many species of microorganisms are readily available in the literature, for example, in Turgeon (2010) Molecular and cell biology methods for fungi, p 3-9, in Koushki, M M et al., (2011), AFRICAN JOURNAL OF BIOTECHNOLOGY Vol. 10 (41): p 7939-7948, in Coyle et al. (2010) Appl Environ Microbiol 76:3898-3903, in Current Protocols in Molecular Biology, Chapter 13. Eds Ausubel F. M. et al. Wiley & Sons, U.K., and in Genome Analysis: A Laboratory Manual, Cloning Systems. Volume 3. Edited by Birren B, Green E D, Klapholz S, Myers R M, Riethman H, Roskams J. New York: Cold Spring Harbor Laboratory Press; 1999: 297-565.

DETAILED DESCRIPTION OF PREFERRED EMBODIMENTS

In a first aspect, the present invention provides nucleic acid sequences which encodes a polypeptide being involved in the cornexistin and hydroxycornexistin synthesis As used herein, cornexistin and hydroxycornexistin synthesis encompasses all steps of the biosynthesis of cornexistin and hydroxycornexistin. Accordingly, a polypeptide which is involved in the synthesis of cornexistin and hydroxycornexistin may either convert a substrate into cornexistin and hydroxycornexistin or any of the precursors which occur in the cornexistin and hydroxycornexistin biosynthesis. Preferably, the polypeptide encoded by the polynucleotide of the present invention shall be capable of increasing the amount of cornexistin and hydroxycornexistin or a precursor thereof upon expression in an organism, preferably a recombinant microorganism as specified elsewhere herein. Such an increase is, preferably, statistically significant when compared to a control organism which lacks expression of the polynucleotide of the present invention. Whether an increase is significant can be determined by statistical tests well known in the art including, e.g., Student's t-test. More preferably, the increase is an increase of the amount of cornexistin and hydroxycornexistin of at least 5%, at least 10%, at least 15%, at least 20% or at least 30% compared to said control. Suitable assays to identify and measure the amount of cornexistin and hydroxycornexistin are known by the person skilled in the art and are described for example in U.S. Pat. Nos. 4,897,104, 4,990,178, 5,424,278 and in the accompanying Examples.

One nucleic acid sequences provided by the invention is a gene cluster described by SEQ ID NO: 1, which comprises expression cassette for polypeptides being involved in cornexistin and hydroxycornexistin synthesis. A schematic representation of the gene cluster is provided by FIG. 1.

TABLE 2

Listing of genes and encoded polypeptides of the sequence of SEQ ID NO: 1:

| Gene Name (ORF) | Starting point in SEQ ID No 1 | Endpoint in SEQ ID No 1 | Seq ID NO: | Function | Corresponding protein Seq ID NO: |
|---|---|---|---|---|---|
| 1_9399 | 1001 | 4395 | 2 | AMP binding protein, phospopantheine binding protein | 3 |
| 2_9399 | 4937 | 5965 | 4 | protein | 5 |
| 3_9399 | 8236 | 7505 | 6 | protein | 7 |
| 4_9399 | 10368 | 9322 | 8 | Alkohol/keto oxido-reductase | 9 |
| 5_9399 | 11274 | 11354 | 10 | protein | 11 |
| 6_9399 | 12423 | 14345 | 12 | Transketolase | 13 |
| 7_9399 | 17599 | 15965 | 14 | Cytochrom P450 oxygenase | 15 |
| 8_9399 | 18123 | 19631 | 16 | Sugar transporter | 17 |
| 9_9399 | 21831 | 20880 | 18 | Lactone hydrolase protein | 19 |
| 10_9399 | 23763 | 22165 | 20 | Transporter protein | 21 |
| 11_9399 | 24308 | 26347 | 22 | protein | 23 |
| 12_9399 | 28222 | 26750 | 24 | Transcriptional regulator protein | 25 |
| 13_9399 | 29894 | 31024 | 26 | Gluconolactonase protein | 27 |
| 14_9399 | 32996 | 31399 | 28 | Citrate synthase protein | 29 |
| 15_9399 | 35799 | 34706 | 30 | Dioxygenase protein | 31 |
| 16_9399 | 39097 | 37437 | 32 | Transporter protein | 33 |
| 17_9399 | 39414 | 40500 | 34 | Polyketide cyclase protein | 35 |
| 18_9399 | 42510 | 40981 | 36 | Methylcitrate dehydratase protein | 37 |
| 19_9399 | 42995 | 43808 | 38 | Thioesterase protein | 39 |
| 20_9399 | 44518 | 52300 | 40 | Polyketide synthase protein | 41 |
| 21_9399 | 53415 | 52707 | 42 | protein | 43 |
| 22_9399 | 54385 | 55295 | 44 | protein | 45 |
| 23_9399 | 57525 | 56158 | 46 | Phosphotransferase protein | 47 |

Table 2 provides a listing of the polypeptide (protein) encoding sequences of SEQ ID NO: 1, the respective ORF names, the number of the nucleotides in SEQ ID NO: 1, which are starting and endpoints of the polypeptide encoding sequences, the likely function of the encoded polypeptides and the respective SEQ ID NOs: of the polynucleotide and amino acid sequences in the sequence listings.

The provided polynucleotides recombinant polynucleotides can either be isolated from their natural genomic environment, modified after their isolation or produced artificially from pure sequence information. A natural source of polynucleotides of the invention are cornexistin or hydroycornexistin producing fungi and related species. Such fungi can, for example, be found in the group consisting of the genus *Paecilomyces*, the genus *Byssochlamys*, the genus *Thermoascus* and the genus *Monascus* for example the species *Byssochlamys verrucosa, Byssochlamys nivea, Paecilomyces divaricatus, Paecilomyces Thermoascus crustaceus, Thermoascus thermophilus* and *Thermoascus auraniacus*. Of particular interest are fungi of the species: *Paecilomyces divaricatus* and *Byssochlamys verrucosa*. Strains of these species are deposited, for example, at the CBS Fungal Biodiversity Centre as: *Byssochlamys verrucosa* CBS 605.74 isolated in Australia, *Paecilomyces divaricatus* CBS 284.48 isolated in the USA and *Paecilomyces divaricatus* CBS 110429 isolated in Mexico. A most preferred strain of *Paecilomyces variotii* has been deposited under Ministry of International Trade and Industry Japan deposit number FERM BP-1351 and deposited at the American Type Culture Collection under accession number ATTC 74268, both being derived from *Paecilomyces variotii* Bainier SANK 21086, having been isolated from deer faeces collected in Canada.

Further information for the selection of suitable organisms can, for example, be found in Mutsuo Nakajima et al.; CORNEXISTIN: A NEW FUNGAL METABOLITE WITH HERBICIDAL ACTIVITY; THE JOURNAL OF ANTIBIOTICS, VOL. 44 NO. 10, 1991: page 1065-1072, in U.S. Pat. Nos. 4,897,104, 4,990,178, 5,424,278 and in R. A. Samson et al. "Polyphasic taxonomy of the heat resistant ascomycete genus *Byssochlamys* and its *Paecilomyces* anamorphs" Persoonia 22, 2009: pages 14-27.

The sequence information of polynucleotides isolated from the natural sources described above can be used to isolate homologous polynucleotides and allelic or splice variants of the genes, promoter and terminator sequences comprised by SEQ ID NO: 1, as well as homologous polynucleotides and allelic variants of SEQ ID NO: 1. Further variants of the disclosed polynucleotides can be constructed, e.g. by adapting the codon usage of polypeptide encoding polynucleotide sequences to the codon usage of a preferred species of microorganism, or by exchanging promoter regions and/or terminator regions or both of an expression cassette in order to adapt the expression of an encoded polynucleotide to a preferred species of microorganism or culture conditions.

Further variants of the polynucleotides of the invention can be created by adding, deleting one or more polynucleotides from a polynucleotide, e.g. by shortening spacer regions between expression cassettes, by deleting introns, or deleting one or more codons of polypeptide encoding regions or complete functional elements of the polynucleotides, like complete, promoter, terminator or polypeptide encoding regions or complete expression cassettes. Alternatively, or in addition thereto, is possible to create variants of the encoded polypeptide sequences, e.g. by introducing conserved amino acid substitutions or by adding or deleting one or more codons in order to enlarge or shorten the encoded polypeptides, or to create polypeptide fusions. Preferred polypeptide fusion comprise polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like. The variant nucleic acid sequence shall still encode a polypeptide being involved in cornexistin and hydroxycornexistin synthesis. Accordingly, the polypeptide encoded by the variant in sequence length may comprise or consist of the domains of the polypeptide of the present invention conferring the said biological activity.

Variants in sequence identity and sequence length also encompass polynucleotides comprising a nucleic acid sequence which is capable of hybridizing to the aforementioned specific nucleic acid sequences, preferably, under stringent hybridization conditions. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used.

Accordingly, the polynucleotide and amino acid sequence information disclosed herein and in the sequence listing, can be used to identify or create variants in sequence identity and sequence length comprising a nucleic acid sequence being at least 80%, 82%, 84%, 86%, 88%, 90%, 91%, 92%, 93%, 94%, 95%, 96%, 97%, 98%, 99%, or 100% identical to the nucleic acid sequences and amino acid sequences disclosed herein or can be used to identify or create sequence variants comprising a nucleic acid sequence or amino acid sequence having at least 80%, 82%, 84%, 86%, 88%, 90%, 91%, 92%, 93%, 94%, 95%, 96%, 97%, 98%, 99%, or 100% of the sequence length of the respective nucleic acid sequence or amino acid sequence disclosed herein.

The variants in sequence identity or sequence length referred to above, preferably, encode polypeptides retaining a significant extent, preferably, at least 10%, at least 20%, at least 30%, at least 40%, at least 50%, at least 60%, at least 70%, at least 80% or at least 90% of the activity exhibited by any of the polypeptide shown in any one of SEQ ID NOs: 3, 5, 7, 9, 11, 13, 15, 17, 19, 21, 23, 25, 27, 29; 31, 33, 35, 37, 39, 41, 43, 45, 47. The activity may be tested as described in the accompanying Examples, or by replacing the polynucleotide sequence in Paecilomyces divaricatus having the same activity with the respective variant in sequence identity or sequence length, culturing the recombinant Paecilomyces divaricatus cells under conditions which allow for the production of cornexistin, hydroxycornexistin or both and comparing the amount of cornexistin, hydroxycornexistin or both with the amount of the cornexistin, hydroxycornexistin or both produced by the non-recombinant Paecilomyces divaricatus cultured under the same conditions. Preferably the amount of cornexistin is compared for polypeptides involved in cornexistin biosynthesis, while the amount of hydroxycornexistin is compared for polypeptides involved in hydroxycornexistin biosynthesis. The activity of polypeptides involved in cornexistin and hydroxycornexistin biosynthesis is measured by comparing the amount of the produced cornexistin.

Thus, the invention encompasses recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to the nucleic acid sequence as shown in SEQ ID NO: 1, or having at least 80%, 82%, 84%, 86%, 88%, 90%, 91%, 92%, 93%, 94%, 95%, 96%, 97%, 98%, 99%, or 100% of the sequence length of the nucleic acid sequence as shown in SEQ ID NO: 1, as well as polynucleotides comprising a nucleic acid sequence being at least 80%, 82%, 84%, 86%, 88%, 90%, 91%, 92%, 93%, 94%, 95%, 96%, 97%, 98%, 99%, or 100% identical to the nucleic acid sequence as shown by the sequence of nucleotide 1001 to nucleotide 57525 of SEQ ID NO: 1 or having at least 80%, 82%, 84%, 86%, 88%, 90%, 91%, 92%, 93%, 94%, 95%, 96%, 97%, 98%, 99%, or 100% of the sequence length of the nucleic acid sequence as shown by the sequence of nucleotide 1001 to nucleotide 57525 of SEQ ID NO: 1, and polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown by the sequence of nucleotide 12423 to nucleotide 52300 of SEQ ID NO: 1, or having at least 80%, 82%, 84%, 86%, 88%, 90%, 91%, 92%, 93%, 94%, 95%, 96%, 97%, 98%, 99%, or 100% of the sequence length of the nucleic acid sequence as shown by the sequence of nucleotide 12423 to nucleotide 52300 of SEQ ID NO: 1

Further recombinant polynucleotides provided by the invention are polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 2 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 2, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 4 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 4, recombinant polynucleotides comprising a nucleic acid sequence being at least 80%, 82%, 84%, 86%, 88%, 90%, 91,%, 92%, 93%, 94%, 95%, 96%, 97%, 98%, 99%, or 100% identical to a nucleic acid sequence as shown in SEQ ID NO: 6 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 6, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 8 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 8, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 10 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 10, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 12 or having at least 80%, 82%, 84%, 86%, 88%, 90%, 91%, 92%, 93%, 94%, 95%, 96%, 97%, 98%, 99%, 100% of the sequence length of a nucleic acid sequence as shown by SEQ ID NO: 12, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 14 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 14, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 16 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 16, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 18 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 18, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 20 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 20, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 22 or having at least 80%, 82%, 84%, 86%, 88%, 99%, 91%, 92%, 93%, 94%, 95%, 96%, 97%, 98%, 99%, or 100% of the sequence length of a nucleic acid sequence as shown by SEQ ID NO: 22, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 24 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 24, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 26 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 26, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 28 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 28, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 30 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 30, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 32 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 32, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 34 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 34, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 36 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 36, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 38 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 38, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 40 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 40, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 42 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 42, recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 44 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 44, and recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 46 or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NO: 46.

Other recombinant polynucleotides provided by the invention are recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 3, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 3, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 5, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 5, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 7, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 7, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 9, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 9, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 11, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 11, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 13, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 13, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 15, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 15, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 17, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 17, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 19, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 19, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 21, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 21, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 23, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 23, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 25, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 25, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 27, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 27, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 29, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 29, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 31, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 31, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 33, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 33, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 35, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 35, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 37, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 37, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 39, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 39, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 41, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 41, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 43, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 43, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 45, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 45, and recombinant polynucleotides comprising at least one nucleic acid sequence encoding at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NO: 47, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by an amino acid sequence as shown in SEQ ID NO: 47.

A further embodiment of the invention are polynucleotides comprising a nucleic acid sequence comprising at least one or more expression cassettes for at least one, two, three, four, five, six, seven, eight, nine, ten, eleven, twelve, thirteen, fourteen, fifteen, sixteen, seventeen, eighteen, nineteen, twenty, twenty one, twenty two or all of the polypeptides described by SEQ ID NOs: 3, 5, 7, 9, 11, 13, 15, 17, 19, 21, 23, 25, 27, 29, 31, 33, 35, 37, 39, 41, 43, 45, and 47, or their variants in sequence identity and sequence length.

In one embodiment of the invention the polynucleotide comprises a nucleic acid sequence comprising at least one or more expression cassettes for at least one, two, three, four, five, six, seven, eight, nine, ten, eleven, twelve, thirteen, fourteen or all of the polypeptides described by SEQ ID NOs: 13, 15, 17, 19, 21, 23, 25, 27, 29, 31, 33, 35, 37, 39, and 41, or their variants in sequence identity and sequence length.

In one embodiment of the invention the polynucleotide comprises a nucleic acid sequence comprising at least one or more expression cassettes for at least one, two, three, four, five, six, seven, eight or all of the polypeptides described by SEQ ID NOs: 13, 15, 19, 25, 27, 29, 35, 37 and 41, or their variants in sequence identity and sequence.

In one embodiment of the invention the polynucleotide comprises a nucleic acid sequence comprising at least one or more expression cassettes for at least one, two, three or all of the polypeptides described by SEQ ID NOs: 13, 15, 37 and 41, or their variants in sequence identity and sequence length.

In one embodiment of the invention the polynucleotide comprises a nucleic acid sequence comprising at least one or more expression cassettes for at least one, two or all of the polypeptides described by SEQ ID NOs: 17, 21 and 33, or their variants in sequence identity and sequence length.

In one embodiment of the invention the polynucleotide comprises a nucleic acid sequence comprising at least one or more expression cassettes for at least one or both of the polypeptides described by SEQ ID NOs: 13 and 15, or their variants in sequence identity and sequence length.

In one embodiment of the invention the polynucleotide comprises a nucleic acid sequence comprising at least one or more expression cassettes for at least one or both of the polypeptides described by SEQ ID NOs: 19 and 27 or their variants in sequence identity and sequence length.

In one embodiment of the invention the polynucleotide comprises a nucleic acid sequence comprising at least one or more expression cassettes for at least one or both of the polypeptides described by SEQ ID NOs: 29 and 37 or their variants in sequence identity and sequence length.

In one embodiment of the invention the polynucleotide comprises a nucleic acid sequence comprising at least one or more expression cassettes for at least one or both of the polypeptides described by SEQ ID NOs: 35 and 41, or their variants in sequence identity and sequence length.

In one embodiment of the invention the polynucleotide comprises a nucleic acid sequence comprising at least one or more expression cassettes for a polypeptide described by SEQ ID NOs: 13, or its variants in sequence identity and sequence length.

In one embodiment of the invention the polynucleotide comprises a nucleic acid sequence comprising at least one or more expression cassettes for a polypeptide described by SEQ ID NOs: 15, or its variants in sequence identity and sequence length.

In one embodiment of the invention the polynucleotide comprises a nucleic acid sequence comprising at least one or more expression cassettes for a polypeptide described by SEQ ID NOs: 25, or its variants in sequence identity and sequence length.

In one embodiment of the invention the polynucleotide comprises a nucleic acid sequence comprising at least one or more expression cassettes for a polypeptide described by SEQ ID NOs: 41, or its variants in sequence identity and sequence length.

Examples for polynucleotides as described above are polynucleotides comprising a nucleic acid sequence comprising at least one expression cassette for at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NOs: 13, 15, 19, 25, 27, 29, 35, 37 and 41, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NOs: 13, 15, 19, 25, 27, 29, 35, 37 and 41.

A further example of such polynucleotides are polynucleotides comprising an expression cassette for a polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence selected from the group of sequences shown in SEQ ID NOs: 13, 15, 19, 25, 27, 29, 35, 37 and 41 and comprising at least one further expression cassette having an amino acid sequence being at least 80%, 82%, 84%, 86%, 88%, 90%, 91%, 92%, 93%, 94%, 95%, 96%, 97%, 98%, 99%, or 100% identical to an amino acid sequence selected from the group of sequences shown in SEQ ID NOs: 13, 15, 19, 25, 27, 29, 35, 37 and 41.

Another example of such polynucleotides are polynucleotide comprising an expression cassette for each one of the polypeptides having an amino acid sequence as shown in SEQ ID NOs: 13, 15, 19, 25, 27, 29, 35, 37 and 41.

These examples are only meant to illustrate the principle of design of these polynucleotides and should not be interpreted as limiting.

A further embodiment of the invention are polynucleotides comprising a nucleic acid sequence being at least 70%, 72%, 74%, 76%, 78%, 80%, 82%, 84%, 86%, 88%, 90%, 91%, 92%, 93%, 94%, 95%, 96%, 97%, 98%, 99%, or 100% identical to a nucleic acid sequence as shown in SEQ ID NO: 1 and comprising at least one expression cassette for at least one, two, three, four, five, six, seven, eight, nine, ten, eleven, twelve, thirteen, fourteen, fifteen, sixteen, seventeen, eighteen, nineteen, twenty, twenty one, twenty two or all of the polypeptides described by SEQ ID NOs: 3, 5, 7, 9, 11, 13, 15, 17, 19, 21, 23, 25, 27, 29, 31, 33, 35, 37, 39, 41, 43, 45, and 47, or their variants in sequence identity and sequence length, or polynucleotides comprising a nucleic acid sequence being at least 70%, 72%, 74%, 76%, 78%, 80%, 82%, 84%, 86%, 88%, 90%, 91%, 92%, 93%, 94%, 95%, 96%, 97%, 98%, 99%, or 100% identical to a nucleic acid sequence as shown by the sequence of nucleotide 1001 to nucleotide 57525 of SEQ ID NO: 1 and comprising at least one expression cassette for at least one, two, three, four, five, six, seven, eight, nine, ten, eleven, twelve, thirteen, fourteen, fifteen, sixteen, seventeen, eighteen, nineteen, twenty, twenty one, twenty two or all polypeptides having an amino acid sequence as shown in SEQ ID NOs: 3, 5, 7, 9, 13, 15, 17, 19, 21, 23, 25, 27, 29; 31, 33, 35, 37, 39, 41, 43, 45, or 47, or their variants in sequence identity and sequence length, or polynucleotides comprising a nucleic acid sequence being at least 70%, 72%, 74%, 76%, 78%, 80%, 82%, 84%, 86%, 88%, 90%, 91%, 92%, 93%, 94%, 95%, 96%, 97%, 98%, 99%, or 100% identical to the nucleic acid sequence as shown by the sequence of nucleotide 12423 to nucleotide 52300 of SEQ ID NO: 1 and comprising at least one expression cassette for at least one, two, three, four, five, six, seven, eight, or all polypeptides having an amino acid sequence as shown in SEQ ID NOs: 13, 15, 19, 25, 27, 29, 35, 37 and 41, or their variants in sequence identity and sequence length.

Further embodiments of the invention are polynucleotides having a combination of the features of any polynucleotide described above, as well as polynucleotides having a nucleic acid sequence which enables the polynucleotide to hybridize under stringent conditions to any one of these polynucleotides, preferably polynucleotides able to hybridize to a polynucleotide comprising a nucleic acid sequence as shown in SEQ ID NOs: 1, 2, 4, 6, 8, 10, 12, 14, 16, 18, 20, 22, 24, 26, 28, 30, 32, 34, 36, 38, 40, 42, 44 or 46.

It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides. However, the present invention also pertains to polynucleotide variants which are derived from the polynucleotides of the present invention and are capable of interfering with the transcription or translation of the polynucleotides of the present invention. Such variant polynucleotides include anti-sense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

Another embodiment of the invention are vectors comprising any one of the polynucleotides described above.

Preferably, the vector referred to herein is suitable as a cloning vector or transformation vector, i.e. replicable in microbial systems or able to integrate polynucleotides into the genome of a microorganism. Also preferably, the vector of the present invention is an expression vector. Expression vectors comprise expression cassettes which enable the transcription and translation of the polynucleotides in the respective microorganism. The expression cassettes comprise a promoter and a terminator being operably linked to the polynucleotide coding for at least one polypeptide of the invention. The polynucleotides encoding at least one of the polypeptides will preferably be adapted to the codon usage of the respective microorganism. Promoters, terminators and information about codon usage suitable to be used for a particular microorganism are known by a person skilled in the art. Suitable promoter sequences for yeast or fungal species are: ADC1, AOX1r, GAL1, MFα, AC, P-60, CYC1, GAPDH, TEF, rp28, ADH trpC, GAL10, cbh1, hfb2 amyB. Further examples can be taken from MICROBIOLOGY AND MOLECULAR BIOLOGY REVIEWS 70, Pages: 583-ff 2006. The expression cassettes may comprise constitutive or inducible promoters. For example, suitable constitutive promoters for yeasts, in particular for *Saccharomyces cerevisiae* are for example the trpC, gpdA, tub2 and Tef1 promoters. Suitable inducible promoters for yeasts, in particular for *Saccharomyces cerevisiae*, are for ex-ample the Gal1, Gal10, Cup1, Pho5, and Met25 promoters. Further Promoters and terminators, as well as cloning strategies are described, for example, in Shao et al. (2009) Nucleic Acids Research, Vol. 37, No. 2 e16 (10 pages). In one embodiment of the invention the expression cassettes comprise promoter sequences comprised by SEQ ID NO: 1.

It will be clear to a person skilled in the art, that sequences located upstream of starting nucleotides of genes of SEQ ID NO: 1 will be able to provide promoter functions in fungi, in particular in fungi of the genus *Paecilomyces* and the species *Paecilomyces divaricatus*. It will also be clear to a person skilled in the art, that sequences located downstream of end point nucleotides of genes of SEQ ID NO: 1 will be able to provide terminator functions in fungi, in particular in fungi of the genus *Paecilomyces* and the species *Paecilomyces divaricatus*.

Accordingly, a further embodiment of the invention are fragments of SEQ ID NO: 1 of about 2000, 1750, 1500, 1250, 1000, 750, 500, 300 or 250 nucleotides upstream of a starting nucleotide of each gene of SEQ ID NO: 1 having promoter function in *Paecilomyces divaricatus*, as well as fragments of SEQ ID NO: 1 of about 500, 300, or 250 nucleotides downstream of a endpoint nucleotide of each gene of SEQ ID NO: 1 having terminator function in *Paecilomyces divaricatus*, as well as recombinant expression cassettes, vectors and recombinant microorganisms comprising at least one of these fragments.

Preferred expression vectors are known in the art. These vectors are, for example, in *E. coli*, pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, lambda-gt11 or pBdCI, in *Streptomyces* pIJ101, pIJ364, pIJ702 or pIJ361, in *Bacillus* pUB110, pC194 or pBD214. Examples of vectors for expression in the yeast *S. cerevisiae* comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Further suitable yeast vectors are, for example, pAG-1, YEp6, YEp13 or pEM-BLYe23. Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego).

The present invention also relates to a method for the production of a polypeptide encoded by a polynucleotide of the present invention comprising
  a) cultivating the recombinant microorganism of the present invention under conditions which allow for the production of the said polypeptide; and
  b) obtaining the polypeptide from the recombinant microorganism of step a).

Suitable conditions which allow for expression of the polynucleotide of the invention comprised by the recombinant microorganism depend on the recombinant microorganism as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the recombinant microorganism which is used for the aforementioned method, the polypeptides produced thereby may become posttranslationally modified or processed otherwise.

Another group of embodiments of the invention are the polypeptide encoded by a polynucleotide of the present invention or a polypeptide which is obtainable by the aforementioned method of the present invention.

The polynucleotides and vectors of the present invention are particularly suitable for the production of cornexistin and hydroxycornexistin in microorganisms, which comprise at least one of the polynucleotides described above in addition to their natural set of genes or polynucleotides. Accordingly, further embodiments of the invention are recombinant microorganisms comprising at least one of the polynucleotides of the invention. This additional polynucleotide can be comprised by a vector or can be integrated in the genome of the microorganism.

Preferably, said recombinant microorganism is a bacterium, an actinomycete, a yeast, a fungus, such as an ascomycete, a deuteromycete, or a basidiomycete, preferably the recombinant microorganism is a bacterial cell, a fungi cell or a yeast cell.

Preferred bacteria to be used as recombinant microorganisms of the present invention are selected from the group consisting of: *Escherichia coli* and *Bacllus subtills*.

Preferred fungi are selected from the group consisting of: the genus *Paecilomyces*, the genus *Byssochlamys*, the genus *Thermoascus*, the genus *Monascus*, the genus *Aspergillus* and the genus *Penicillium*. In particular preferred are fungi of the species: *Paecilomyces divaricatus*, *Paecilomyces variotii*, *Byssochlamys nivea*, *Byssochlamys verrucosa*, *Thermoascus aurantiacus*, *Penicillium chrysogenum*, *Aspergillus japonicus*, *Aspergillus niger*, *Aspergillus ndulans*, *Aspergillus fumigatus* and *Aspergillus oryzae*.

Preferred fungi strains are: *Byssochlamys verrucosa* CBS 605.74, *Paecilomyces divaricatus* CBS 284.48, *Paecilomyces divaricatus* CBS 110429, *Paecilomyces variotii* Bainier SANK 21086, *Thermoascus crustaceus* CBS 11766, *Thermoascus thermophilus* CBS 624.74, *Aspergillus nidulans* ATCC 11414 or *Aspergillus fumigatus* ATCC 46645, *Aspergillus niger* ATCC 10864 and *Penicillium chrysogenum* ATCC 11500, *Aspergillus oryzae* ATCC 1015, *Aspergillus oryzae* ATCC 42149.

Preferred yeasts are selected from the group consisting of: the genus *Saccharomyces*, the genus *Ashbya*, the genus *Schizosaccharomyces*, the genus *Candida* and the genus *Pichia*.

In one embodiment the yeast is *Saccharomyces cerevisiae*.

In one a further embodiment, the recombinant microorganism is of the species *Paecilomyces divaricatus*, preferably selected from the group of strains of: *Paecilomyces divaricatus* CBS 284.48, *Paecilomyces divaricatus* CBS 110429, *Paecilomyces variotii* Bainier SANK 21086

In another embodiment, recombinant microorganism is a fungus or yeast, but not of the species *Paecilomyces divaricatus*, preferably, a recombinant microorganism belonging to genus *Penicillium*, *Aspergillus* or *Saccharomyces*, more preferred belonging to the species: *Penicillium chrysogenum*, *Aspergillus japonicus*, *Aspergillus niger*, *Aspergillus nidulans*, *Aspergillus fumigatus* and *Aspergillus oryzae*, or *Saccharomyces cerevisiae*.

Another part of the invention is a process to produce a recombinant microorganism comprising the steps of: a) transforming a microorganism with a polynucleotide of the invention or a vector comprising such a polynucleotide; and b) selecting a microorganism comprising said polynucleotide or said vector.

A further part of the invention is a process to produce a recombinant microorganism for the production of cornexistin or hydroxycornexistin or the production of cornexistin and hydroxycornexistin comprising the steps of: a) transforming a microorganism with a polynucleotide of the invention or a vector comprising such a polypeptide, b) selecting a microorganism comprising the polynucleotide or the vector, c) selecting a recombinant microorganism of step b) producing cornexistin or hydroxycornexistin or producing cornexistin and hydroxycornexistin.

The recombinant microorganisms can be tested for the production of cornexistin or hydroxycornexistin or the production of cornexistin and hydroxycornexistin, by culturing the recombinant microorganism under conditions which allow for the production of cornexistin or hydroxycornexistin or the production of cornexistin and hydroxycornexistin and analysing the recombinant microorganism or the culture medium or analysing the recombinant microorganism and the culture medium for the presence of cornexistin or hydroxycornexistin or the presence of cornexistin and hydroxycornexistin.

In particular preferred polynucleotides used to produce recombinant microorganisms are selected from the group comprising:

recombinant polynucleotides comprising a nucleic acid sequence being at least 80%, 82%, 84%, 86%, 88%, 90%, 91%, 92%, 93%, 94%, 95%, 96%, 97%, 98%, 99%, or 100% identical to the nucleic acid sequence as shown in SEQ ID NO: 1, or having at least 80%, 82%, 84%, 86%, 88%, 90%, 91%, 92%, 93%, 94%, 95%, 96%, 97%, 98%, 99%, or 100% of the sequence length of the nucleic acid sequence as shown in SEQ ID NO: 1, recombinant polynucleotides comprising a nucleic acid sequence being at least 70%, 72%, 74%, 76%, 78%, 80%, 82%, 84%, 86%, 88%, 90%, 91%, 92%, 93%, 94%, 95%, 96%, 97%, 98%, 99%, or 100% identical to the nucleic acid sequence as shown by the sequence of nucleotide 12423 to nucleotide 52300 of SEQ ID NO: 1 and comprising at least one expression cassette for at least one, two, three, four, five, six, seven, eight, or all polypeptides having an amino acid sequence as shown in SEQ ID NOs: 13, 15, 19, 25, 27, 29, 35, 37 and 41, or their variants in sequence identity and sequence length, recombinant polynucleotides comprising a nucleic acid sequence comprising at least one or more expression cassettes for at least one, two, three, four, five, six, seven, eight or all of the polypeptides described by SEQ ID NOs: 13, 15, 19, 25, 27, 29, 35, 37 and 41, or their variants in sequence identity and sequence length, recombinant polynucleotides comprising a nucleic acid sequence comprising at least one or more expression cassettes for at least one, two or all of the polypeptides described by SEQ ID NOs: 17, 21 and 33, or their variants in sequence identity and sequence length, recombinant polynucleotides comprising a nucleic acid sequence comprising at least one or more expression cassettes for at least one or both of the polypeptides described by SEQ ID NOs: 13 and 15, or their variants in sequence identity and sequence length, recombinant polynucleotides comprising a nucleic acid sequence comprising at least one or more expression cassettes for at least one or both of the polypeptides described by SEQ ID NOs: 19 and 27 or their variants in sequence identity and sequence length, recombinant polynucleotides comprising a nucleic acid sequence comprising at least one or more expression cassettes for at least one or both of the polypeptides described by SEQ ID NOs: 29 and 37 or their variants in sequence identity and sequence length, recombinant polynucleotides comprising a nucleic acid sequence comprising at least one or more expression cassettes for at least one or both of the polypeptides described by SEQ ID NOs: 35 and 41, or their variants in sequence identity and sequence length, recombinant polynucleotides comprising a nucleic acid sequence comprising at least one or more expression cassettes for a polypeptide described by SEQ ID NOs: 13, or its variants in sequence identity and sequence length, recombinant polynucleotides comprising a nucleic acid sequence comprising at least one or more expression cassettes for a polypeptide described by SEQ ID NOs: 15, or its variants in sequence identity and sequence length, recombinant polynucleotides comprising a nucleic acid sequence comprising at least one or more expression cassettes for a polypeptide described by SEQ ID NOs: 25, or its variants in sequence identity and sequence length, and recombinant polynucleotides comprising a nucleic acid sequence comprising at least one or more expression cassettes for a polypeptide described by SEQ ID NOs: 41, or its variants in sequence identity and sequence length.

Methods to test for the presence of cornexistin or hydroxycornexistin are known in the art. Examples for such methods are disclosed in U.S. Pat. Nos. 4,897,104, 4,990,178 and 5,424,278.

The present invention provides also for a process for the production of cornexistin or hydroxycornexistin or the production of cornexistin and hydroxycornexistin comprising the steps of: a) cultivating the recombinant microorganism comprising at least one polynucleotide of the invention under conditions which allow for the production of cornexistin or hydroxycornexistin or cornexistin and hydroxycornexistin by said recombinant microorganism; and b) obtaining produced cornexistin or produced hydroxycornexistin or obtaining produced cornexistin and hydroxycornexistin. Preferably cornexistin or hydroxycornexistin or cornexistin and hydroxycornexistin are obtained from the culture broth The produced cornexistin or hydroxycornexistin or the produced cornexistin and hydroxycornexistin can be obtained directly, or can be converted to their dibasic acid form and obtained as salts, preferably as agriculturally acceptable salts.

Accordingly, the present invention also encompasses a process for the production of the free dibasic acid of cornexistin or of agriculturally acceptable salts of cornexistin, comprising the steps of: a) cultivating the recombinant microorganism comprising at least one polynucleotide of the invention under conditions which allow for the production of cornexistin, and b) obtaining produced cornexistin and producing the dibasic acid of cornexistin or producing agriculturally acceptable salts of the dibasic acid of cornexistin. Alternatively, process for the production of the free dibasic acid of cornexistin or of agriculturally acceptable salts of cornexistin, comprises the steps of: a) cultivating the recombinant microorganism comprising at least one polynucleotide of the invention under conditions which allow for the production of cornexistin, b) producing the dibasic acid of cornexistin or producing agriculturally acceptable salts of the dibasic acid of cornexistin and c) obtaining the dibasic acid of cornexistin or obtaining agriculturally acceptable salts of the dibasic acid of cornexistin.

A further embodiment of the invention is a process for the production of the free dibasic acid of hydroxycornexistin or of agriculturally acceptable salts of hydroxycornexistin, comprising the steps of: a) cultivating the recombinant microorganism comprising at least one polynucleotide of the invention under conditions which allow for the production of hydroxycornexistin, and b) obtaining produced hydroxycornexistin and producing the dibasic acid of hydroxycornexistin or producing agriculturally acceptable salts of the dibasic acid of hydroxycornexistin.

Alternatively, process for the production of the free dibasic acid of hydroxycornexistin or of agriculturally acceptable salts of hydroxycornexistin, comprises the steps of: a) cultivating the recombinant microorganism comprising at least one polynucleotide of the invention under conditions which allow for the production of hydroxycornexistin, b) producing the dibasic acid of hydroxycornexistin or producing agriculturally acceptable salts of the dibasic acid of hydroxycornexistin and c) obtaining the dibasic acid of hydroxycornexistin or obtaining agriculturally acceptable salts of the dibasic acid of hydroxycornexistin.

Methods to produce the dibasic acid of cornexistin and agriculturally acceptable salts of cornexistin are known in the art and, for example, disclosed in U.S. Pat. Nos. 4,897,104 and 4,990,178, which are included herein by reference in their entirety.

Methods to produce the dibasic acid of hydroxycornexistin and agriculturally acceptable salts of hydroxycornexistin are known in the art and, for example, disclosed in U.S. Pat. No. 5,424,278, which is included herein by reference in its entirety.

The term "cultivating" as used herein refers maintaining and growing the recombinant microorganisms under culture conditions which allow the cells to produce the said cornexistin and hydroxycornexistin or a precursor thereof referred to above. This implies that the polynucleotide of the present invention is expressed in the recombinant microorganism so that the polypeptide(s) encoded by the at least one nucleic acid sequence is present in the recombinant microorganism in a biologically active form. Suitable culture conditions for cultivating the recombinant microorganism are described in more detail in the accompanying Examples below. In particular, recombinant microorganisms of the present invention, preferably, can be cultured using, for example, glucose, sucrose, honey, dextrin, starch, glycerol, molasses, animal or vegetable oils and the like as the carbon source for the culture medium. Furthermore, soybean flour, wheat germ, corn steep liquor, cotton seed waste, meat extract, polypeptone, malt extract, yeast extract, ammonium sulfate, sodium nitrate, urea and the like can be used for the nitrogen source. The addition of inorganic salts which can produce sodium, potassium, calcium, magnesium, cobalt, chlorine, phosphoric acid (di-potassium hydrogen phosphate and the like), sulfuric acid (magnesium sulfate and the like) and other ions as required is also effective. Furthermore, various vitamins such as thiamine (thiamine hydrochloride and the like), amino acids such as glutamine (sodium glutamate and the like), asparagine (DL-asparagine and the like), trace nutrients such as nucleotides and the like, and selection drugs such as antibiotics and the like can also be added as required. Moreover, organic substances and inorganic substances can be added appropriately to assist the growth of the microorganism and promote the production of cornexistin and hydroxycornexistin or the precursor thereof. The pH of the culture medium is, for example, of the order of pH 4.5 to pH 8. The culturing can be carried out with a method such as the solid culturing method under aerobic conditions, the concussion culturing method, the air-passing agitation culturing method or the deep aerobic culturing method, but the deep aerobic culturing method is the most suitable. The appropriate temperature for culturing is from 15° C. to 40° C., but in many cases growth occurs in the range from 20° C. to 30° C. The production of cornexistin and hydroxycornexistin or its precursors differs according to the culture medium and culturing conditions, or the host which is being used, but with any culturing method the accumulation of cornexistin and hydroxycornexistin reaches a maximum generally in from 5 to 20 days. The culturing is stopped when the amount of cornexistin and hydroxycornexistin or its precursor in the culture reaches its highest level and the target material is isolated from the culture and refined for isolating cornexistin and hydroxycornexistin or a precursor thereof from the culture material.

Examples for such conditions which allow for the production of cornexistin and hydroxycornexistin are disclosed in U.S. Pat. Nos. 4,897,104, 4,990,178 and 5,424,278 which are included herein by reference in their entirety.

The term "obtaining" as used herein encompasses the provision of the cell culture including the recombinant microorganisms and the culture medium as well as the provision of purified or partially purified preparations thereof comprising the cornexistin and hydroxycornexistin or a precursor thereof, preferably, in free form. More details on purification techniques can be found elsewhere herein below. The usual methods of extraction and refinement which are generally used in these circumstances, such as methods of isolation such as solvent extraction, methods involving ion exchange resins, adsorption or partition chromatography, gel filtration, dialysis, precipitation, crystallization and the like can be used either individually or in appropriate combinations. In particular, cornexistin and hydroxycornexistin can be isolated from a cornexistin and hydroxycornexistin containing medium or lysate using a known method for isolating cornexistin and hydroxycornexistin. Preferably, the process for isolation disclosed by Furuta 1982, Agricultural and Biological Chemistry (1982), 46(7), 1921-2 is envisaged in accordance with the method of the present invention.

Examples for methods which allow to obtain cornexistin and hydroxycornexistin, their dibasic forms or their agriculturally acceptable salts are disclosed in U.S. Pat. Nos. 4,897,104, 4,990,178 and 5,424,278 which are included herein by reference in their entirety.

Further methods of the invention include a method to enhance the production of cornexistin or hydroxycornexistin or cornexistin and hydroxycornexistin in *Paecilomyces divaricatus* or *Byssochlamys verrucosa* by upregulating the activity of at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NOs: 13, 15, 19, 25, 27, 29, 35, 37 and 41, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NOs: 13, 15, 19, 25, 27, 29, 35, 37 and 41.

In one embodiment of the invention, the upregulated activity is the activity of at least one polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NOs: 13, 15, 25, 35 and 41, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NOs: 13, 15, 25, 35 and 41.

A further method is a method to enhance the production of hydroxycornexistin in *Paecilomyces divaricatus* or *Byssochlamys verrucosa* by upregulating the activity of a polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NOs: 15, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NOs: 15.

Another method of the invention is a method to enhance the production of cornexistin in *Paecilomyces divaricatus* or *Byssochlamys verrucosa* by downregulating the activity of a polypeptide having an amino acid sequence being at least 80%, 82%, 84%, 86%, 88%, 90%, 91%, 92%, 93%, 94%, 95%, 96%, 97%, 98%, 99%, or 100% identical to an amino acid sequence as shown in SEQ ID NOs: 15, or having at least 80%, 82%, 84%, 86%, 88%, 90%, 91%, 92%, 93%, 94%, 95%, 96%, 97%, 98%, 99%, or 100% of the sequence length of a nucleic acid sequence as shown by SEQ ID NOs: 15.

The polynucleotides provided by the invention also allow to identify microorganisms being capable to produce cornexistin or hydroxycornexistin or being capable to produce cornexistin and hydroxycornexistin.

Accordingly, the invention encompasses a method to identify microorganisms capable to produce cornexistin or hydroxycornexistin or capable to produce cornexistin and hydroxycornexistin comprising the steps of: a) providing genomic DNA or cDNA of a microorganism or of a recombinant microorganism and; b) testing the genomic DNA or cDNA for the presence of at least one polynucleotide of the invention.

Finally, encompassed by the present invention is the use of the polynucleotide, the vector or the recombinant microorganism of the invention, in general, for the production of cornexistin and hydroxycornexistin in any of the methods disclosed herein.

All references cited in this specification are herewith incorporated by reference with respect to their entire disclosure content and the disclosure content specifically mentioned in this specification.

EXAMPLES

To isolate and clone the cornexistin and hydroxycornexistin gene cluster the transformation-associated recombination (TAR) cloning in the yeast *Saccharomyces cerevisiae* is used. This method is based on in vivo recombination between genomic DNA and a linearized TAR cloning vector containing targeting the respective sequences homologous to the region of interest (described in the following as hooks). The method is described in the publications such as Larionov et al. 1996, Proc. Natl. Acad. Sci. USA 93: 491-496 and Kouprina and Larionov 2008 (Kouprina and Larionov 2008, Nature Protocols 3: 371-377 The cloning of the cluster is done as described by Kouprina and Larionov 2008 (Kouprina and Larionov 2008, Nature Protocols 3: 371-377) as described below:

Example 1 Sequencing of Genomic DNA of *Paecilomyces divaricatus* SANK 21086

Chromosomal DNA of the fungal strain SANK 21086 was isolated using the DNAeasy kit from Qiagen according to the protocol. The DNA was subjected to DNA sequencing and the resulting sequences were assembled and ordered to contig sequences. Contig sequences were analysed for orfs and resulting proteins by intron and exon identification. Annotation was performed and orfs were named. The gene cluster for cornexistin and hydroxycornexistin is identified by genome analysis and functional characteristics of the contained enzymatic activities of the respective proteins for which the DNA codes.

Example 2 Construction of the TAR Cloning Vector p9399

The plasmid is generated based on the yeast-*E. coli* shuttle vector pVC-604, being available via the American Type Culture Collection ATCC No.: MBA-212 and containing a yeast selectable marker (HIS3) and a yeast centromeric sequence (CEN6). Plasmid pVC-604 is digested with BamHI to integrate the first hook (SEQ ID NO: 56) representing 300 bp homologous sequences to the 5' flanking region of the cornexistin/hydroxycornexistin cluster. The DNA fragment with the SEQ ID NO: 56 is PCR amplified, purified and ligated in the corresponding BamHI site of pVC-604. In the same way, the second hook (SEQ ID NO: 57) containing 300 bp of the 3'-flanking region of the cornexistin/hydroxycornexistin cluster is PCR amplified and ligated into the EcoRI restriction site to generate plasmid p9399. This plasmid is isolated in high amounts using the DNA Maxi Kit (Qiagen) and 5 µg plasmid-DNA are linearized by SmaI and purified by gel extraction. The linearized plasmid is used subsequently in the TAR cloning experiment.

Example 3 Preparation of Genomic DNA

The genomic DNA of *Paecilomyces divaricatus* SANK 21086 for the TAR cloning experiment is isolated using the ZR Fungal/Bacterial DNA MiniPrep (Zymo Research) according to the protocol of the supplier.

Example 4 Preparation of Competent Yeast Spheroplasts

One day before the TAR cloning experiment, 50 ml YEPD medium (2% glucose, 1% bacto yeast extract, 2% bacto peptone, 80 mg/l adenine hemisulfate) is inoculated with yeast strain VL6-48, being available via the American Type Culture Collection ATCC No.: MYA-3666, and incubated overnight at 30° C. until OD660 of 3.0-5.0 is achieved. The yeast cells are harvested by centrifugation for 5 min at 1000 g and 5° C., washed in 30 ml of sterile water and resuspended in 20 ml of 1 M sorbitol. After centrifugation for 5 min at 1000 g and 5° C. the cell pellet is resuspended in 20 ml of SPE solution (1 M sorbitol, 0.01 M Na$_2$HPO$_4$ 0.01 M Na$_2$EDTA, pH7.5). Subsequently, 20 µl of zymolyase solution (10 mg/ml zymolyase 20T in 25% (w/v) glycerol) and 40 µl of ME are added and incubated at 30° C. for 20 min with slow shaking. The spheroplasts are centrifuged for 10 min at 570 g at 5° C. and the pellet is resuspended in 50 ml 1 M sorbitol. After repeating the washing step, the final pellet is gently dissolved in 2 ml of STC solution (1 M sorbitol, 0.01 M Tris-HCl, 0.01 M CaCl$_2$, pH 7.5).

Example 5 Transformation of Spheroplasts by Genomic DNA Along with the TAR Vector p9399

200 µl of the spheroplast suspension is mixed with 2-3 µg of genomic DNA and 1 µg of the linearized p9399 vector and incubate for 10 min at room temperature. 800 µl of PEG8000 solution (20% PEG8000, 10 mM CaCl$_2$, 10 mM Tris-HCl, pH7.5) is added and the sample is incubated for 10 min at room temperature. After centrifugation for 5 min at 300-500 g at 5° C., the spheroplasts are resuspended in 800 µl of SOS solution (1 M sorbitol, 6.5 mM CaCl$_2$, 0.25% yeast extract, 0.5% peptone) and incubated for 40 min at 30° C. without shaking. The spheroplasts are transferred into a tube containing 7 ml of melted SORB-TOP-His selection medium (1 M sorbitol, 2% D-glucose, 0.17% yeast nitrogen base, 0.5% (NH$_4$)$_2$SO$_4$ and 3% bacto agar containing the following supplements: 0.006% adenine sulfate, 0.006% uracil, 0.005% L-arginine.HCl, 0.008% L-aspartic acid, 0.01% L-glutamic acid, 0.005% L-isoleucine, 0.01% L-leucine, 0.012% L-lysine.HCl, 0.002% L-methionine, 0.005% L-phenylalanine, 0.0375% L-serine, 0.01% L-threonine, 0.005% L-tryptophan, 0.005% L-tyrosine and 0.015% L-valine) gently mixed and quickly poured onto SORB-His plates with selective medium. The plates are incubated for 5-7 days at 30° C. until transformants become visible.

Example 6 Identification of Gene-Positive Pools 300 primary transformants are transferred by toothpicks onto SD-His plates (2% D-glucose, 0.17% yeast nitrogen base, 0.5% (NH$_4$)$_2$SO$_4$, 2% bacto agar supplemented as described in SORB-TOP-His), 30 colonies are plated onto each master plate, and incubated at 30° C. for 2-3 days. Replica plates of each master plate are performed and the master plate is used for detection of gene-positive pools. The yeast cells from each master plate are washed out with 5 ml of water and the cells are pelleted by centrifugation for 5 min at 1000 g at 5° C. The cell pellet are resuspended in 1 ml of 1 M sorbitol solution, centrifuged for 30 s at 2000 g at room temperature and again resuspended in 0.5 ml of SPE solution containing ME (1/1000 dilution). After adding 20 µl of zymolyase solution, each sample is incubated for 2 h at 30° C. The spheroplasts are harvested by centrifugation for 5 min at 2000 g at room temperature and are resuspended in 0.5 ml of EDTA. Lysing of spheroplasts is induced by adding 1 µl of diethylpyrocarbonate and incubation at 70° C. for 15 min. After adding of 50 µl of 5 M KAc solution the tubes are incubated for 30 min on ice. The precipitate is pelleted by centrifugation for 15 min at maximum speed (16,000 g) at room temperature and the supernatant is transferred to a fresh tube. The DNA is extracted by ethanol at room temperature and the pelleted by centrifugation for 5 min at maximum speed (16,000 g) at room temperature. The pellet is resuspended in 0.4 ml of water. After washing in 0.5 ml of isopropanol the final pellet is dissolved in 0.3 ml of water. 1 µl of the DNA solution is used in 50 µl PCR with two diagnostic primer pairs P1f: 5'-GGAATAAGCAG-GAATGGTTC-3'; (Seq ID NO: 48) P1r: 5'-CGCATCCAT-TCTGG AGAAAC-3'; (SEQ ID NO: 49), P2f: 5'-CGCTG-GATCTCGGCGTTATC-3' (SEQ ID NO: 50), P2r: 5'-GCTGAGCTATCTTCTCCGACAAC-3') (SEQ ID NO: 51) to identify gene-positive pools. The PCR is done according to the Taq polymerase manufacturer's protocols. Using both primer pairs, gene-positive pools show an amplicon of 502 bp and 558 bp, respectively.

Example 7 Identification and Analysis of Individual Gene-Positive Clones in Pools Each transformant from replica plates with positive pools is added into 100 µl mixture of 80 ml water, 20 µl zymolyase solution and 1 µl of ME and incubated for 1 h at 30° C. After adding 10 µl of 2% SDS solution and another 15 min incubation at 70° C., 10 µl of 5 M KAc solution is added and the samples are left on ice for 15 min. After centrifugation, the supernatant is transferred to a new tube and an equal amount of isopropanol is added. The sample is precipitated and the final pellet is dissolved in 30 µl of water. 1 µl of the DNA solution is used in 50 µl PCR with the above mentioned diagnostic primer pairs. The PCR is done according to the Taq polymerase manufacturer's protocols. Yeast recombinants that produced PCR amplicons of correct size are grown overnight at 30° C. and 225 rpm in 2 ml of SD-His media. The DNA is isolated using the ChargeSwitch (Invitrogen) Nucleic Acid Purification Technology and transformed in E. coli electrocompetent cells to amplify the cloned DNA (Kim et al. 2010 Biopolymers 93: 833-844).

Clones containing the gene cluster described by Seq ID 1 are identified as described above leading to the plasmid p9399_Co1, DNA from the strain containing p9399_Co1 is subsequently prepared for transformation purposes.

Example 8 Co-Transformation of p9399_Co1 and the nat1 Resistance Marker

The cloned Cornexistin/hydroxycornexistin cluster is co-transformed with plasmid pPtrpC-Pcnat1 (SEQ ID NO: 58) into *Paecilomyces divaricatus* SANK 21086. The plasmid contains the codon-optimized nat1 resistance marker gene to select positive *Paecilomyces divaricatus* transformants. Cotransformation can be done according to the protocol described in WO12116935. In addition fungal spores can be also transformed. Clones harboring the nat1 resistance marker gene as well as the recombinant plasmid p9399_Co1 containing the gene cluster coding for the enzymes of the Cornexistin/hydroxycornexistin biosynthesis are identified by isolating genomic DNA and performing PCR using the primers

```
                                    SEQ ID NO: 52
(5'-CGACGGCCAGTGAATTGTAATAC-3')
and SEQ ID NO: 53
(5'-GGAGGTAACCCACCTTTCTG-3')
or SEQ ID NO: 54
(5'-GAGCCACCTTTCCCAGAATG-3')
and

SEQ ID NO: 55
(5'-GCTCCTATGTTGTGTGGAATTG-3').
```

Positive clones show bands of 711 bp and 703 bp, respectively.

Example 9 Production of Cornexistin/Hydroxycornexistin Using SANK 21086 p9399_Co1

A transformant SANK 21086 p9399_Co1 is grown in an erlenmayer shake flask without baffles containing following medium: 5% Potato flakes, 5% Glycerol, 0.4% Urea, pH 6 and at 220 rpm in a rotary shaker with an amplitude of 4 cm. After 336 h of incubation at 26° C. cultures are harvested by centrifugation (10000 g 20 min). Cornexistin as well as hydroxycornexistin are isolated from the broth and the concentration is determined by HPLC analysis as described:

TABLE 3

Results of Example 9:

| Strain | Productivity of cornexistin | Productivity of hydroxycornexistin |
|---|---|---|
| SANK 21086 | + | + |
| SANK 21086 pPtrpC-Pcnat1 | + | + |
| SANK 21086, p9399_Co1 | ++ | ++ |

Example 10 Cloning of Overexpression Cassettes for the Production of Cornexistin and Hydroxycornexistin Using Heterologous Promoters Genes coding for the biosynthesis of cornexistin and hydroxycornexistin are expressed using heterologous promoters such as the Ptrpc promoter of *A. nidulans*. Promoter gene terminator fusions can be obtained by several technologies known to the person skilled in the art. Technologies are PCR fusion using overlapping primers for the promoter 3' side and the gene 5' side as well as promoter 5' primers and gene-terminator 3' primers. Methods for performing PCR fusion can be found in Nucl. Acids Res. (1989) 17: 4895. Another possible way to obtain promoter-gene terminator-fusion ca be DNA synthesis 2009 by known methods (Czar et al. Trends in Biotechnology, 27, 63-72 and references therein).

Fragments containing promoter gene terminator fusions can be combined by several methods such as the Biobrick method, the Golden Gate Method, the SLIC Method, the CEPC Method (Li et al. Nature Methods 2007, 4: 251-256, Quan et al. PLOS ONE 4: e6441, Engler et al. PLOS ONE, 2008, 3 e3647, Engler et al. PLOS ONE, 2009 4 e5553).

All cassettes containing the promoter PtrpC (Seq ID NO. 32) and the genes coding for the open reading frame 1_9399 (Seq ID No. 2), the orf 2_9399 (Seq ID No. 4), the orf 3_9399 (Seq ID No. 6), the orf 4_9399 (Seq ID No. 8), the orf 5_9399 (Seq ID No. 10), the orf 6_9399 (Seq ID No. 12), the orf 7_9399 (Seq ID No. 14), the orf 8_9399 (Seq ID No. 16), the orf 9_9399 (Seq ID No. 18) the orf 10_9399 (Seq ID No. 20), the orf 11_9399 (Seq ID No. 22), the orf 12_9399 (Seq ID No. 24), the orf 13_9399 (Seq ID No. 26), the orf 14_9399 (Seq ID No. 28) the orf 15_9399 (Seq ID No. 30) the orf 16_9399 (Seq ID No. 32) the orf 17_9399 (Seq ID No. 34) the orf 18_9399 (Seq ID No. 36) the orf 19_9399 (Seq ID No. 38) the orf 20_9399 (Seq ID No. 40) the orf 21_9399 (Seq ID No. 42) the orf 22_9399 (Seq ID No. 44) the orf 23_9399 (Seq ID No. 46) are constructed by methods described above and cloned together or in two or more parts into the vector pHS1 nat1 or vector pHS1 delta nat1. Fragments containing the all promoter-orf terminator cassettes can be isolated from the vectors using the SwaI digestion and are used for transformation of suitable fungal strains.

Example 11 Transformation of Cornexistin and Hydroxycornexistin Cluster DNA into *Paecilomyces divaricatus*

250 μl of a spore suspension are inoculated into a 500 ml flask with one baffle containing 100 ml of CCM medium (for one transformation experiment two flasks), and are incubated for 3 days at 27 C and 120 rpm. Mycelium is harvested by filtration and washed by adding 20 ml of PP-buffer (0.9 M NaCl). The dried mycelium is transferred in a sterile flask, 30 ml of 3% Glucanex solution is added. Incubation is performed for 2 h at 27 C and 100 rpm followed microscopic control of formed protoplasts. Filtration of protoplasts using a frit (pore size 1) is performed Centrifugation of the protoplast suspension is performed for 5 min at 4 C and 2500 rpm. Supernatant is discarded and the protoplast pellet is dissolved in 10 ml PP-buffer.

The protoplast suspension is centrifuged for 5 min at 4 C and 2500 rpm in a sterile tube The pellet is dissolved in 5 ml TP1-buffer (0.9 M NaCl, 50 mM CaCl2).

The protoplast titre is determined using a Abbe-Zeiss counting cell chamber and the titre is adjusted to $1 \times 10^8$ protoplasts/ml TP1-buffer. 10 microgram of linear DNA 1 and 2 are mixed with 50 µl of the protoplast suspension. 12.5 µl of TP2-buffer (25% PEG 6000, 50 mM CaCl2, 10 mM Tris, pH 7.5) are added and incubated for 20 min on ice. 500 µl of TP2-buffer are added, mixed gently and incubated 5 min at RT. 1 ml TP1-buffer are added. 2×780 µl of the transformation approach are mixed with 4 ml topagar I (CCM+20% sucrose+0.8% agar) and poured on CCMS plates. Plates are incubated at 27 C over night. All plates with expect of the regeneration controls are overlayed with 11 ml topagar II (0.8 M NaCl, 0.8% agar+Nourseothricine 50 µg/ml) and are incubated for >6 days at 27 C. Clones resistant against Nourseothricin are isolated, purified and analyzed for CC production in shake flask experiments.

Example 12 Transformation of Cornexistin and Hydroxycornexistin Cluster DNA into *Aspergillus niger* and *Aspergillus oryzae*

An *Aspergillus oryzae* strain, such as ATCC 1015 or *Aspergillus oryzae* ATCC 42149, or another strain, is cultured for 1 week at 30° C. in CD-Met (containing 40 µg/ml L-methionine) agar culture medium. Conidia ($>10^8$) are recovered from the Petri dish and inoculated into 100 ml of YPD liquid culture medium in a 500 ml flask. After culturing for 20 hours (30° C., 180 rpm), an aegagropila-like biomass is obtained. The biomass is collected on a 3G-1 glass filter and washed with 0.8M NaCl and then de-watered thoroughly and suspended in TF solution I (protoplastizing solution) and shaken for 2 hours at 30° C., 60 rpm. The material is examined with a microscope every 30 minutes and the presence of protoplasts is confirmed. Subsequently, the culture liquid is filtered and the protoplasts are recovered by centrifugal separation (2000 rpm, 5 minutes) and then washed with TF solution II. After washing, 0.8 vol of TF solution II and 0.2 vol of TF solution III are added and admixed and a protoplast suspension is obtained.

Plasmid DNA (10 p g of each vector DNA) of the Vector for Introduction, p9399_Co1 and of ptrpC nat1 is added to 200 µl of this liquid suspension and left to stand over ice for 30 minutes, TF solution III (1 mL) is added and then mixed gently. Subsequently the mixture is left to stand for 15 minutes at room temperature and the plasmid DNA is introduced into the aforementioned protoplasts. TF solution 11 (8 mL) is added and the mixture is centrifuged (5 minutes at 2,000 rpm) and 1 to 2 ml of residual protoplast is recovered. The recovered protoplast liquid is dripped into re-generating culture medium (lower layer), the regenerating culture medium (upper layer) is poured in and, after mixing by rotating the Petri dish, the mixture is cultured for from 4 to 5 days at 30° C. The clones which emerged are isolated in regenerating culture medium (lower layer) and the transfectants (*Aspergillus oryzae* ATCC 1015 and *Aspergillus oryzae* ATCC 42149) are obtained by successive purification.

The abovementioned TF solution I (protoplastizing solution) is prepared using the composition indicated below.

| Compound | Concentration |
| --- | --- |
| Yatalase (Produced by the Takara-Bio Co.) | 25 mg/ml |
| Ammonium sulfate | 0.65M |
| Maleic Acid - NaOH | 55 mM |

The abovementioned composition is prepared (pH 5.6) and then subjected to filtration sterilization. The abovementioned TF solution II is prepared using the composition indicated below.

| Compound | |
| --- | --- |
| 1.1M Sorbitol | |
| 50 mM CaCl$_2$ | 10 ml 1M CaCl$_2$ (1/20) |
| 35 mM NaCl | 1.4 ml 5M NaCl |
| 10 mM Tris-HCl | 2 ml 1M Tris-HCl (1/100) |
| Up to total volume | 200 ml |

The abovementioned composition is prepared and then subjected to autoclave sterilization. The abovementioned TF solution Ill is prepared using the composition indicated below.

| Compound | |
| --- | --- |
| 60% PEG 4000 | 6 g |
| 50 mM CaCl$_2$ | 500 µl 1M CaCl$_2$ (1/20) |
| 50 mM Tris-HCl | 500 µl 1M Tris-HCl (1/100) |
| Up to total volume | 10 ml |

The abovementioned composition is prepared and then subjected to filtration sterilization.

The abovementioned culture medium is prepared using the composition indicated below.

| Compound | Concentration |
| --- | --- |
| Sorbitol (MW = 182.17) | 218.6 g 1.2M |
| NaNO$_3$ | 3.0 g 0.3% (w/v) |
| KCl | 2.0 g 0.2% (w/v) |
| KH$_2$PO$_4$ | 1.0 g 0.1% (w/v) |
| MgSO$_4$•7H$_2$O | 2 ml of 1M MgSO$_4$ 0.05% 2 mM |
| Trace Elements Solution | 1 ml |
| Glucose | 20.0 g 2% (w/v) |
| Up to the total volume | 1 L |

The abovementioned composition (pH 5.6) is prepared and then subjected to autoclave sterilization.

Example 13 Transformation of *Aspergillus nidulans* and *Aspergillus fumigatus*

Protoplasts are prepared from five cellophane cultures of *A. nidulans* (ATCC 11414, ATCC 10864, or another strain) or *A. fumigatus* (ATCC 46645, or another strain) as described in Ballance et al., Biochem. Biophys. Res. Commun. 112 (1983) 284-2X9. After filtration through nylon filter cloth (Gallenkamp, GMX-500-V) and sintered glass (porosity I), the protoplasts are centrifuged at 1000×g for 5 min and then washed twice with 0.6 M KCl and once with 0.6 M KCl, 50 mM CaCl. The protoplasts are resuspended in 0.2 ml of 0.6 M KCl, 50 mM CaCl (0.5–5×10$^8$ ml and then 50-4 aliquots are dispensed into screw-capped tubes (Sarstedt). DNA (1 pg) is then added, followed by 12.5~1 25% PEG 6000 (BDH), 50 mM CaCl, 10 mM Tris' HCl, pH 7.5. After 20 min incubation on ice, 0.5 ml of the above PEG solution is added and the mixture left at room temperature for 5 min. One ml of 0.6 M KCl, 50 mM CaCl, is added and aliquots are added to molten minimal medium containing KCl (0.6 M) and agar (2% w/v) which is then poured over minimal agar plates. When necessary, the transformation mixture is diluted in 0.6 M KCl, 50 mM CaCl. The efficiency of regeneration is assessed by plating aliquots of a 10$^{-3}$ dilution of the final transformation mixture in complete medium containing KCl and nourseothricin. All plates with expect of the regeneration controls are overlayed with 11 ml topagar 11 (0.8 M NaCl, 0.8% agar+Nourseothricine 50 μg/ml) and are incubated for >6 days at 27 C.

Clones capable of growing on the antibiotic are isolated, purified by repeated incubation on Nourseothricin containing agar plates and are used for cornexistin and hydroxycornexistin production experiments.

Example 14 Growth of Fungal Strains after Transformation with DNA

Growth of fungal strains after transformation with DNA Media and cultivation of microorganisms:

*Aspergillus nidulans, Aspergillus japonicus, Aspergillus fumigatus, Aspergillus niger* ATCC 10864, and *Penicillium chrysogenum* ATCC11500 strains that are successfully transformed with the genes of the cornexistin and hydroxycornexistin gene cluster from plasmid p9399_Co1 are cultivated at the appropriate incubation temperature (26° C. for *Penicillium chrysogenum*, 30° C. for *A. niger* and *A. japonicus*, 37° C. for *A. fumigatus* and *A. nidulans*) in YG (0.5% Yeast extract, 2% glucose), complete medium, or *Aspergillus* minimal medium with 1% (w/v) glucose as the carbon source and 5 mM of sodium glutamate as the nitrogen source and tryptophan (Biophys Acta 113:51-56).

B. Alternatively the strains are grown on a medium containing

Glucose-monohydrate 80 g/l, defatted wheat germ meal 10 g/l, defatted soy bean meal 16 g/l, L-glutamate 3 g/l, NaCl 1.25 g/l, CaCO3 1.5 g/l, silicon oil KM-72 0.03 g/l. Alternatively the strains are grown in a medium containing 30 g/l Mannitol, 10 g/l glucose, 10 g/l succinic acid, 1 g/l KH2PO4 0.3 g/l MgSO4*7H2O, with NH4OH to adjust the pH to 5.6. Alternatively the strains are grown in a medium that promotes the synthesis of ergotamines (Hernandez, Process Biochemistry 1993 28 23-27) In all cases L-tryptophan and or mevalonic acid can be added in suitable amounts to increase the amount of produced compounds from the pathway including cornexisting and hydroxycornexistin. Solid media contained 1.5% Bacto-agar or, in the case of minimal agar plates, Difco-agar. If required, p-aminobenzoic acid (0.11 mM), nourseothricine (50 μg/ml) are added).

Clones resistant against the antibiotic are grown in 250 ml baffled shake flask with a power stroke of 5 cm at 160-250 rpm. 25 ml medium is inoculated with freshly grown mycelium and incubated for 7d at the appropriate incubation temperature (26° C. for *Penicillium*, 30° C. for *A. niger*, 37° C. for *A. fumigatus* and *A. nidulans*).

Cells as well as broth are harvested and are extracted as described in Furuta, Takaki; Koike, Masami; Abe, Matazo, Agricultural and Biological Chemistry (1982), 46, 1921-22

Example 15 Cornexistin and Hydroxycornexistin Produced by the Transformed Fungal Strains can be Analyzed by a Suitable HPLC Method Cornexistin and hydroxycornexistin are analyzed by the following HPLC method: An injection volume of a sample size of 2 μl is injected into a ROD-HLPC column, 50×4.6 mm (Merck KGa Darmstadt Germany) at a temperature of 40° C. For the elution a solvent as follows is used: acetonitril+0.1% TFA; water+0.1% TFA. The flow rate is set to 1.8 ml/min, detection of eluting compounds is performed by electrochemical detection. A standard of cornexistin and hydroxycornexistin is used for the calibration of the HPLC. Alternatively the following method can be used: Column: Eclipse XDB C18 (150*4.6 mm) at 40° C. with a flow rate of 1.00 mL/min and an injection volume of 10.0 μl. Detection was done at UV 210 nm. The maximal pressure was set to 300 bar. The Eluent A was H2O with 0.1% H3PO4, the eluent B was acetonitrile with the following gradient:

|  | A [%] | B [%] |  |
| --- | --- | --- | --- |
| 0.0 [min] | 80.0 | 20.0 | 1.00 |
| 5.0 [min] | 80.0 | 20.0 | 1.00 |
| 5.1 [min] | 65.0 | 35.0 | 1.00 |
| 16.0 [min] | 65.0 | 35.0 | 1.00 |
| 20.0 [min] | 0.0 | 100.0 | 1.00 |
| 30.0 [min] | 0.0 | 100.0 | 1.00 |

The invention claimed is:

1. A recombinant microorganism comprising a recombinant expression cassette, wherein said recombinant expression cassette comprises a promoter operably linked to:
   a) a polynucleotide having at least 98% sequence identity to the nucleic acid sequence of SEQ ID NO: 40; or
   b) a polynucleotide encoding a polypeptide having at least 98% sequence identity to the amino acid sequence of SEQ ID NO: 41,
   wherein said promoter is heterologous to said polynucleotide, and wherein the microorganism is *Paecilomyces divaricatus*.

2. The recombinant microorganism of claim 1, wherein said polynucleotide is operably linked to a terminator.

3. The recombinant microorganism of claim 1, wherein said polynucleotide is operably linked to an enhancer.

4. The recombinant microorganism of claim 1, wherein said polynucleotide is operably linked to a terminator and an enhancer.

5. The recombinant microorganism of claim 1, wherein said polynucleotide comprises the nucleic acid sequence of SEQ ID NO: 40.

6. The recombinant microorganism of claim 1, wherein said polynucleotide encodes a polypeptide comprising the amino acid sequence of SEQ ID NO: 41.

7. A recombinant microorganism comprising:
   a) a polynucleotide having at least 98% sequence identity to the nucleic acid sequence of SEQ ID NO: 40; or
   b) a polynucleotide encoding a polypeptide having at least 98% sequence identity to the amino acid sequence of SEQ ID NO: 41,
   wherein said polynucleotide is heterologous to the microorganism and is operably linked to a promoter, and wherein the microorganism is *Paecilomyces divaricatus*.

8. The recombinant microorganism of claim 7, wherein said polynucleotide is operably linked to a terminator.

9. The recombinant microorganism of claim 7, wherein said polynucleotide is operably linked to an enhancer.

10. The recombinant microorganism of claim 7, wherein said polynucleotide is operably linked to a terminator and an enhancer.

11. The recombinant microorganism of claim 7, wherein said polynucleotide comprises the nucleic acid sequence of SEQ ID NO: 40.

12. The recombinant microorganism of claim 7, wherein said polynucleotide encodes a polypeptide comprising the amino acid sequence of SEQ ID NO: 41.

13. A process for the production of cornexistin and/or hydrocornexistin, comprising cultivating the recombinant microorganism of claim 1 under conditions allowing for the production of cornexistin and/or hydrocornexistin by said recombinant microorganism.

14. The process of claim 13, further comprising obtaining cornexistin and/or hydrocornexistin from the culture broth.

15. The process of claim 13, wherein at least one of the cornexistin and/or hydrocornexistin is obtained as dibasic acid thereof or in the form of its agriculturally acceptable salt.

16. A process for the production of cornexistin and/or hydrocornexistin, comprising cultivating the recombinant microorganism of claim 7 under conditions allowing for the production of cornexistin and/or hydroxycornexistin by said recombinant microorganism.

17. The process of claim 16, further comprising obtaining cornexistin and/or hydroxycornexistin from the culture broth.

18. The process of claim 16, wherein at least one of the cornexistin and/or hydroxycornexistin is obtained as dibasic acid thereof or in the form of its agriculturally acceptable salt.

* * * * *